(12) United States Patent
Lunyak et al.

(10) Patent No.: US 11,293,065 B2
(45) Date of Patent: Apr. 5, 2022

(54) COMPOSITIONS AND METHODS FOR THE QUALITY CONTROL OF STEM CELL PREPARATIONS

(71) Applicant: Aelan Cell Technologies, Inc., San Francisco, CA (US)

(72) Inventors: Victoria Lunyak, San Anselmo, CA (US); Meenakshi Gaur, San Francisco, CA (US)

(73) Assignee: AELAN CELL TECHNOLOGIES, INC., San Francisco, CA (US)

( * ) Notice: Subject to any disclaimer, the term of this patent is extended or adjusted under 35 U.S.C. 154(b) by 0 days.

(21) Appl. No.: 16/084,877

(22) PCT Filed: Mar. 14, 2017

(86) PCT No.: PCT/US2017/022365
§ 371 (c)(1),
(2) Date: Sep. 13, 2018

(87) PCT Pub. No.: WO2017/160880
PCT Pub. Date: Sep. 21, 2017

(65) Prior Publication Data
US 2019/0241958 A1 Aug. 8, 2019

Related U.S. Application Data

(60) Provisional application No. 62/308,184, filed on Mar. 14, 2016.

(51) Int. Cl.
*C12Q 1/6883* (2018.01)
*C12Q 1/6851* (2018.01)

(52) U.S. Cl.
CPC ......... *C12Q 1/6883* (2013.01); *C12Q 1/6851* (2013.01); *C12Q 2547/00* (2013.01); *C12Q 2600/158* (2013.01); *C12Q 2600/166* (2013.01); *C12Q 2600/178* (2013.01)

(58) Field of Classification Search
None
See application file for complete search history.

(56) References Cited

U.S. PATENT DOCUMENTS

| | | | |
|---|---|---|---|
| 2008/0050722 A1* | 2/2008 | Kim | C12N 15/113 435/6.11 |
| 2008/0213235 A1 | 9/2008 | Katz et al. | |
| 2013/0157365 A1 | 6/2013 | Buensuceso et al. | |
| 2013/0196875 A1 | 8/2013 | O'Brien et al. | |
| 2014/0147454 A1* | 5/2014 | Chakraborty | A61K 39/00 424/185.1 |
| 2018/0136209 A1 | 5/2018 | Lunyak et al. | |
| 2018/0161373 A1 | 6/2018 | Lunyak et al. | |

FOREIGN PATENT DOCUMENTS

| | | |
|---|---|---|
| CA | 2954245 A1 | 2/2016 |
| WO | WO-2006/128245 A1 | 12/2006 |
| WO | WO-2014/200030 A1 | 12/2014 |
| WO | WO-2017/160880 A1 | 9/2017 |

OTHER PUBLICATIONS

O'Connell et al PNAS. 2010. 107(32): 14235-14240 (Year: 2010).*
Inoue-Yokoo et al (Stem Cell Rev and Rep (2013) 9: 422-434 (Year: 2013).*
Table S1 "Microarray Results" from O'Connell et al PNAS. 2010. 107(32): 14235-14240, only Table S1 provided (Year: 2010).*
Anbazhagan, A. N. et al. "Translational repression of SLC26A3 by miR-494 in intestinal epithelial cells", Am J Physiol Gastrointest Liver Physiol. Jan. 2014; 306(2):G123-31.
Betel, D. et al. "Comprehensive modeling of microRNA targets predicts functional non-conserved and non-canonical sites," Genome Biol. 2010; 11(8):R90, 1-14.
Bilsland, A. E. et al. "MicroRNA and senescence: the senectome, integration and distributed control", Crit Rev Oncog, 2013. 18(4): 373-390.
Chen, D. et al. "miR-100 induces epithelial-mesenchymal transition but suppresses tumorigenesis, migration and invasion", PLoS Genet. Feb. 27, 2014; 10(2):e1004177, 1-14.
Chen, L. et al. "MicroRNA and aging: a novel modulator in regulating the aging network", Ageing Res Rev, 2010. 9 Suppl 1: S59-66.
Choudhery, M. S. et al. "Bone marrow derived mesenchymal stem cells from aged mice have reduced wound healing, angiogenesis, proliferation and anti-apoptosis capabilities", Cell Biol Int. Aug. 1, 2012; 36(8):747-53.
Gruber, H. E. et al. "Human adipose-derived mesenchymal stem cells: serial passaging, doubling time and cell senescence", Biotech Histochem. May 2012; 87(4):303-11.
Hackl, M. et al. "miR-17, miR-19b, miR-20a, and miR-106a are down-regulated in human aging", Aging Cell. Apr. 2010; 9(2):291-6.
Hausser, J. et al. "Identification and consequences of miRNA-target interactions—beyond repression of gene expression", Nat Rev Genet. Sep. 2014; 15(9):599-612.
International Search Report and Written Opinion for related International Application No. PCT/US2017/022365 dated Jun. 15, 2017, 12 pages.
Jun, H. S. et al. "Effect of cell senescence on the impedance measurement of adipose tissue-derived stem cells", Enzyme Microb Technol, 2013. 53(5): 302-306.
Katz, A. J. et al. "Cell surface and transcriptional characterization of human adipose-derived adherent stromal (hADAS) cells", Stem Cells. Mar. 2005; 23(3):412-23.
Kent, O. A. et al. "A small piece in the cancer puzzle: microRNAs as tumor suppressors and oncogenes", Oncogene. Oct. 9, 2006;25(46):6188-96.

(Continued)

*Primary Examiner* — Carla J Myers
(74) *Attorney, Agent, or Firm* — Cooley LLP

(57) ABSTRACT

Provided herein are methods and compositions for assessing the quality and potential of stem cells in a sample. Such methods and compositions are useful for helping to ensure the safety and quality of a population of stem cells before it is used in a subject.

11 Claims, 31 Drawing Sheets

Specification includes a Sequence Listing.

(56) References Cited

OTHER PUBLICATIONS

Khorshid, M. et al. "A biophysical miRNA-mRNA interaction model infers canonical and noncanonical targets", Nat Methods. Mar. 2013;10(3):253-5.
Kishi, S. et al. "A prospective epigenetic paradigm between cellular senescence and epithelial-mesenchymal transition in organismal development and aging", Transl Res, 2015. 165(1): 241-249.
Kretlow, J. D. et al. "Donor age and cell passage affects differentiation potential of murine bone marrow-derived stem cells", BMC Cell Biol. 2008; 9, 1-13.
Li, Z. et al. "Foxa2 and H2A.Z mediate nucleosome depletion during embryonic stem cell differentiation", Cell. Dec. 21, 2012; 151(7):1608-16.
Liu, J. et al. "Control of protein synthesis and mRNA degradation by microRNAs," Curr Opin Cell Biol. Apr. 2008; 20(2):214-21.
Marson, A. et al. "Connecting microRNA genes to the core transcriptional regulatory circuitry of embryonic stem cells", Cell, 2008. 134(3): 521-533.
Mendell, J. T. et al. "miRiad roles for the miR-17-92 cluster in development and disease", Cell. Apr. 18, 2008; 133(2):217-22.
Meseguer, S. et al. "The ROS-sensitive microRNA-9/9* controls the expression of mitochondrial tRNA-modifying enzymes and is involved in the molecular mechanism of MELAS syndrome", Hum Mol Genet. Jan. 1, 2015; 24(1):167-84.
Mitxelena, J. et al. "E2F7 regulates transcription and maturation of multiple microRNAs to restrain cell proliferation", Nucleic Acids Res. Mar. 9, 2016; 44(12):5557-5570.
Pringle, L. M. et al. "Atypical mechanism of NF-κB activation by TRE17/ubiquitin-specific protease 6 (USP6) oncogene and its requirement in tumorigenesis", Oncogene. Jul. 26, 2012; 31(30):3525-35.
Rippe, C. et al. "MicroRNA changes in human arterial endothelial cells with senescence: relation to apoptosis, eNOS and inflammation", Exp Gerontol. Jan. 2012; 47(1):45-51.
Saccone, V. et al. "HDAC-regulated myomiRs control BAF60 variant exchange and direct the functional phenotype of fibroadipogenic progenitors in dystrophic muscles", Genes Dev. Apr. 15, 2014; 28 (8):841-57.
Selbach, M. et al. "Widespread changes in protein synthesis induced by microRNAs", Nature. Sep. 4, 2008; 455(7209):58-63.
Sepulveda, J. C. et al. "Cell senescence abrogates the therapeutic potential of human mesenchymal stem cells in the lethal endotoxemia model", Stem Cells. Jul. 2014; 32(7):1865-77.
Sethupathy, P. et al. "A guide through present computational approaches for the identification of mammalian microRNA targets", Nat Methods. Nov. 2006; 3(11):881-6.
Shyh-Chang, N. et al. "Stem cell metabolism in tissue development and aging", Development. Jun. 2013; 140(12):2535-47.
Stefani, G. et al. "Small non-coding RNAs in animal development", Nat Rev Mol Cell Biol. Mar. 2008; 9(3):219-30.
Sun, D. et al. "miR-99 Family of MicroRNAs Suppresses the Expression of Prostate-Specific Antigen and Prostate Cancer Cell Proliferation", Cancer Res. Feb. 15, 2011; 71(4):1313-24.
Szklarczyk, D. et al. "The STRING database in 2011: functional interaction networks of proteins, globally integrated and scored", Nucleic Acids Res. Jan. 2011;39(Database issue):D561-8.
Talkowski, M. E. et al. "Sequencing chromosomal abnormalities reveals neurodevelopmental loci that confer risk across diagnostic boundaries", Cell. Apr. 27, 2012; 149(3):525-37.
Tarazona, S. et al. "Differential expression in RNA-seq: a matter of depth", Genome Res. Dec. 2011; 21(12):2213-23.
Tollervey, J.R. et al. "Adult stem cells: simply a tool for regenerative medicine or an additional piece in the puzzle of human aging?", Cell Cycle. Dec. 15, 2011; 10(24):4173-6.
Von Mering, C. et al. "STRING: known and predicted protein-protein associations, integrated and transferred across organisms", Nucleic Acids Res. Jan. 1, 2005; 33(Database issue):D433-7.
Wang, J. et al. "Inhibition of activated pericentromeric SINE/Alu repeat transcription in senescent human adult stem cells reinstates self-renewal", Cell Cycle. Sep. 1, 2011; 10(17):3016-30.
Wang, W. et al. "Diversity and specialization of mammalian SWI/SNF complexes," Genes Dev. Sep. 1, 1996; 10(17):2117-30.
Weber, J. A. et al. "The microRNA spectrum in 12 body fluids", Clin Chem, 2010. 56(11): 1733-1741.
Winter, J. et al. "Loop-miRs: active microRNAs generated from single-stranded loop regions", Nucleic Acids Res. May 2013; 41(10): 5503-5512.
Ye, Y. et al. "TRE17/USP6 oncogene translocated in aneurysmal bone cyst induces matrix metalloproteinase production via activation of NF-kappaB", Oncogene. Jun. 24, 2010; 29(25):3619-29.
Zuk, P. A. et al. "Human adipose tissue is a source of multipotent stem cells", Mol Biol Cell. Dec. 2002; 13(12):4279-95.

\* cited by examiner

FIG. 5B

| Chrom. | Loc. Start | Loc. End | Loc. Name | microRNA |
|---|---|---|---|---|
| chr11 | 64946845 | 64950579 | Neat-1 | mir-612 |
| chr11 | 121465021 | 121578980 | MIR100HG | mir-125b-1<br>let-7a-2<br>mir-100 |
| chr13 | 90798075 | 90804830 | MIR17HG | mir-17<br>mir-18a<br>mir-19a<br>mir-20a<br>mir-19b-1<br>mir-92a-1 |
| chr22 | 44860541 | 44888472 | MIRIET7BHG | mir-3619<br>let-7a-3<br>mir-4763<br>let-7b |

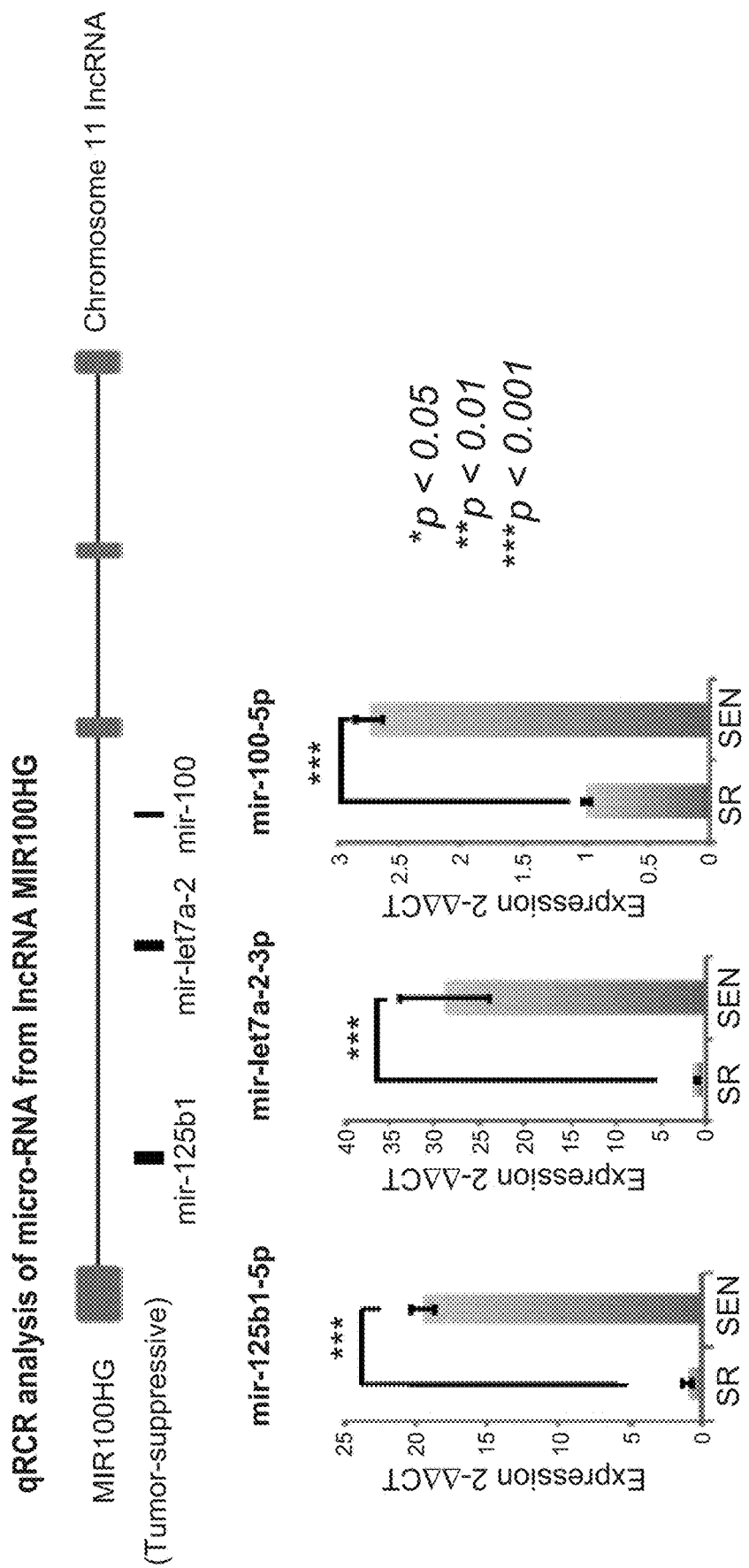

6A qRCR analysis of microRNA

6B

Protein Level

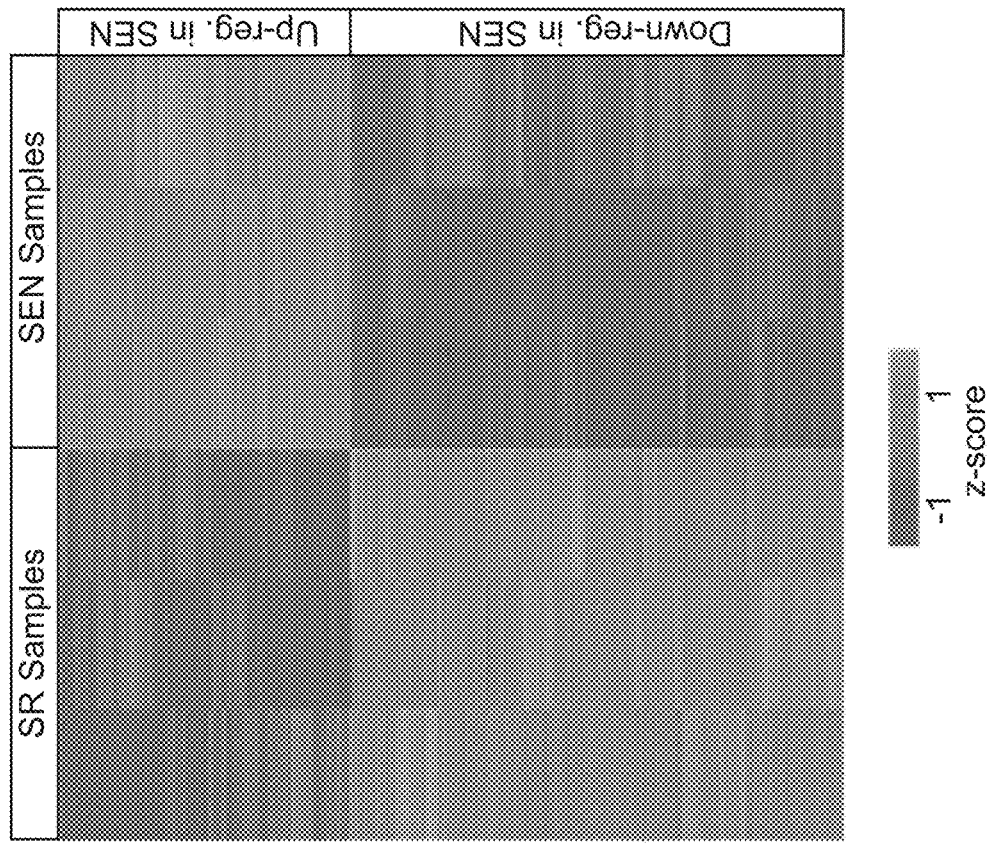

Euclidean Distance (D)

TRANSLATIONAL REPRESSION

COMPOSITIONS AND METHODS FOR THE QUALITY CONTROL OF STEM CELL PREPARATIONS

CROSS-REFERENCE TO RELATED APPLICATIONS

This application is a U.S. National Stage Application under 35 U.S.C. § 371 of International Application No. PCT/US2017/022365, filed on Mar. 14, 2017, which claims the priority benefit of U.S. Provisional Patent Application Ser. No. 62/308,184, filed on Mar. 14, 2016, each of which is hereby incorporated by reference in its entirety.

DESCRIPTION OF THE TEXT FILE SUBMITTED ELECTRONICALLY

The contents of the text file submitted electronically herewith are incorporated herein by reference in their entireties: A computer readable format copy of the Sequence Listing (filename: ALNC_005_01US_SeqList_ST25.txt, date recorded Mar. 4, 2019, file size ~2 kilobytes).

BACKGROUND OF THE INVENTION

Adult stem cells, for example, mesenchymal stem cells (MSCs), generate the differentiated cell types within many organs throughout the lifespan of an organism and are thus ultimately responsible for the longevity of multicellular organisms. Stem cells possess three important properties: (1) they self-renew, allowing the maintenance of the original stem cell population; (2) they differentiate into multiple types of mature cells in order to replace the mature cells that turn over in adult tissues; and (3) they maintain the stability of a stable stem cell pool (Tollervey and Lunyak, 2011). Utilizing these properties in the clinical setting, stem cell-based therapies have, for example, been shown to: restore neuronal integrity by stimulating the release of neurotrophic factors by neighboring cells, prevent cognitive decline caused by aging, facilitate nerve recovery after injury both in the CNS and in the periphery; stimulate remyelination processes and glial regenerative support to neurons; prevent retinal damage and maintain retinal barrier properties; and impede oxidative insults.

The properties of stem cells influence a broad spectrum of physiological events that are negatively impacted by cellular senescence, a Mate in which a cell no longer has the ability to proliferate (stem cell exhaustion). Senescence involves signaling, metabolic, and cytoskeletal changes resulting in the diminished ability of cells to cope with DNA damage and to maintain the structure and function of chromatin (Katz, Tholpady et al. 2005, Shyh-Chang, Daley et al. 2013). Cellular senescence is associated with changes in gene expression (Hackl, Burnner et al. 2010; Rippe, Blimline et al., 2012) and can influence the maintenance and function of transplanted stem cells in therapeutic applications (Sepulveda J C, Stem cells, 2014). For example, senescent mesenchymal stem cells (MSCs) have an impaired migratory capacity in response to pro-inflammatory signals and do not produce a therapeutic effect in many clinical trials. Furthermore, there is evidence for a negative correlation between donor age and the proliferative and regenerative capacity of MSCs (Kretlow et al., 2008; Choudhery et al., 2012).

Isolated and ex-vivo cultured human adipose-derived stem cells exhibit consistent self-renewing (SR) and, upon approaching replicative senescence (SEN), cultures accumulate giant non-dividing cells expressing the enzyme lysosomal pH6 senescence-associated β-galactosidase (SA-βgal). This can manifest in the loss of control for chromatin organization and the activation of a persistent DNA damage response (DDR), and can cause robust changes in transcriptional activity (Wang, Geesman et al. 2011, Gruber, Somayaji et al. 2012, June, Dao et al. 2013).

Senescent cells would likely not be productive, and could be detrimental if used in stem cell-based therapies. Thus, it may be advantageous to characterize stem cells before they are used in a subject. The inventions described herein provide methods and related compositions for ensuring that stem cells meet the necessary requirements for safety and quality before they are used clinically.

BRIEF SUMMARY OF THE INVENTION

Provided herein are methods and compositions for assessing the quality and potential of stem cells in a sample. Such methods and compositions are useful for helping to ensure the safety and quality of a population of stem cells before it is used in a subject.

In one aspect, provided herein is a method of assessing the quality of stem cells in a sample, comprising: (a) measuring the expression level of at least one RNA in the sample; (b) comparing the expression level of at the at least one RNA to a reference standard; and (c) using the comparison to determine the quality of stem cells in the sample. The measuring of the expression level of the at least one RNA may involve determining the quantity of unproductive stem cells in the sample. In some cases, the unproductive stem cells are not self-renewing. The method is applicable to stem cells from any organism or tissue. For example the quality of human stem cells, mesenchymal stem cells, or adipose-derived mesenchymal stem cells may be assessed by this method. The method may utilize a wide variety of samples. For example, the sample used for the quality assessment may comprise adipose tissue, for example adipose tissue that is ultimately used for transplantation. The sample used for the quality assessment may comprise a stromal vascular fraction, pericytes, mesodermal tissue differentiated from induced pluripotent stem cells, or bone marrow-derived stem cells. In practicing the method, the measuring of the expression level of the at least one RNA may comprise using qPCR. An increase in the expression level of particular RNAs, as measured by this method, may be correlated with an increase in the quantity of unproductive stem cells in the sample. Alternatively, a decrease in the expression level of particular RNAs, as measured by this method may be correlated with an increase in the quantity of unproductive stem cells in the sample. In some embodiments, the expression level of the RNA is increased by at least 2-fold. In some embodiments, the expression level of the RNA is decreased by at least 2-fold. In some embodiments of the method, the at least one RNA in the sample comprises a coding RNA, whereas in other embodiments, the at least one RNA in the sample comprises a non-coding RNA (ncRNA). In some embodiments, the ncRNA is a microRNA (miRNA). In some embodiments, the miRNA is transcribed from the chr11: MIR100f1t1 locus, the chr13:MIR17HG locus, or the chr221:MIRLET7BHG locus of the human chromosome. In some embodiments, the miRNA is selected from the group consisting of mir-125b1, mir-let7a-2, mir-100, mir-17, mir-18a, mir-19a, mir-20a, mir-19b-1, mir-92a-1, mir-3619, mir-let7a-3, mir-4763, and mir-let-7b. In some embodiments, the at least one RNA encodes for a SUZ12, NAP1L1, SMARCD2, SAP18, IGF2BP3, CHD2, CHD4, SMARCA1, CHD8, HDAC3, HDAC5, HDAC9 or USP6/TRE17 protein. The method can further comprise separating the unproductive stem cells from the sample, for example discarding the sample if >10% of the cells in the sample are unproductive stem cells.

In another aspect, provided herein is a kit for assessing the quality of stem cells in a sample, comprising reagents for measuring the expression level of at least one RNA in the sample. Such reagents may useful for measuring the expression level of at least one non-coding RNA (ncRNA) in the sample, and/or for measuring the expression level of at least one coding RNA in the sample. In some embodiments, the reagents are for measuring the expression level of at least one microRNA (miRNA) in the sample. In some embodiments, the miRNA is selected from the group consisting of mir-125b1, mir-let7a-2, mir-100, mir-17, mir-18a, mir-19a, mir-20a, mir-19b-1, mir-92a-1, mir-3619, mir-4763, and mir-let-7b. The kit may further comprise reagents for separating unproductive stem cells from the sample.

BRIEF DESCRIPTION OF THE DRAWINGS

FIG. 2A shows FACS analysis of hADSCs. FIG. 2B shows a representative transcriptional analysis of CD105, CD 44 and β-actin gene transcription by RNA-seq.

FIG. 3A is a schematic illustrating the proteomic analysis workflow and the approach used to quantify and normalize protein expression levels based on the LC-MS/MS proteome profiling. FIG. 3B is a distribution of normalized protein expression levels.

FIGS. 5B, 5C and 5D depict senescent-associated miRNAs (SA-miRNAs) and clusters discovered via RNA-seq analysis and experimentally validated with qPCR.

FIGS. 7A-D depict differential expression of mRNA and protein targets of SA-miRNAs.

DETAILED DESCRIPTION OF THE INVENTION

Figure 1:
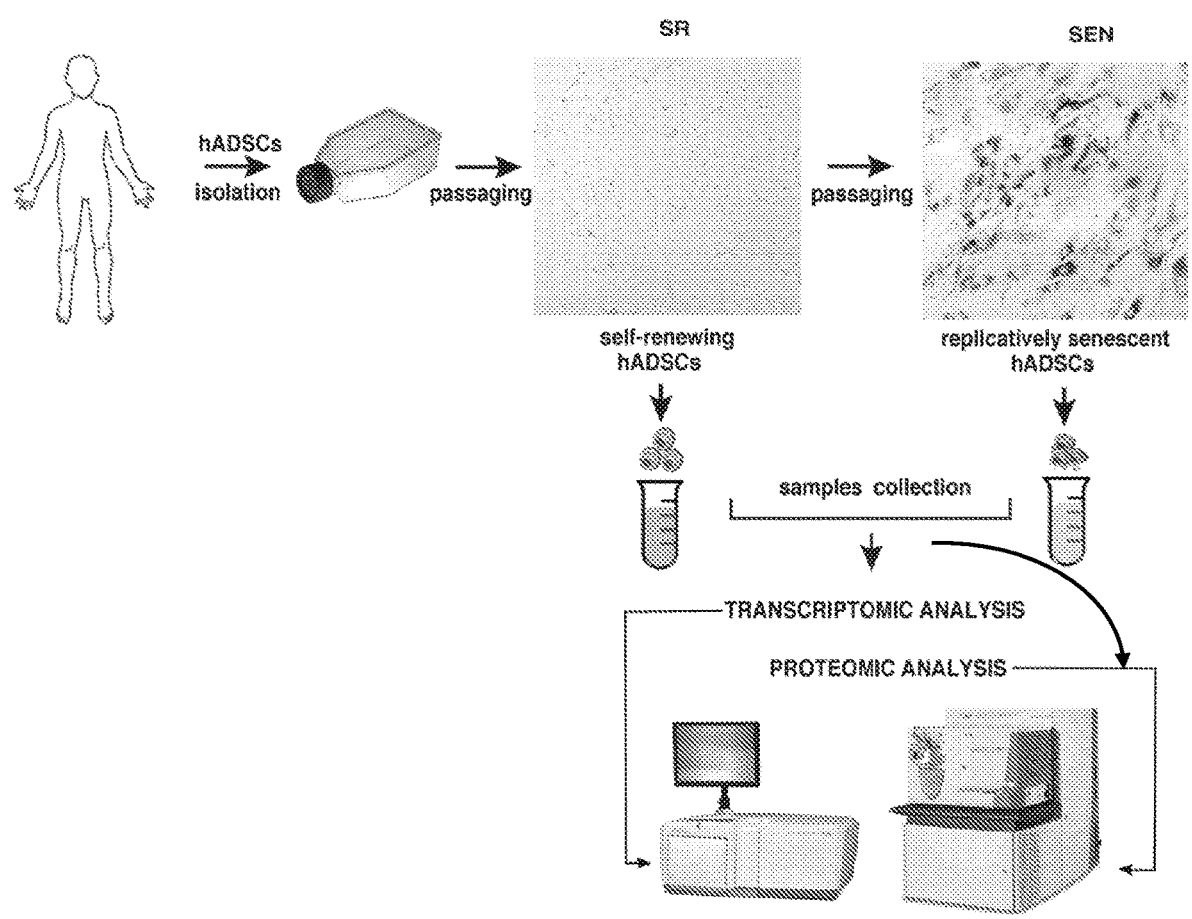
FIG. 1 depicts a schematic representation of sample collection and analysis of hADSCs upon replicative senescence.

Provided are methods and compositions for assessing the quality and potential of stem cells in a sample. Such methods and compositions are useful for helping to ensure the safety and quality of a population of stem cells before it is used in a subject.

Samples and Stem Cells

Methods and compositions to assess the quality of stem cells are applicable to samples comprising stem cells, of any origin, from any mammalian organism.

The quality assessment may be carried out on any type of sample. For example, blood or tissue samples are representative of samples which could require a quality assessment prior to downstream use.

In some embodiments, the sample being assessed for quality comprises blood, for example prior to a transfusion or extraction of stem cells. In some embodiments, the sample comprises bone marrow cells, and the resident bone marrow stromal stem cells are assessed for quality. In some embodiments, the sample comprises pericytes.

In some embodiments, the sample being assessed for quality comprises a tissue. Such tissue may require assessment prior to a procedure, for example, prior to transplantation, implantation or graft. The tissue can be from any region or organ of the body. In an exemplary embodiment, the tissue comprises an adipose tissue for transplantation. In a particular example, the sample comprises a stromal vascular fraction from an adipose tissue. In some embodiments, the sample comprises differentiated tissue which requires assessment prior to downstream use. For example, the sample may comprise mesodermal tissue differentiated from induced pluripotent stem cells.

The quality assessment may also be carried out on a sample of cell or tissue culture media, comprising stem cells. The quality of the stem cells may indicate the need to change or replenish the media.

These samples discussed above may comprise any type of mammalian stem cell, and accordingly, a wide variety of stem cells can be assessed for quality. In some embodiments, the sample comprises human stem cells. In some embodiments, the sample comprises non-human primate stem cells. In some embodiments, the sample comprises canine stem cells. In some embodiments, the sample comprises feline stem cells. In some embodiments, the sample comprises rodent stem cells. In some embodiments, the sample comprises murine stem cells. In some embodiments, the sample comprises bovine stem cells.

The sample can comprise any type of stem cell, of any origin. In some embodiments, the sample comprises mesenchymal stem cells. In some embodiments, the sample comprises adipose-derived stem cells. In some embodiments, the sample comprises adipose-derived mesenchymal stem cells. In some embodiments, the sample comprises bone marrow-derived stem cells. In some embodiments, the sample comprises bone marrow-derived mesenchymal stem cells. In some embodiments, the sample comprises cancer stem cells.

Stem Cell Quality

Provided herein are methods and compositions for assessing the quality of stem cells in a sample. In some embodiments the assessing comprises determining the quantity of productive and/or unproductive stem cells in the sample.

Productive stem cells are those that meet a certain threshold for quality and safety. Productive stem cells exhibit one or more of the following features associated with being productive: express a set of coding or non-coding RNAs indicative of quality; are self-renewing; are not senescent; are not nearing senescence; have been passaged 6 times or less; exhibit high growth potential; produce proteins of interest; allow for long-term tissue regeneration; induce long-term correction of a disease; exhibit no or only a low chance of immortalization; exhibit no or low tumorigenic potential; and contain few or no proviral integrations. In an exemplary embodiment, productive stem cells are self-renewing. In some embodiments, productive stem cells exhibit at least two, three, four, five, or more of the features associated with being productive.

In contrast, unproductive stem cells are those that do not meet a certain threshold for quality and safety. Unproductive stem cells exhibit one or more of the following features associated with being unproductive: express a set of coding or non-coding RNAs indicative of their low quality; are not or are minimally self-renewing; are senescent or are nearing senescence; have been passaged greater than 6 times; exhibit low or no growth potential; do not or only minimally produce proteins of interest; do not or only minimally allow for long-term tissue regeneration; do not or only minimally induce long-term correction of a disease; exhibit tumorigenic potential; or contain proviral integrations. In an exemplary embodiment, unproductive stem cells are not self-renewing. In some embodiments, unproductive stem cells exhibit at least two, three, four, five, or more of the features associated with being unproductive.

Methods and RNAs of the Invention

Provided herein are methods for assessing the quality of stem cells in a sample, for example in vitro or ex vivo. In some embodiments, the method comprises: (a) measuring the expression level of at least one RNA in the sample; (b) comparing the expression level of at the at least one RNA to a reference standard; and (c) using the comparison to determine the quality of stem cells in the sample. In some embodiments the assessing comprises determining the quantity of productive and/or unproductive stem cells in the sample.

In some embodiments, an increase in the expression level of the RNA compared to the reference standard is correlated with an increase in the quality of the stem cells in the sample and the quantity of productive stem cells in the sample. In specific embodiments, the expression level of the RNA is increased by at least 2-fold, at least 3-fold, at least 4-fold, at least 5-fold, at least 6-fold, at least 7-fold, at least 8-fold, at least 9-fold, at least 10-fold, at least 15-fold, at least 20-fold, at least 25-fold, at least 50-fold, or at least 100-fold.

In some embodiments, a decrease in the expression level of the RNA compared to the reference standard is correlated with an increase in the quality of the stem cells in the sample and the quantity of productive stem cells in the sample. In specific embodiments, the expression level of the RNA is decreased by at least 2-fold, at least 3-fold, at least 4-fold, at least 5-fold, at least 6-fold, at least 7-fold, at least 8-fold, at least 9-fold, at least 10-fold, at least 15-fold, at least 20-fold, at least 25-fold, at least 50-fold, or at least 100-fold.

In some embodiments, an increase in the expression level of the RNA compared to the reference standard is correlated with a decrease in the quality of the stem cells in the sample and the quantity of unproductive stem cells in the sample. In specific embodiments, the expression level of the RNA is increased by at least 2-fold, at least 3-fold, at least 4-fold, at least 5-fold, at least 6-fold, at least 7-fold, at least 8-fold, at least 9-fold, at least 10-fold, at least 15-fold, at least 20-fold, at least 25-fold, at least 50-fold, or at least 100-fold.

In some embodiments, a decrease in the expression level of the RNA compared to the reference standard is correlated with a decrease in the quality of the stem cells in the sample and the quantity of unproductive stem cells in the sample. In specific embodiments, the expression level of the RNA is increased by at least 2-fold, at least 3-fold, at least 4-fold, at least 5-fold, at least 6-fold, at least 7-fold, at least 8-fold, at least 9-fold, at least 10-fold, at least 15-fold, at least 20-fold, at least 25-fold, at least 50-fold, or at least 100-fold.

The measurement of the expression level of the RNA in the sample can be carried out by any means known to those skill in the art, including, but not limited to, qPCR, Northern Blot, RNA-sequencing, and in situ-hybridization.

In some embodiments of the invention, the method for assessing the quality of stem cells in a sample comprises: (a) measuring the expression level of at least one coding RNA (a RNA molecule that can be translated into a protein) in the sample; (b) comparing the expression level of at the at least one coding RNA to a reference standard; and (c) using the comparison to determine the quality of stem cells in the sample. In some embodiments, the expression of the coding RNA is upregulated in unproductive stem cells or senescent stem cells. In some embodiments, the expression of the coding RNA is downregulated in unproductive stem cells or senescent stem cells. In particular embodiments, RNA encoding SUZ12, NAP1L1, SMARCD2, SAP18, IGF2BP3, CHD2, CHDR4, SMARCA1, CHD8, HDAC3, HDAC5, HDAC9 or USP6/TRE17 protein is downregulated in unproductive stem cells or senescent stem cells. In one exemplary embodiment, RNA encoding a NAP1L1 protein is downregulated in unproductive stem cells or senescent stem cells. In another exemplary embodiment, RNA encoding a SMARCD2protein is downregulated in unproductive stem cells or senescent stem cells. In another exemplary embodiment, RNA encoding a USP6/TRE17 protein is downregulated in unproductive stem cells or senescent stem cells.

In some embodiments of the invention, the method for assessing the quality of stem cells in a sample comprises: (a) measuring the expression level of at least one non-coding RNA (ncRNA; a RNA molecule that is not translated into a protein) in the sample; (b) comparing the expression level of at the at least one ncRNA to a reference standard; and (c) using the comparison to determine the quality of stem cells in the sample. Non coding RNAs of the invention, include but are not limited to microRNA (miRNA), piwi-interacting RNA (piRNA), small interfering RNA (siRNA), long non-coding RNA (lncRNA), enhancer RNA (eRNA), and promoter-associated RNA (PAR). In some embodiments, the expression of the ncRNA is upregulated in unproductive stem cells or senescent stem cells. In some embodiments, the expression of the ncRNA is downregulated in unproductive stem cells or senescent stem cells.

In some embodiments, the method for assessing the quality of stem cells in a sample comprises measuring the expression level of at least one microRNA (miRNA). miRNAs are single-stranded RNA molecules, and are a type of ncRNA. miRNA is not translate into protein, but can regulate the expression of one or more genes. Typically, miRNAs target particular mRNAs, or groups of mRNAs, thereby preventing their translation (translational repression), or inducing their degradation (mRNA cleavage) or by inducing deadenylation. In particular embodiments of the invention, the method for assessing the quality of stem cells in a sample comprises: (a) measuring the expression level of at least one miRNA in the sample; (b) comparing the expression level of at the at least one miRNA to a reference standard; and (c) using the comparison to determine the quality of stem cells in the sample. In some embodiments, the miRNA is a senescence-associated microRNA (SA-miRNA).

In the embodiments where the expression level of a miRNA, compared to the reference standard, is correlated with the quality of the stem cells, the miRNA may be transcribed from a chromosome locus that is an oncogenic locus. Alternatively, the miRNA may be transcribed from a chromosome locus that a tumor-suppressive locus. In specific embodiments, the miRNA is transcribed from the chr11:MIR100HG locus, the chr13:MIR17HG locus, or the chr221:MIRLET7BHG locus of the human chromosome.

In some embodiments, the expression level of a miRNA is increased in unproductive stem cells or senescent stem cells. In such embodiments, the miRNA may be selected from the group consisting of mir-125b1, mir-let7a-2, mir-100, mir-17, mir-18a, mir-19a, mir-20a, mir-19b-1, mir-92a-1, mir-3619, mir-let7a-3, mir-4763, and mir-let-7b. Alternatively, in some embodiments, the expression level of a miRNA is decreased in unproductive stem cells or senescent stem cells.

During miRNA biogenesis, miRNA is initially double stranded, comprising a guide strand and a passenger strand. In some embodiments of the invention presented herein, whether or not a stem cell is marked as productive or unproductive may be associated with a shift in a miRNA's maturation equilibrium between its guide and passenger strands. Thus, in some embodiments of the invention, the method for assessing the quality of stem cells in a sample comprises: (a) measuring the expression level of at least one non-coding miRNA in the sample; (b) assessing if there is a shift in the miRNA's maturation equilibrium between its guide and passenger strands, as compared to a reference standard; and (c) using the comparison to determine the quality of stem cells in the sample.

Thus, as provided herein, a cell marked as unproductive or senescent may be associated with the increased expression of the mature guide strand of a miRNA, with the increased expression of the mature passenger strand of a miRNA, with the decreased expression of the mature guide strand of a miRNA, or with the decreased expression of the mature passenger strand of a miRNA.

Additionally, as provided herein, the self renewing capacity of a cell may be associated with the increased expression of the mature guide strand of a miRNA, with the increased expression of the mature passenger strand of a miRNA, with the decreased expression of the mature guide strand of a miRNA, or with the decreased expression of the mature passenger strand of a miRNA.

In some embodiments of the invention, the method for assessing the quality of stem cells in a sample comprises: (a) measuring the expression level of at least one ncRNA in the sample, and measuring at least one coding RNA in the sample; (b) comparing the expression level of at the at least one ncRNA and the at least one coding RNA to a reference standard; and (c) using the comparison to determine the quality of stem cells in the sample. Thus in some embodiments, the expression levels of both coding and ncRNA are measured.

In an exemplary embodiment, senescence of human adipose derived stem cells correlates with an upregulation of the subset of mature miRNAs from the MIR100HG and MIR17HG cluster. In another exemplary embodiment, senescence of human adipose derived stem cells correlates with a shift in the equilibrium between guide and passenger strands for mir-let7a-2 (FIGS. 5D and 6A).

In the methods provided herein, the expression level of the least one RNA is compared to a reference standard. The reference standard may be coding RNA profiles or ncRNA (e.g. miRNA) profiles from an isolated cell, cell derived from a cell culture, cell line, or stored cell preparation. The reference standard may comprise profiles derived from single cell types, or a plurality of different cell types. Generally, the reference standard is obtained from a cell or cells exhibiting known characteristics, which meet a certain predetermined quality. For example the reference standard may be a self renewing cell, or a population of self renewing cells. Or, the reference standard may be a unproductive or senescent cell, or a population of unproductive or senescent cells.

Applications

Stem cells exhibit consistent self-renewing (SR) but, upon approaching replicative senescence (SEN), exhibit one or more of the following features associated with being unproductive: express a set of coding or non-coding RNAs indicative of their low quality; are not or are minimally self-renewing; are senescent or are nearing senescence; have been passaged greater than 6 times; exhibit low or no growth potential; do not or only minimally produce proteins of interest; do not or only minimally allow for long-term tissue regeneration; do not or only minimally induce long-term correction of a disease; exhibit tumorigenic potential; or contain proviral integrations. Unproductive and senescent cells would likely not be productive, and could be detrimental if used in stem cell-based therapies. Thus provided herein are methods and compositions that would be useful for helping to ensure the safety and quality of a population of stem cells before it is used in a subject.

In ensuring the safety and quality of a population of stem cells, the method and compositions provided herein find many clinical applications. Such application include, but are not limited to (1) helping to evaluate the therapeutic potential of stem cells for various clinical applications; (2) screening a population of stem cells prior to bio-banking those stem cells for future uses; (3) assessing the rate of cellular senescence in the stem cells, prior to use in clinical applications, for example for regenerative cell therapies; (4) estimating the yield of viable stem cells from donor tissue; (5) assessing the microenvironment, cell culture media conditions or tissue culture media conditions that can yield sufficient number of productive stem cells; and (6) assessing the rate of cellular senescence in the stem cells for clinical applications and estimate yielding of viable stem cells from donor tissue to procure clinical benefits.

In some embodiments, the method further comprises separating the unproductive stem cells from a sample, for example prior to bio-banking or treatment of a subject. For example, unproductive stem cells can be FACs sorted from productive stem cells, by using magnetic beads technology, differential attachment assays, visual morphological inspections, or differential migration assays.

In some embodiments, a sample comprising stem cells is enriched or purified for productive stem cells by sorting productive cells from unproductive cells, or by sorting self renewing stem cells from senescent stem cells. In some embodiments, a sample is enriched or purified such that 50, 55, 60, 65, 70, 75, 80, 85, 90, 95, 96, 97, 98, 99, or 100% cells in the sample are the type being selected for. In some cases, the cell population is enriched 2×, 3×, 4×, 5×, 6×, 7×, 8×, 9×, 10× or more (or any range derivable therein).

In specific embodiments, purifying or enriching comprises incubating a β-galactosidase substrate with cells and selecting for β-galactosidase activity. In some cases, β-galactosidase activity is detectable upon cleavage of the β-galactosidase substrate by βgalactosidase. A label or other detectable moiety may be employed for evaluating whether a cell is entering into senescence or for sorting, separating, or selecting senescent cells and non-senescent cells. In particular embodiments, β-galactosidase activity is detectable by fluorescence. In some cases, a substrate of β-galactosidase is employed and the enzymatic product is detectable, such as by fluorescence.

In some embodiments unproductive/senescent or productive/self-renewing cells in a sample can be visualized. Visualization can be achieved, for example by in situ hybridization, using labeled probes targeted to specific RNAs, for example labeled probes targeted to miRNAs of interest.

In some embodiments, the method further comprises discarding the sample if greater than 10% of the cells in the sample comprise unproductive or senescent stem cells. In related embodiments, the method further comprises discarding the sample if greater than 15%, greater than 20%, greater than 25%, greater than 30%, greater than 35%, greater than 40%, greater than 45%, greater than 50%, greater than 55%, greater than 60%, greater than 65%, greater than 70%, greater than 75%, greater than 80%, greater than 85% of the cells in the sample comprise unproductive or senescent stem cells.

Identification of Candidate RNAs

Presented herein are methods and compositions that aid in the identification of candidate coding RNAs or non coding RNAs (ncRNAs) useful for determining the quality of stem cells in a sample. In connection with the invention, upon identification of candidate coding RNAs or ncRNAs and subsequent validation of the same, the quality of stem cells in a sample may be assessed, comprising (a) measuring the expression level of at least one RNA in the sample; (b) comparing the expression level of at the at least one RNA to a reference standard; and (c) using the comparison to determine the quality of stem cells in the sample.

Analysis of expression levels, to differentiate between productive and unproductive cells, or to differentiate between self-renewing (SR) and senescent (SEN) cells, may be carried out using any technique familiar to those with skill in the art. For example, methods involving proteomic analysis, transcriptome analysis, and/or RNA-sequencing (RNA-seq) may be utilized to characterize differential RNA expression levels between unproductive and productive cells, or between SR and SEND cells.

One exemplary approach to carry out the analysis of differential gene expression levels between SR and SEN cells comprises employing a combination of two-parameters in order to define differential expression levels between genes: 1) the difference in the number reads per kilobase per million mapped reads (dRPKM) and 2) the expression fold-change (FC) level. This approach controls for liabilities of each individual metric; in particular, dRPKM is biased towards highly expressed genes, whereas FC is biased towards lowly expressed genes. In this approach, dRPKM can be defined as: $RPKM_{SR}-RPKM_{SEN}$, and FC can be defined as: $\log_2 RPKM_{SR}/RPKM_{SEN}$. For each locus, dRPKM and FC are plotted as a point in two-dimensional Euclidean space, and the Euclidean Distance (D) between the origin and the point is taken to represent the differential expression level. This approach can be used separately to evaluate the differential expression of mRNAs and non-coding RNAs, including miRNAs, which are typically expressed at lower levels. In some embodiments, for non-coding RNAs, differentially expressed genes are considered as those with |FC|>0.95 and |dRPKM|>4.07, and for mRNAs differentially expressed genes are considered as those with |FC|>0.58 and |dRPKM|>2.32.

The set of genes that characterized as both targets of SEN upregulated miRNAs and found to be downregulated in SEN stem cells can be further analyzed for functional relevance. Proteins from annotation categories of interest—cell cycle, chromatin, transcription/translation and histone methyltransferases—can be selected for functional enrichment analysis using a network-based approach.

Kits

The present application also provides kits for assessing the quality of stem cells in a sample and determining the quantity of unproductive stem cells in a sample. In some embodiments, the kits comprise reagents for measuring the expression level of at least one RNA in the sample. In some embodiments, the kits comprise reagents for measuring the expression level of at least one coding RNA in the sample. In some embodiments, the kits comprise reagents for measuring the expression level of at least one ncRNA in the sample. In some embodiments, the kits comprise reagents for measuring the expression level of both at least one coding RNA and at least one ncRNA in the sample. In some embodiments, the kit comprises reagents for assessing the expression level of a miRNA selected from the group consisting of mir-125b1, mir-let7a-2, mir-100, mir-17, mir-18a, mir-19a, mir-20a, mir-19b-1, mir-92a-1, mir-3619, mir-let7a-3, mir-4763, and mir-let-7b. In some embodiments, the kit further comprises reagents for separating unproductive stem cells from the sample.

The present application also provides articles of manufacture comprising any one of the compositions or kits described herein.

It is to be understood that the terminology employed herein is used for the purpose of describing particular embodiments only and is not intended to be limiting since the scope of the present invention will be limited only by the appended claims and equivalents thereof. The following examples are for illustrative purposes. These are intended to show certain aspects and embodiments of the present invention but are not intended to limit the invention in any manner.

EXAMPLES

Example 1: Replicative Senescence of Human Adult Adipose-Derived Stem Cells is Associated with Changes in Expression This example shows differential gene expression in SR and SEN cells.

Isolation and Culture of hADSCs

Human adipose derived stem cells (hADSCs) were isolated from human subcutaneous white adipose tissue collected during liposuction procedures. The lipoaspirate was suspended in Hank's Buffered Salt Solution (HBSS, Life technology), 3.5% Bovine Serum Albumin (BSA, Sigma), 1% Collagenase Type II (Sigma) in 1:3 w/v ratio and shaken at 37° C. for 50 min. The cells were filtered through a 70 μm mesh cell strainer (BD Falcon #352350), treated with Red Blood Cell Lysis buffer (150 mM NH4Cl, 10 mM KHCO$_3$, 0.1 mM EDTA, pH 7.3), and expanded ex vivo in DMEM/F12 complete medium (DMEM/F12, 10% FBS, 100 U/ml penicillin, 100 μg/ml streptomycin; Life technology) in 10% CO$_2$ at 37° C. and passaged at 80% confluency, changing medium every 72-96 h. Cumulative population doublings were calculated by summing the population doublings (PD=log$_{(N,N0)}$×3.33, where N0 is the number of cells plated in the flask and N is the number of cells harvested at this passage) across multiple passages as a function of the number of days it was grown in culture.

Senescence-Associated Beta-Galactosidase (SA β-gal) Staining

The SA-βgal activity assay was performed according to manufacturer's instructions (BioVision). The cells were washed with PBS and fixed with fixation solution for 15 min at room temperature. The cells were washed with PBS twice and X-gal staining solution was added with a staining supplement per well and incubated overnight at 37° C. The cells were washed twice with PBS, and the images were captured using a microscope (Nikon, TE300, DXM1200 Digital Camera, Japan).

As depicted in FIG. 1, hADSCs were isolated from healthy donor subcutaneous tissue and passaged ex-vivo as described above. Detection of senescence-associated β-galactosidase (10×) in self-renewing (SR) and senescent (SEN) hADSCs is shown. Samples were collected and processed for either transcriptomic or proteomic studies as described below.

Surface Marker Characterization

Surface CD antigen markers of SEN hADSCs were characterized. 5×10$^5$ cells each were incubated for 30 min on ice in the dark with fluorochrome-conjugated antibodies (CD31, CD44, CD45 and CD105; Invitrogen) in PBS with 1% BSA (Sigma), washed and analyzed in a Guava EasyCyte Mini System (Guava Technologies, Millipore). Data analysis was done with FlowJo software (Tree Star, Ashland, Oreg.). CD antigen marker characterization revealed that SEN hADSCs express stromal markers CD29, CD44, CD73, CD90, CD105 while staying negative for hematopoietic lineage markers CD31, CD34 and CD45 (Zuk, Zhu et al. 2002), indicating phenotypical stability of SEN hADSCs (Table 1, FIG. 2). Table 1 summarizes the immunostability of hADSCs in SR and SEN states.

TABLE 1

Immunostability of hADSCs in SR and SEN States

| Chromosome | Gene | Expression | |
|---|---|---|---|
| | | SR | SEN |
| Negative Markers | | | |
| 16 | CD 11b | – | – |
| 5 | CD 14 | – | – |
| 17 | CD 31 | – | – |
| 1 | CD 34 | – | – |
| 1 | CD 45 | – | – |
| 1 | CD 106 | – | – |
| 4 | ABC G2 | – | – |
| 3 | CD 10 | + | + |
| 2 | CD 49d | + | + |
| Stromal Markers | | | |
| 15 | CD 13 | ++ | ++ |
| 10 | CD 29 | ++ | ++ |
| 11 | CD 44 | ++ | ++ |
| 6 | CD 73 | ++ | ++ |
| 11 | CD 90 | ++ | ++ |
| 9 | CD 105 | + | ++ |
| 3 | CD 166 | ++ | ++ |

Figure 2A:
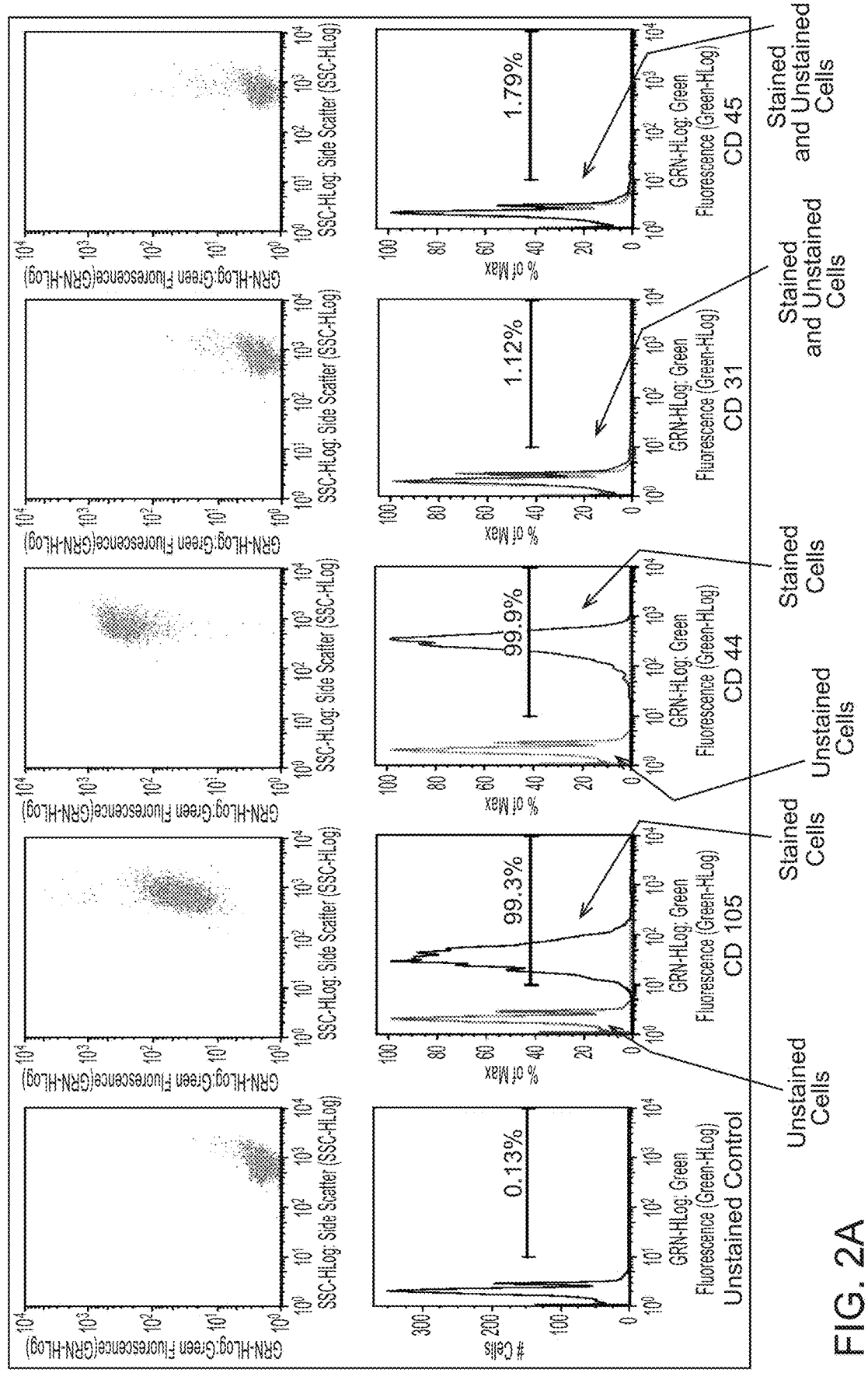
FIGS. 2A and 2B depict immunophenotypes of hADSCs upon senescence.
Figure 2B:
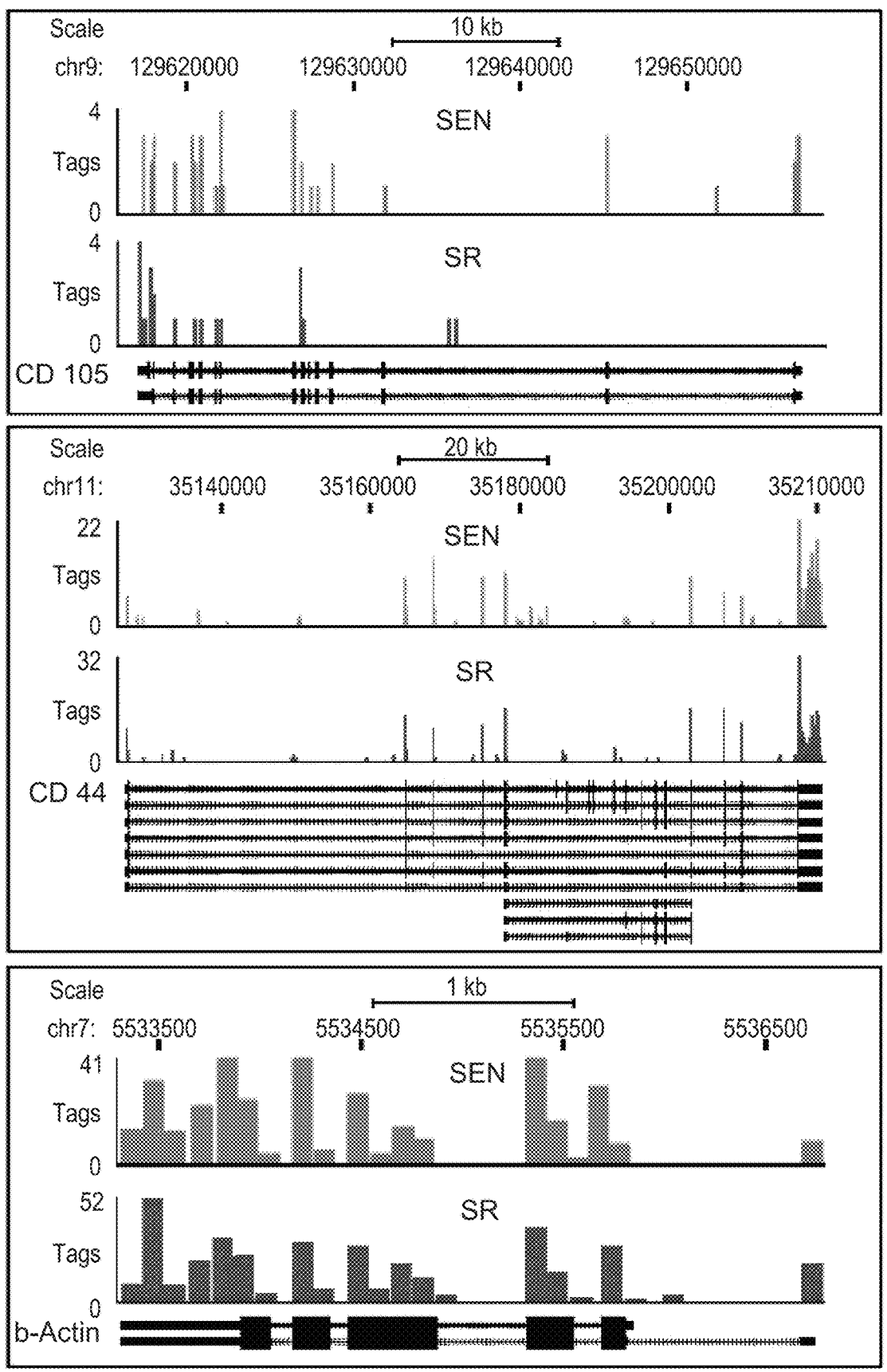

FIG. 2A depicts the immunophenotype of hADSCs upon senescence, and shows a FACS analysis of hADSCs. hADSCs were stained with FITC (CD31, CD44 and CD45) or Alexaflour-488 (CD105) conjugated antibodies against cell surface markers and subjected to flow cytometry analysis. The cell populations are shown as fluorescence to side scatter graphs (top), and the histograms (bottom) of stained cells (labeled) compared to un-stained cells (labeled); with the percentage of positive cells indicated. FIG. 2B depicts the representative analysis of CD105, CD44 and β-actin gene transcription by RNA-seq (discussed below).

Proteomic Analysis

Sample Preparation: Pellets from approximately 10$^8$ cells were lysed in 0.4 ml of lysis buffer (8M Gu-HCl+DTT). Samples were subsequently alkylated with 45 mM Iodoacetic acid (500 mM stock concentration in 1 M Ammonium Bicarbonate) in the dark fort h at room temperature. Residual alkylation agent was then reacted with 15 mM DTT. Samples were then diluted with 25 mM Tris-HCl 5 mM CaCl$_2$ to 2.5 mL and added to a glass vial of trypsin (Pierce, 20 μg, in 250 μl of 25 mM acetic acid). Samples were allowed to digest for 20 hrs at room temperature. Samples were quenched with formic acid and introduced into the mass spectrometer.

Liquid Chromatography and High-Resolution Mass Spectrometry: Stem cell samples were prepared as described above and 1 μg was injected on to a Thermo Scientific Easy nLC system configured with a 10 cm×100 μm trap column and a 25 cm×100 μm ID resolving column. Buffer A was 98% water, 2% methanol, and 0.2% formic acid. Buffer B was 10% water, 10% isopropanol, 80% acetonitrile, and 0.2% formic acid. Samples were loaded at 4 μL/rain for 10 min, and a gradient from 0-45% B at 375 nL/min was run over 130 min, for a total run time of 150 min (including regeneration and sample loading). The Thermo Scientific LTQ Orbitrap Velos mass spectrometer was run in a standard Top-10 data-dependent configuration except that a higher trigger-threshold (20 K) was used to ensure that the MS2 did not interfere with the full-scan duty cycle. This ensured optimal fill-scan data for quantification. MS2 fragmentation and analysis were performed in the ion trap mass analyzer. Samples were run in triplicate.

MS Data Analysis: Protein identification was performed using Thermo Scientific Proteome Discoverer version 1.4 (including Sequest and Percolator algorithms) using the RefSeqHuman sequence database. The Percolator peptide confidence filter was set to "high". Protein quantification was performed using Pinpoint version 1.4 software. The Pinpoint quantification workflow included importing the Proteome Discoverer .msf files as spectral libraries. Identified peptides were subsequently quantified in MS .raw files using the Pinpoint peak finding, chromatographic alignment and area calculation algorithms.

Figure 3A:
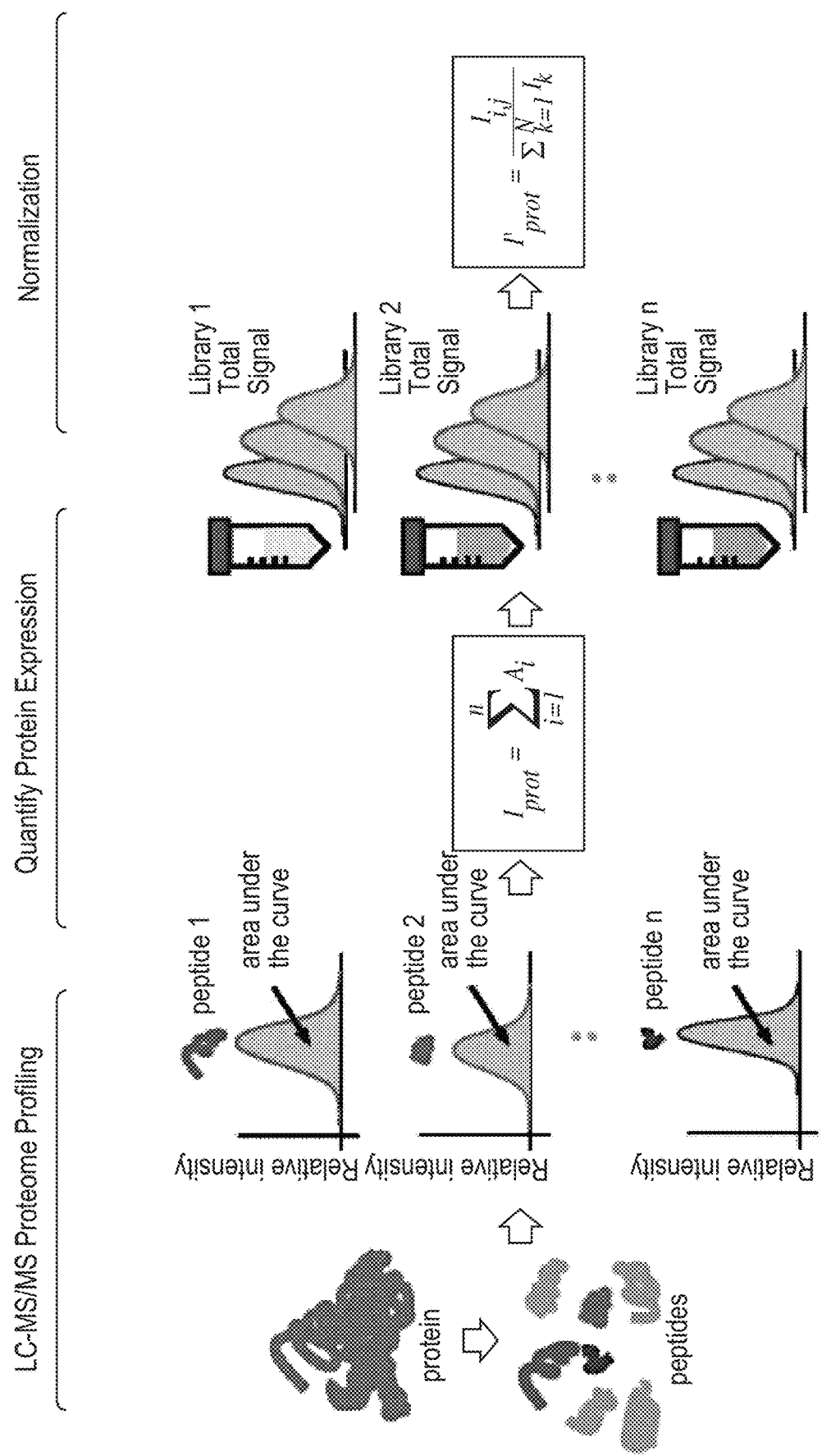
FIGS. 3A, 3B, and 3C depict a proteomic analysis scheme for evaluating differential expression between SR versus SEN hADSCs.
Figure 3B:
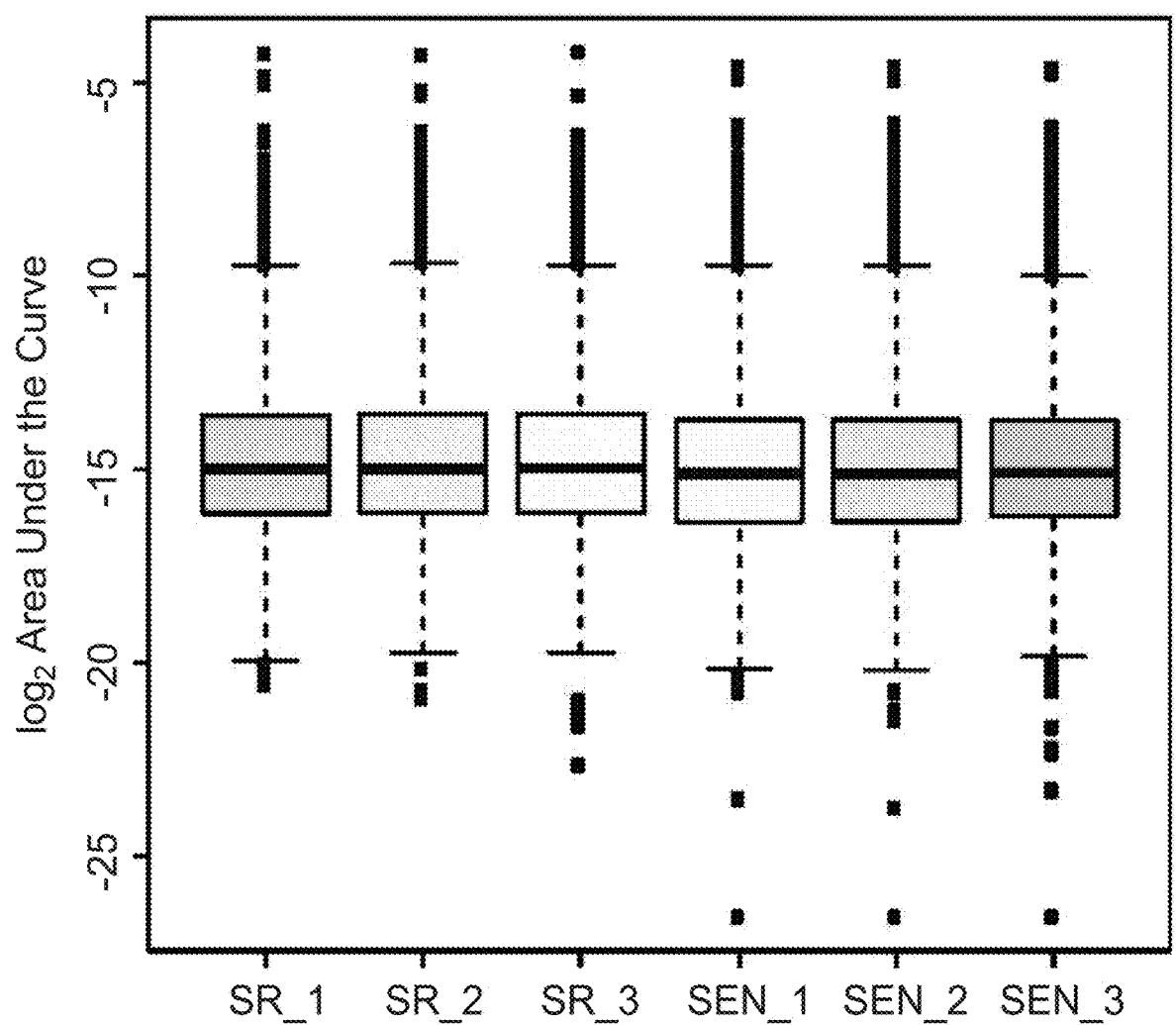
Figure 3C:
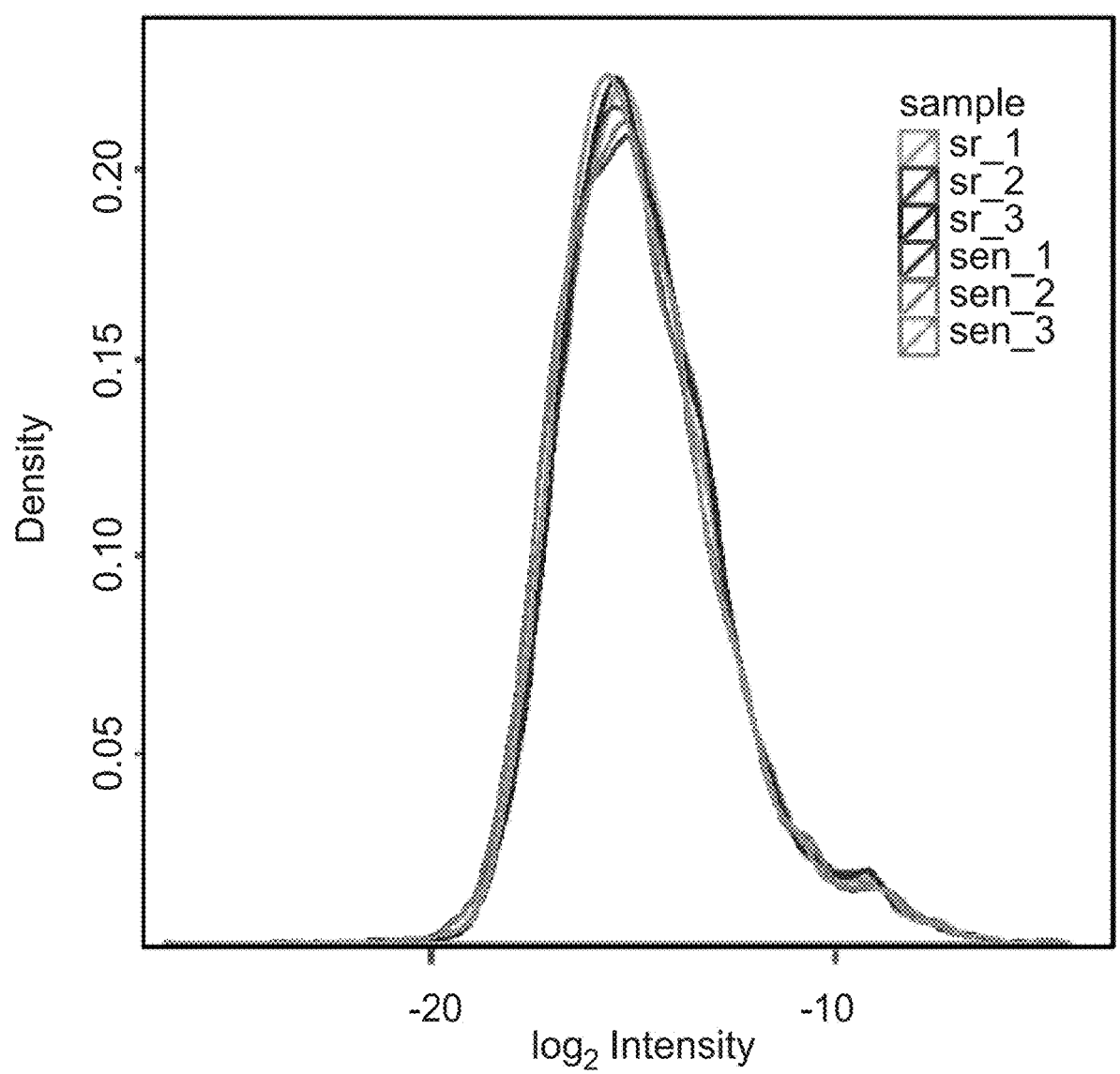

LC-MS/MS Proteome Expression Analysis: is shown in FIGS. 3A-C. Peptide expression levels are taken as the total area under the LC-MS/MS relative intensity curve (FIG. 3A) and individual peptides were unambiguously assigned to proteins using the Pinpoint software, version 1.4 (Thermo Scientific) as described above. The areas A of all peptides i assigned to an individual protein I were summed to yield raw (non-normalized) protein expression levels:

$$I = \sum_{i=1}^{n} A_i.$$

The raw protein expression levels I for each individual library, characterized as described in the previous section, were normalized against the total size of the library. For each protein i from library j, the normalized expression level I' is calculated as:

$$I' = \frac{I_{i,j}}{\sum_{k=1}^{N} I_k},$$

where N is the total number of proteins from library j. Normalized protein expression levels for the three individual SR libraries and the three individual SEN libraries were compared using the Student's t test with a P-value cutoff of 0.05 to identify proteins that are differentially expressed between SR and SEN hADSCs.

FIGS. 3A-C depict a proteomic analysis scheme for evaluating differential expression between SR versus SEN hADSCs. FIG. 3A shows a schematic illustration of the proteomic analysis workflow and the approach used to quantify and normalize protein expression levels based on the LC-MS/MS proteome profiling. FIGS. 3B and 3C show the distributions of normalized protein expression levels for the three SR and three SEN libraries analyzed here.

Transcriptome Analysis with RNA-seq

RNA-sequencing (RNA-seq) was carried out to further assess changes associated with replicative senescence via transcriptome analysis. Expression of MSC-positive and MSC-negative CD markers was assessed. Sequencing tracks were uploaded to the UCSC genome browser. FIG. 2B depicts the representative analysis of CD105, CD44 and β-actin gene transcription by RNA-seq.

Figure 4A:
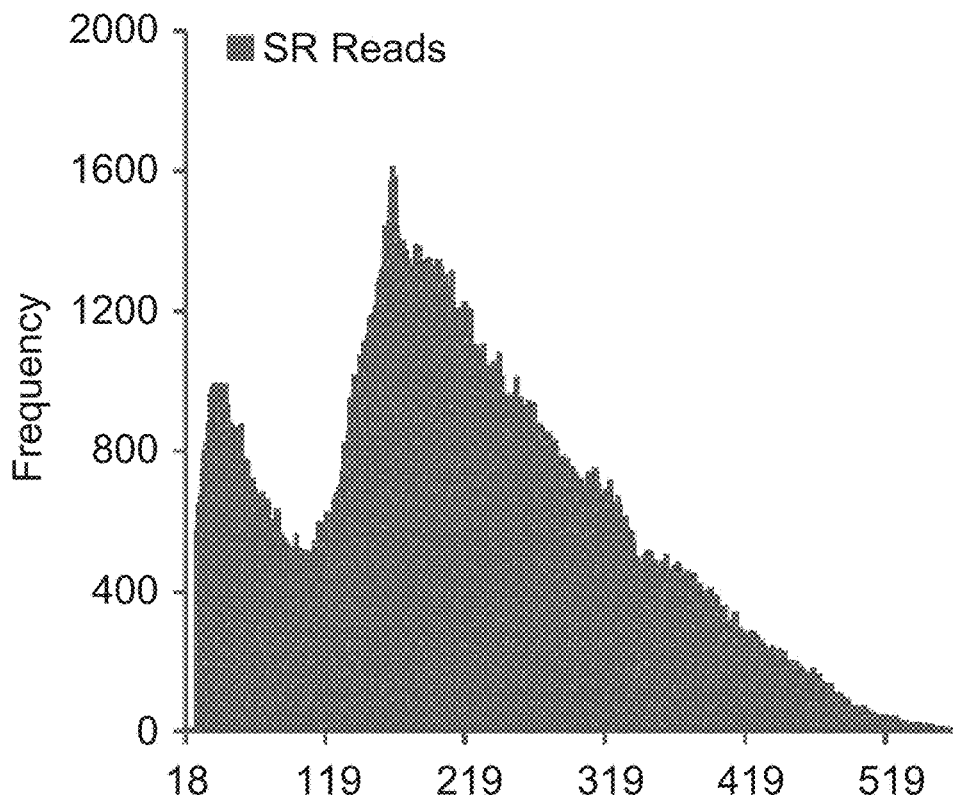
FIGS. 4A and 4B depict a RNA-seq analysis scheme for evaluating differential gene expression between SR versus SEN hADSCs.
Figure 4A:
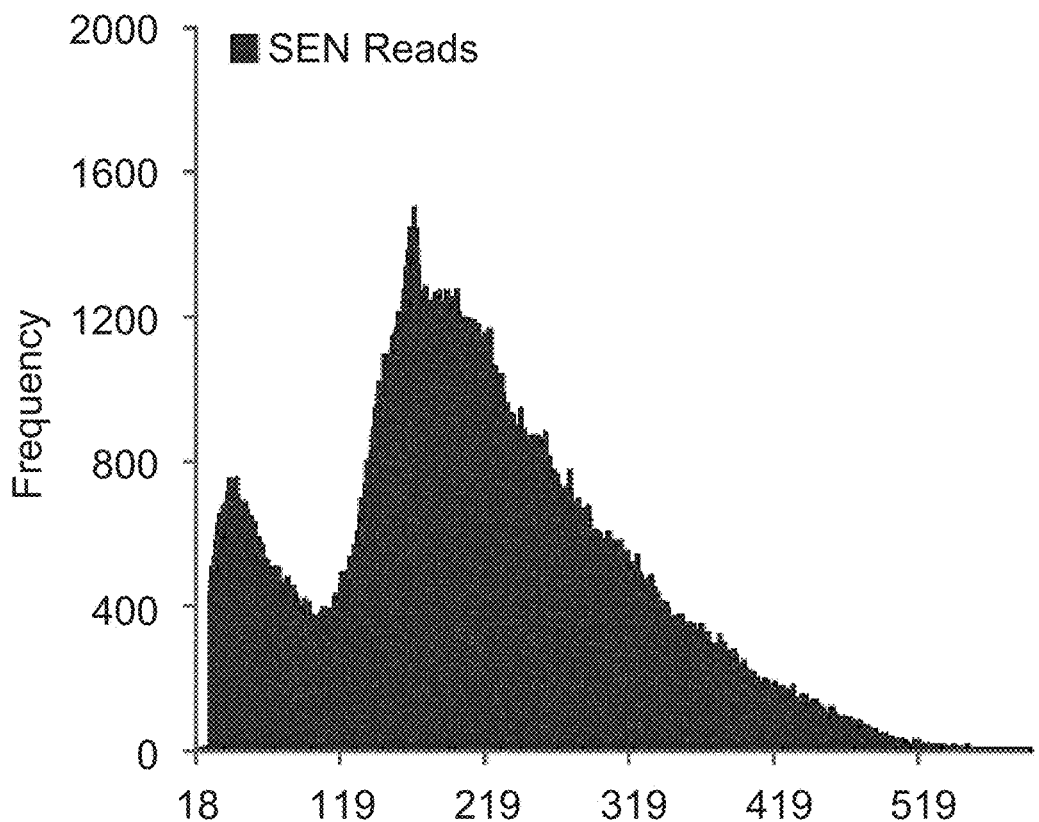

Characterization of further gene expression levels with RNA-seq was performed on single replicates of self-renewing (SR) and senescent (SEN) human adult adipose derived mesenchymal stem cells (hADSCs) using the Roche 454 pyrosequencing platform. Individual sequence reads were mapped to the human genome reference sequence (UCSC hg18, NCBI build 36.1) using the program BLAT (Kent 2002). BLAT was used in light of the relatively long sequence reads provided by 454 (avg=216 bp; FIG. 4A), and the program was run with default settings with the exception that the minimal sequence identity was set to 99%. Ties between multi-mapping sequence reads were broken by selecting the mapping location where the read was maximally covered by NCBI RefSeq annotated exons.

Figure 4B:
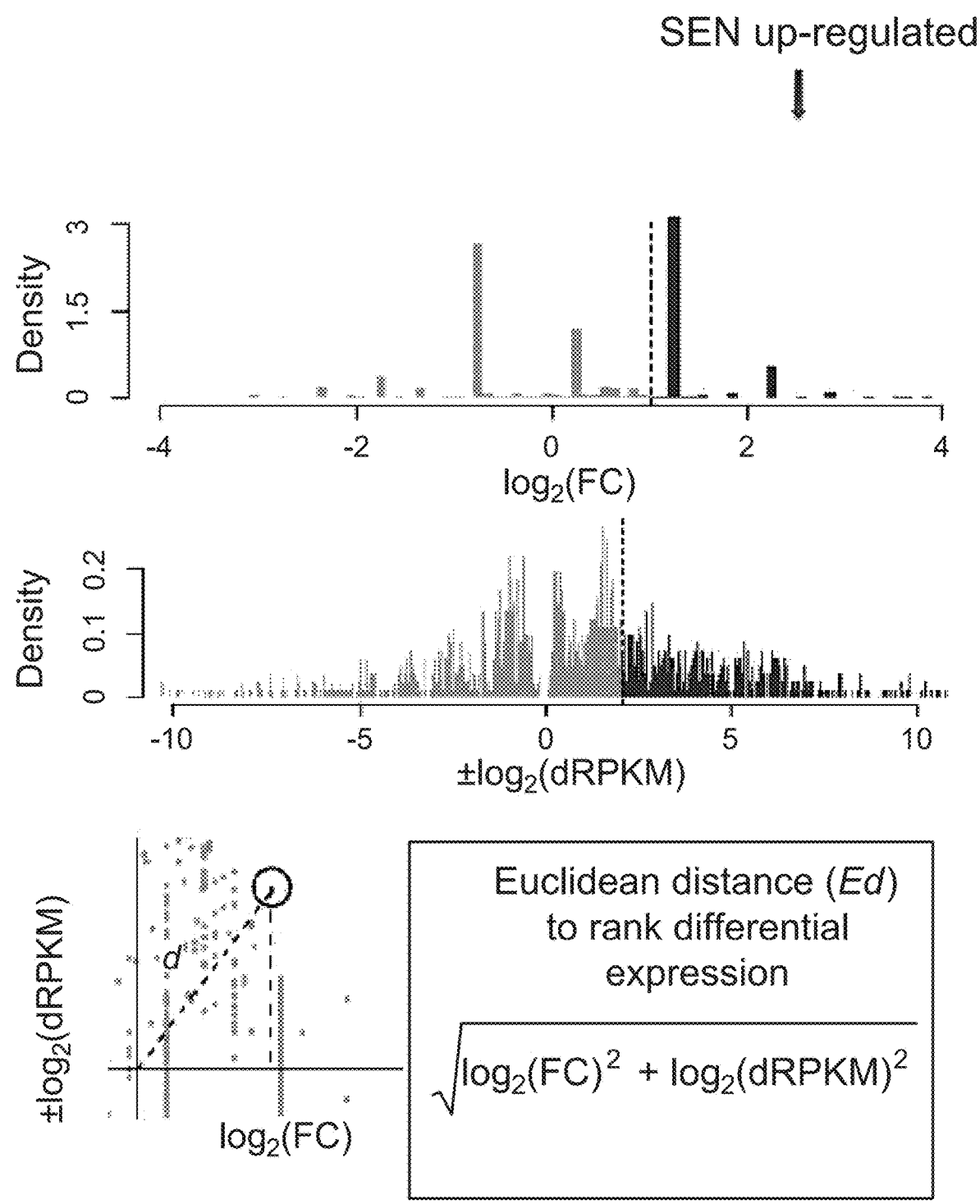
Figure 4C:
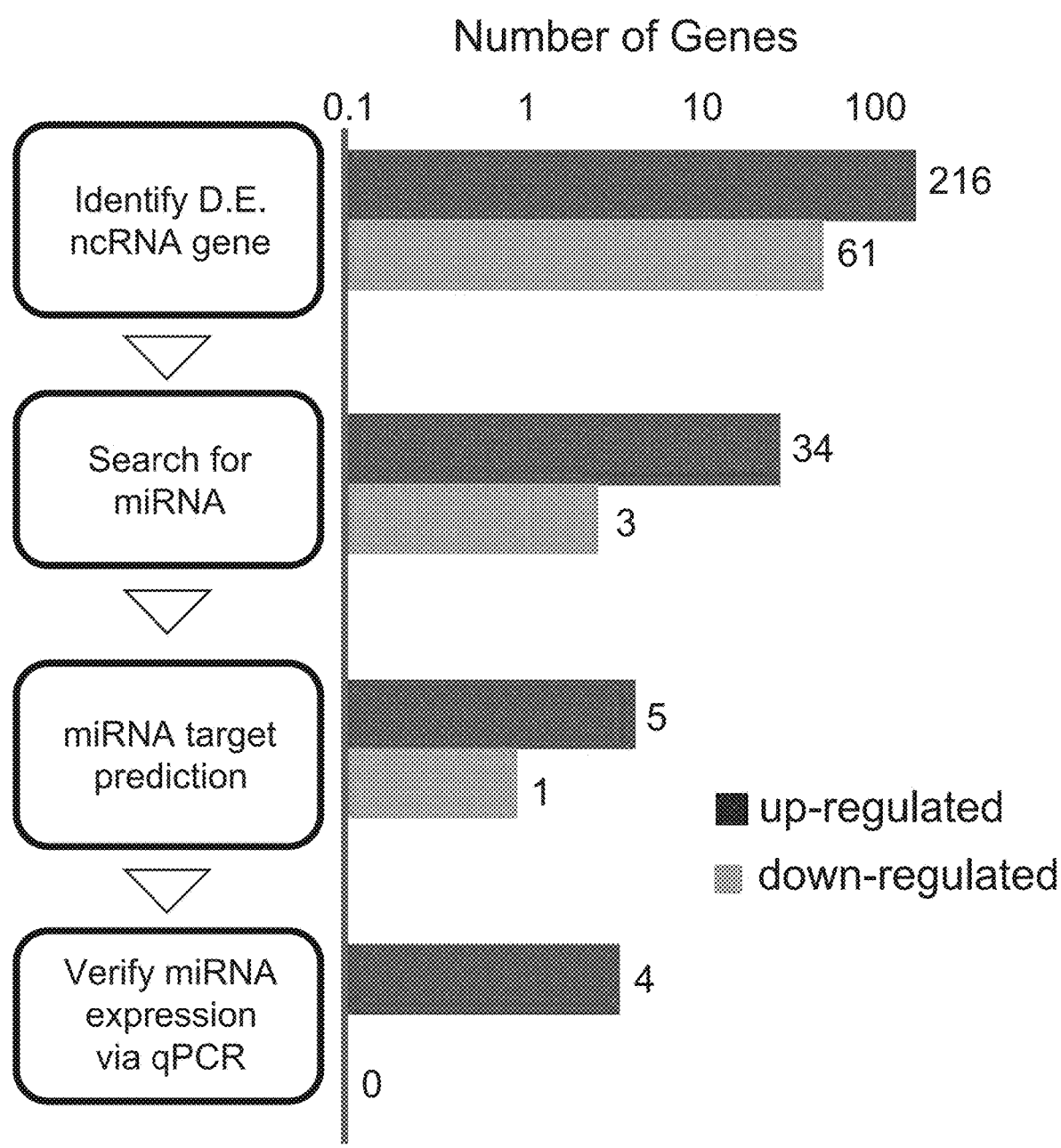
FIG. 4C depicts the overall scheme used to find differentially expressed miRNAs.

FIG. 4A-C depict RNA-seq analysis scheme for evaluating differential gene expression between SR versus SEN hADSCs. FIG. 4A shows the length distributions of RNA-seq reads for SR and SEN hADSCs. The distributions are bimodal owing to the RNA isolation approach used to enrich for small non-coding RNA species (detailed in paragraph below).

Analysis of differential gene expression levels between SR and SEN cells was performed using an approach adopted from a recently developed method that was designed to be accurate at the relatively low sequencing depth provided by 454 and for single replicate experiments (Tarazona, Garcia-Alcalde et al. 2011). This approach employs a combination of two-parameters in order to define differential expression levels between genes: 1) the difference in the number reads per kilobase per million mapped reads (dRPKM) and 2) the expression fold-change (FC) level. This approach controls for liabilities of each individual metric; in particular, dRPKM is biased towards highly expressed genes, whereas FC is biased towards lowly expressed genes. In this approach, dRPKM is defined as: $RPKM_{SR}-RPKM_{SEN}$, and FC is defined as: $\log_2 RPKM_{SR}/RPKM_{SEN}$. For each locus, dRPKM and FC are plotted as a point in two-dimensional Euclidean space, and the Euclidean Distance (D) between the origin and the point is taken to represent the differential expression level. This approach was used separately to evaluate the differential expression of mRNAs and non-coding RNAs, including miRNAs, which are typically expressed at lower levels. For each class of RNA, empirical distributions of Ed were evaluated to call genes as differentially expressed. For non-coding RNAs, differentially expressed genes are considered as those with |FC|>0.95 and |dRPKM|>4.07, and for mRNAs differentially expressed genes are considered as those with |FC|>0.58 and |dRPKM|>2.32 (FIG. 4B)

FIG. 4B shows the approach used to identify SEN upregulated genes. A combination of fold-change (FC) and RPKM differences (dRPKM) was used as described above. FC and dRPKM distributions are shown along with the empirically determined cut-offs above which genes are considered to be SEN upregulated (cut-off in FIG. 4B is indicated by a vertical dotted line). FC and dRPKM are jointly analyzed with the Euclidean distance (Ed) to quantify the extent of differential expression.

FIG. 4C presents the overall scheme used to find differentially expressed miRNAs, which have mRNA target predictions from the mirSVR program, and is shown along with the corresponding numbers of miRNAs identified at each step.

Comparative transcriptomic analysis (RNA-seq) between SR and SEN hADSCs revealed a number of ncRNAs that are upregulated in SEN compared to SR hADSCs. Differentially expressed ncRNAs are identified as those that have levels of fold change ($\log_2$ SEN/SR) and differences in the normalized number of reads (dRPKM SEN-SR) as shown in FIG. 4B, where FC and dRPKM distributions are shown along with the empirically determined cut-offs above which genes are considered to be SEN upregulated (shown in the box). FC and dRPKM are jointly analyzed with the Euclidean distance (Ed) to quantify the extent of differential expression, 216 ncRNAs upregulated upon senescence have been identified (shown in the upper right quadrant of FIG. 5A). Three out of four upregulated ncRNA loci encode polycistronic transcripts that could be processed to yield multiple miRNAs (FIG. 5B): chr11:MIR100HG (encoding mir-125b1, mir-let7a-2, mir-100), chr13: MIR17HG (encoding mir-17, mir-18a, mir-19a, mir-20a, mir-19b-1, mir-92a-1) and chr22: MIRLET7BHG (encoding mir-3619, mir-let7a-3, mir-4763, mir-let-7b).

Figure 5A:
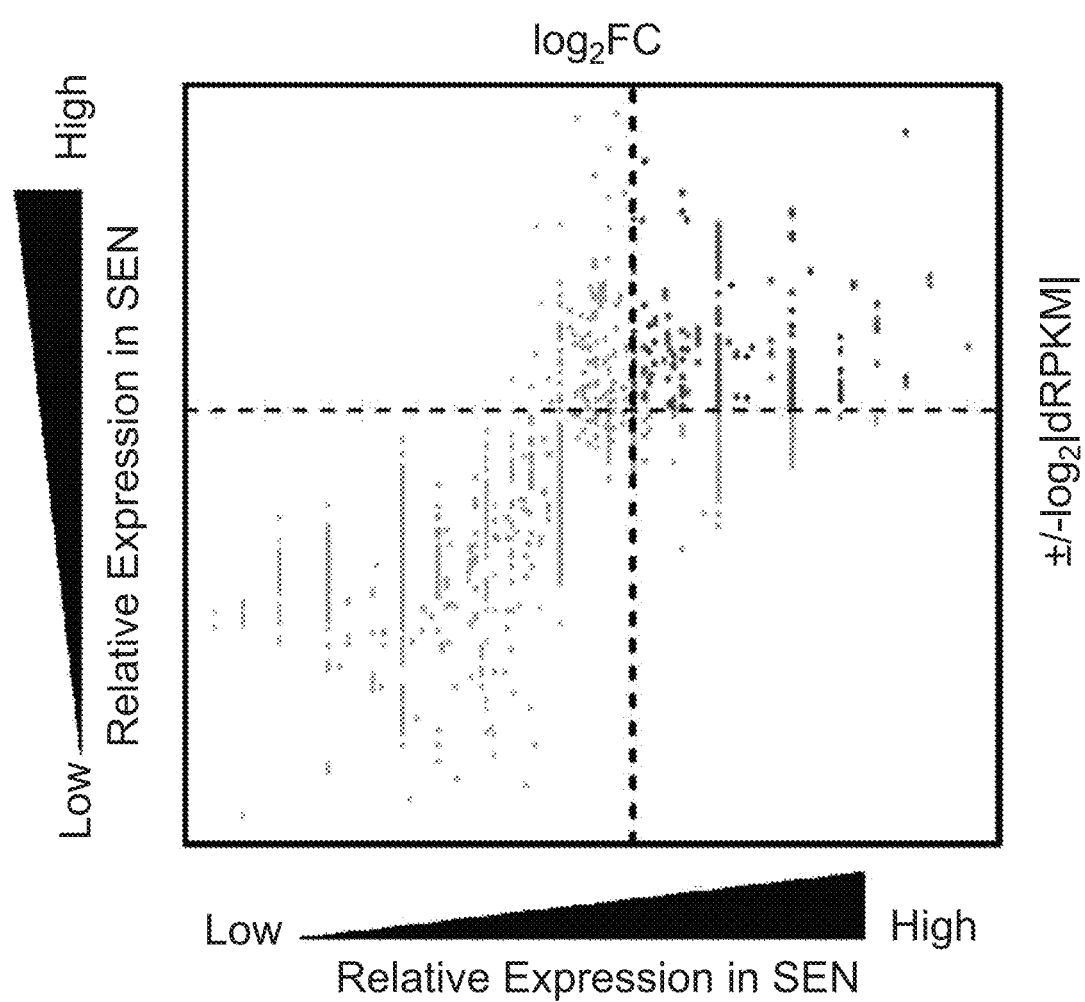
FIG. 5A depicts differential expression of non-coding RNA genes in SR versus SEN hADSCs revealed by RNA-seq analysis.
Figure 6A:
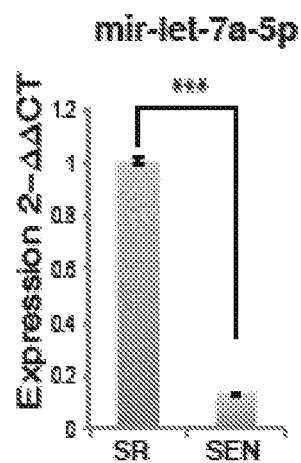
FIGS. 6A and 6B depicts mir-let7a-5p and AGO-3 expression analysis in hADSCs upon senescence.

FIG. 5A shows differential expression of non-coding RNA genes in SR versus SEN hADSCs revealed by RNA-seq analysis. Fold-change values ($\log_2$ SEN/SR) are shown on the x-axis and RPKM differences ($\log_2$ SEN-SR) are shown on the y-axis. SEN upregulated non-coding RNA genes are shown in the upper right quadrant). FIG. SB shows genomic locations and locus names for SEN upregulated miRNA gene clusters revealed by RNA-seq analysis.

Example 2: DifferentialExpression of microRNAs upon Replicative Senescence of hADSCs This example shows differential expression of microRNAs (miRNAs) upon SEN of hADSCs.

Upregulation of functionally antagonistic MIR17HG and MIR100HG miRNA-bearing loci upon senescence was further investigated. The human chromosome 13 MIR17HG cluster (800 bp) encodes six tightly grouped miRNAs with four distinct "seed" sequences (Khorshid, Hausser et al. 2013, Hausser and Zavolan 2014): mir-17, mir-18a, mir-19a, mir-20a, mir-19b1, and mir-92a1 (schematically shown in FIG. 5C). The miRNAs from this locus have been designated as onco-miRNAs because of their importance in cell transformation and tumorigenesis (Kent and Mendell 2006, Mendell 2008). The chromosome 11 MIR100HG cluster houses three microRNAs (mir-125b1, mir-let7a-2, mir-100) situated within a comparable genomic distance (FIG. 5D).

miRNAs are frequently transcribed together as polycistronic primary transcripts that are processed into multiple individual mature miRNAs (Stefani and Slack 2008). To identify specific microRNA production from these clusters in SEN hADSCs, the abundance of mature miRNAs originating from both guide strand (mir-5p) and passenger strand (mir-3p/mir*) by the MystiCq microRNA qPCR Assay System was examined, as described below.

RT-PCR

The microRNA was isolated using a mirPremier microRNA isolation kit (Sigma-Aldrich). microRNA was quantified with a NanoDrop ND-2000 Spectrophotometer (Thermo Scientific). For miRNA cDNA synthesis, the Mystic microRNA cDNA synthesis Mix kit (Sigma-Aldrich) was used. All microRNA assay primers were bought from Sigma-Aldrich.

Real-Time Quantitative PCR

Quantification of microRNA expression for candidate genes was performed by real-time quantitative PCR (qRT-PCR) using the LightCycler® 480 Real-Time PCR System (Roche). microRNA was reverse transcribed by using the Mystic microRNA cDNA synthesis Mix kit (Sigma-Aldrich). All microRNA assay primers were bought from Sigma-Aldrich. qRT-PCR reactions were performed with the mystic microRNA SYBR green qPCR ReadyMix in a MicroAmp optical 96-well reaction plate. The PCR amplification of microRNA was performed in a LightCycler® 480 Real-Time PCR System (Roche) using the following program: Cycle 1, 95° C. for 2 min. Cycle 2, 40 cycles of 95° C. for 5 sec, 60° C. for 30 sec. Relative expression values of microRNA were obtained by normalizing CT values of the microRNA genes in comparison with CT values of the endogenous control (U6) using the CT method.

Figure 5C:
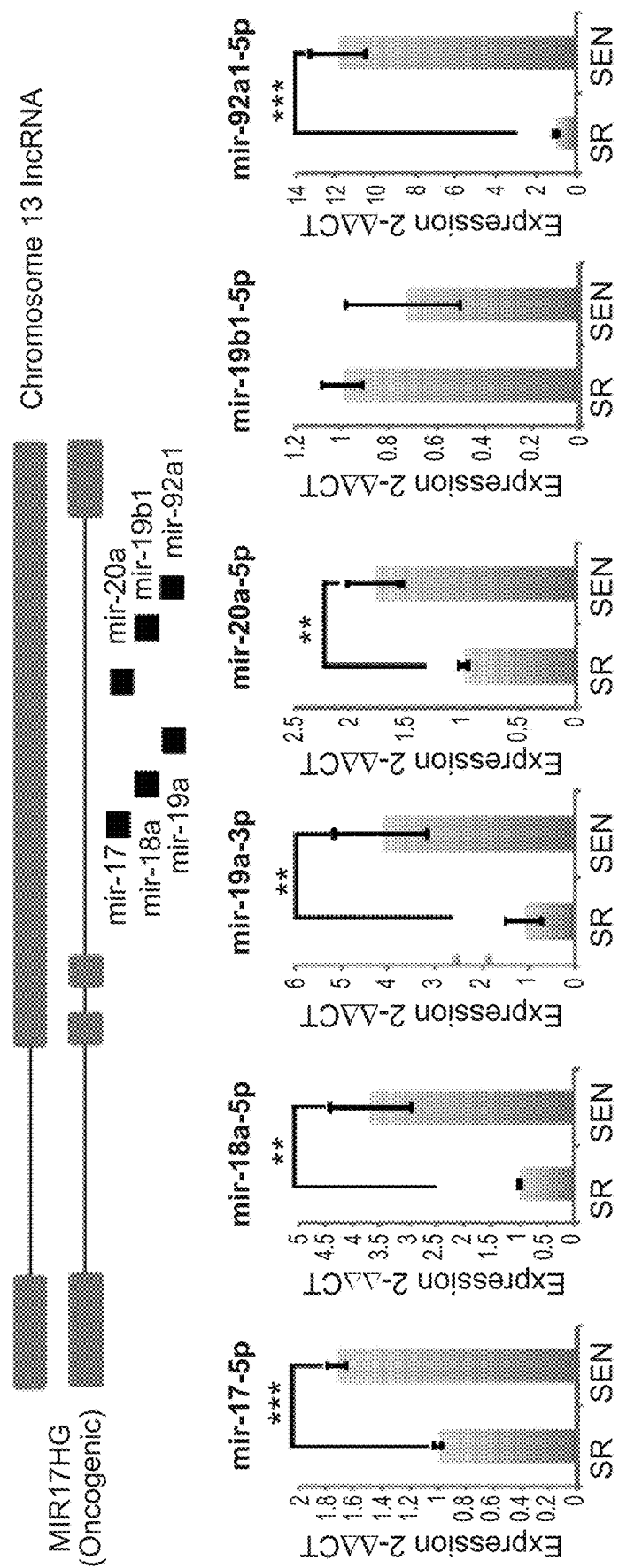

Analysis of the MIR17HG cluster has revealed that only mature guide strand miRNAs: mir-17-5p, mir-18a-5p, mir-20a-5p, mir-19b1-5p and mir-92a1-5p, are detected in both SR and SEN hADSCs (FIG. 5C). No mature passenger strands: mir-17-3p, miR-18a-3p, miR-20a-3p, mir-19b1-3p and mir-92a1-3p, have been observed in the tested samples. Contrary to that, only mature passenger strand miRNA for mir-19a-3p was recorded by real-time PCR (FIG. 5C). A statistically significant senescence-related increase in production of mature miRNAs has been observed, in accordance with their corresponding primary non-coding transcripts MIR17HG: miR-17-5p ($p<0.001$), miR-18a-5p ($p<0.01$), miR-20a-5p ($p<0.01$), mir-92a1-5p ($p<0.001$) and mir-19a-3p ($p<0.01$) (FIG. 5C and FIG. 6A). No significant change in the mature mir-19b1-5p has been detected upon replicative senescence of hADSCs (FIG. 5C).

Figure 6B:
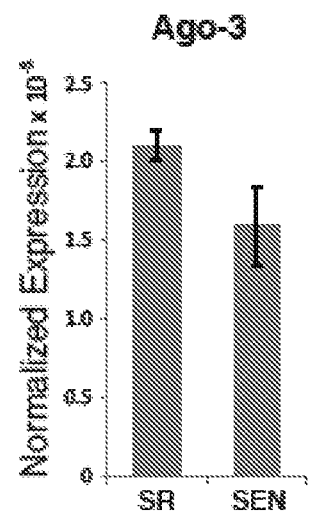

The MIR100HG cluster gives rise to two guide strand mature miRNAs: mir-125b1-5p and mir-100-5p in SEN hADSCs. No mature passenger strands: mir-125b1-3p and mir-100-3p have been detected in the samples. Both guide mir-let7a-2-5p and passenger mir-let7a-2-3p have been detected in both SR and SEN conditions, where the balance in the stability/maturation preference of guide mir-let7a-2-5p is shifted upon SEN, favoring the production of passenger strand mir-let7a-2-3p (greater than 25-fold upregulation shown in FIGS. 5C and 6A. This switch in the mature strand selection for mir-let7a-2 in SEN hADSCs is not due to an increase in AGO3 protein expression as was reported previously (Winter and Diederichs 2013). The level of endogenous AGO3 protein does not seem to change significantly with replicative senescence FIG. 6B. FIG. 6B shows protein levels of AGO-3 protein measured in proteotnic study as described above. Normalized protein expression levels are shown for three replicate samples each of SR versus SEN hADSCs.

Together, these data provide evidence that senescence of hADSCs correlates with a upregulation of the subset of mature miRNAs from the MIR100HG and MIR17HG clusters, and for some of them, such as mir-let7a-2, a notable shift in the maturation equilibrium between guide and passenger strands of microRNA has been observed. These abundantly upregulated mature miRNAs are called herein: senescence-associated micro RNAs (SA-miRNAs).

FIG. 5C depicts graphical representation of oncogenic MIR17HG locus and qPCR analysis of mature mirRNA expression in self-renewing (SR, left bar) and senescent (SEN, right bar) states of hADSCs. Relative expression of either passenger strand mature microRNAs (depicted in the graphs as −3p) or guide strand mature microRNAs (depicted in the graphs as −5p) to U6 small RNA was measured. Data are shown as fold change ($\Delta\Delta C\tau$). The mean±SD from three independent experiments is shown. The statistical difference was evaluated by Student's t-test and P-value (p) related to experimental measurements and are listed under the graphs, where *$p<0.001$, $p<0.01$. FIG. 5D depicts graphical representation of tumor-supressive MIR100HG locus and qPCR analysis of mature miRNA expression in self-renewing (SR, left bar) and senescent (SEN, right bar) states of hADSCs. Relative expression of either passenger strand mature microRNAs (depicted in the graphs as −3p) or guide strand mature microRNAs (depicted in the graphs as −5p) to U6 small RNA was measured. Data are shown as fold change ($\Delta\Delta C\tau$) The mean±SD from three independent experiments is shown. The statistical difference was evaluated by Student's t-test and P-values (p) related to experimental measurements are listed under the graphs, where ***p<0.001.

FIG. 6 depicts mir-let7a-5p and AGO-3 analysis in hADSCs upon senescence. FIG. 6A shows the qPCR analysis of mature miRNA expression in self-renewing (SR, left bar) and senescent (SEN, right bar) states of hADSCs. Relative expression guide strand of mature microRNA mir-let7a- (depicted in the graphs as −5p) to U6 small RNA was measured. Data are shown as fold change ($\Delta\Delta C\tau$). Mean±SD from three independent experiments is shown. The statistical difference was evaluated by Student's 1-test and P-values (p) related to experimental measurements are listed under the graphs, where ***p<0.001. FIG. 6B shows the protein levels of AGO-3 protein measured in proteomic study as described in Example 1. Differential expression of proteins upon self-renewal (SR) and senescence (SEN) of hADSCs. Normalized protein expression levels are shown for three replicate samples each of SR versus SEN hADSCs.

Example 3: Identification of the Targets of SA-microRNAs

This example characterizes the downstream gene targets of senescence associated miRNAs, using a combination of transcriptome and proteome analysis.

Despite the availability of miRNA target prediction algorithms, it still remains a challenge to accurately predict the potential target genes of a given miRNA. A number of these prediction algorithms use sequence, contextual, structural and/or evolutionary constraints and rely on subsequent validation of the targets by large scale mRNA expression level assessment (Sethupathy, Megraw et al. 2006). However, transcriptional analysis of miRNA target genes does not fully reveal the extent to which miRNAs can exert control on protein expression levels, which have a tendency to change more dramatically than mRNA levels (Liu 2008, Selbach, Schwanhausser et al. 2008, Hausser and Zavolan 2014).

Figure 7A:
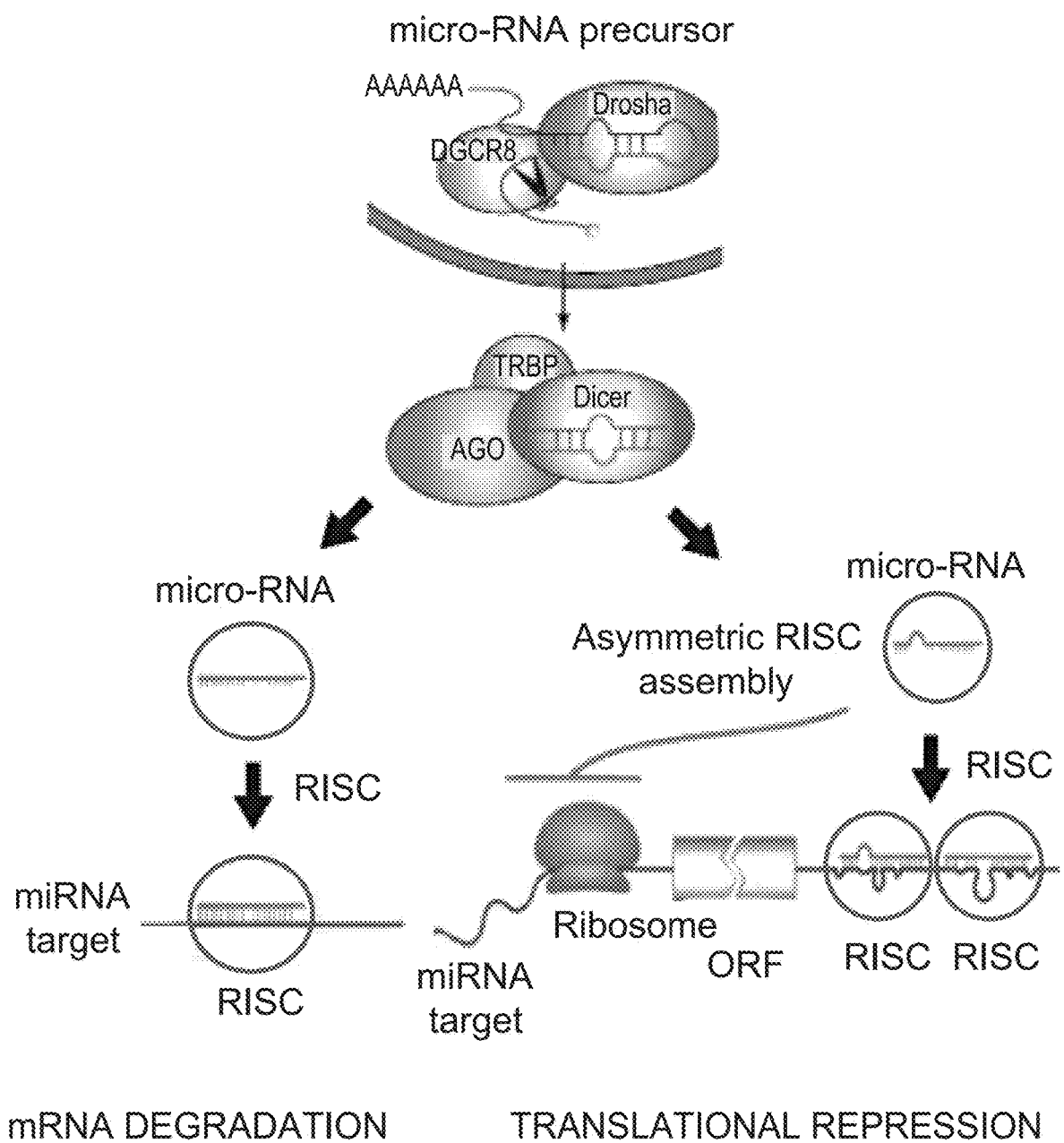

Thus, an integrated approach is taken here, as illustrated in FIGS. 1, 3, and described in Example 1 to simultaneously explore two mechanisms by which SA-miRNAs might exert their functional effects. FIG. 7 provides a schematic illustration of mRNA degradation versus translational repression modes of miRNA regulation: 1) mRNA degradation (FIG. 7A-left side of the figure; and 2) inhibition of protein translation without triggering mRNA decline (translational repression; FIG. 7A-right side of the figure.

Figure 7B:
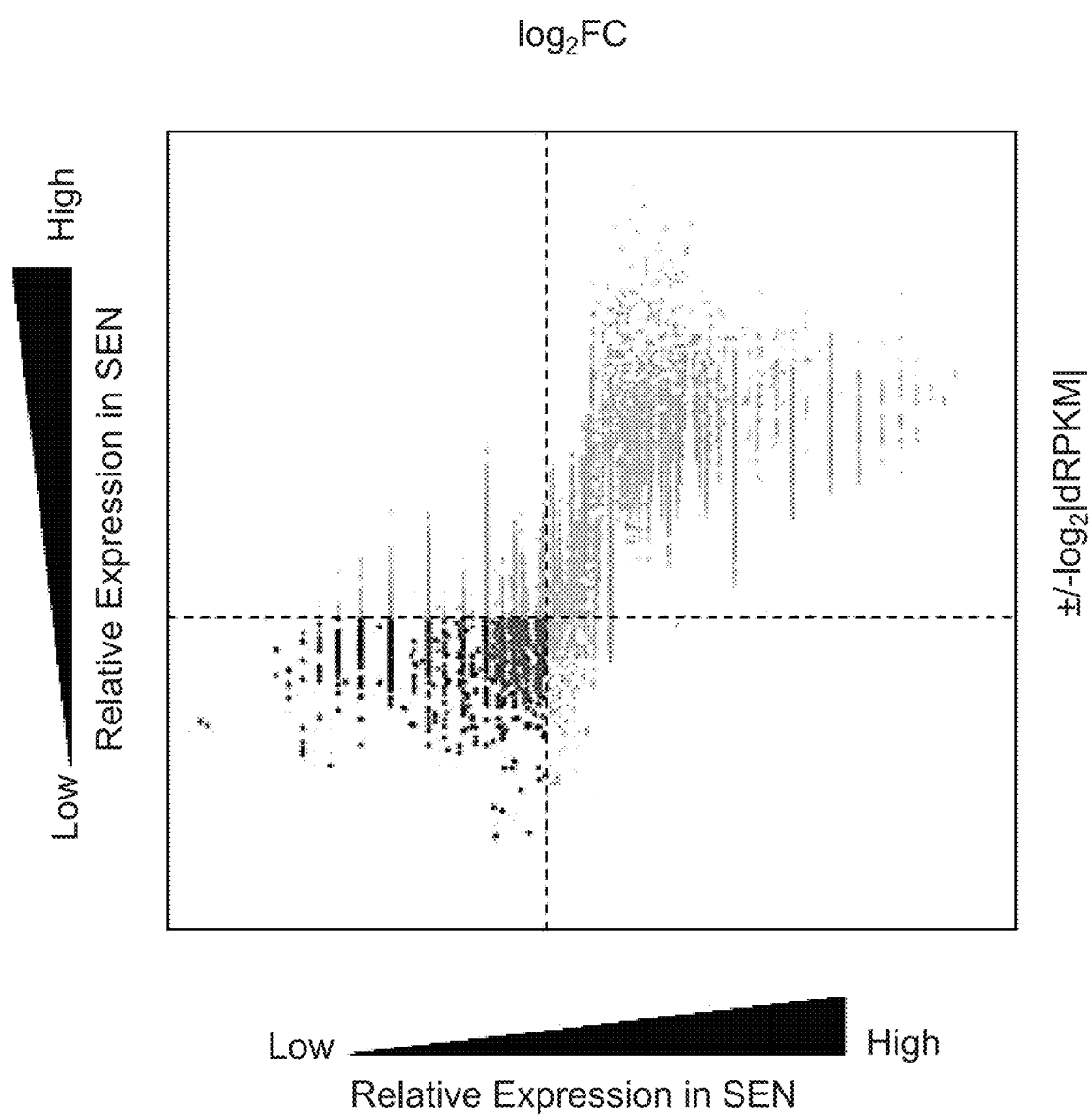

To relate SA-miRNAs to the downregulation of their target genes at the level of mRNA and/or protein expression, the analysis has been focused on SEN downregulated mRNAs and proteins. SEN downregulated mRNAs are characterized as those that have low levels of fold change ($\log_2$ SEN/SR) and the smallest values for the difference in the normalized number of reads (dRPKM SEN-SR), There are a total of 937 SEN downregulated mRNAs that have been identified in this way (shown in the lower left quadrant of FIG. 7B). FIG. 7B shows the differential expression of protein coding mRNAs in SR versus SEN hADSCs. Fold-change values ($\log_2$ SEN/SR) are shown on the x-axis and RPKM differences ($\log_2$ SEN-SR) are shown on the y-axis, SEN downregulated protein coding mRNAs are shown (lower left quadrant). SEN downregulated proteins have been identified by comparing protein expression levels across SR versus SEN replicate samples. There are 986 proteins that have shown significantly lower levels of expression among SEN replicates compared to SR replicates (shown in the lower right quadrant of FIG. 7C). The heat map in FIG. 7C depicts differential expression of proteins in SR versus SEN hADSCs. Normalized protein expression levels are shown for three replicate samples each of SR versus SEN hADSCs (see z-score scale). SEN downregulated proteins are shown in the lower right quadrant.

Figure 8:
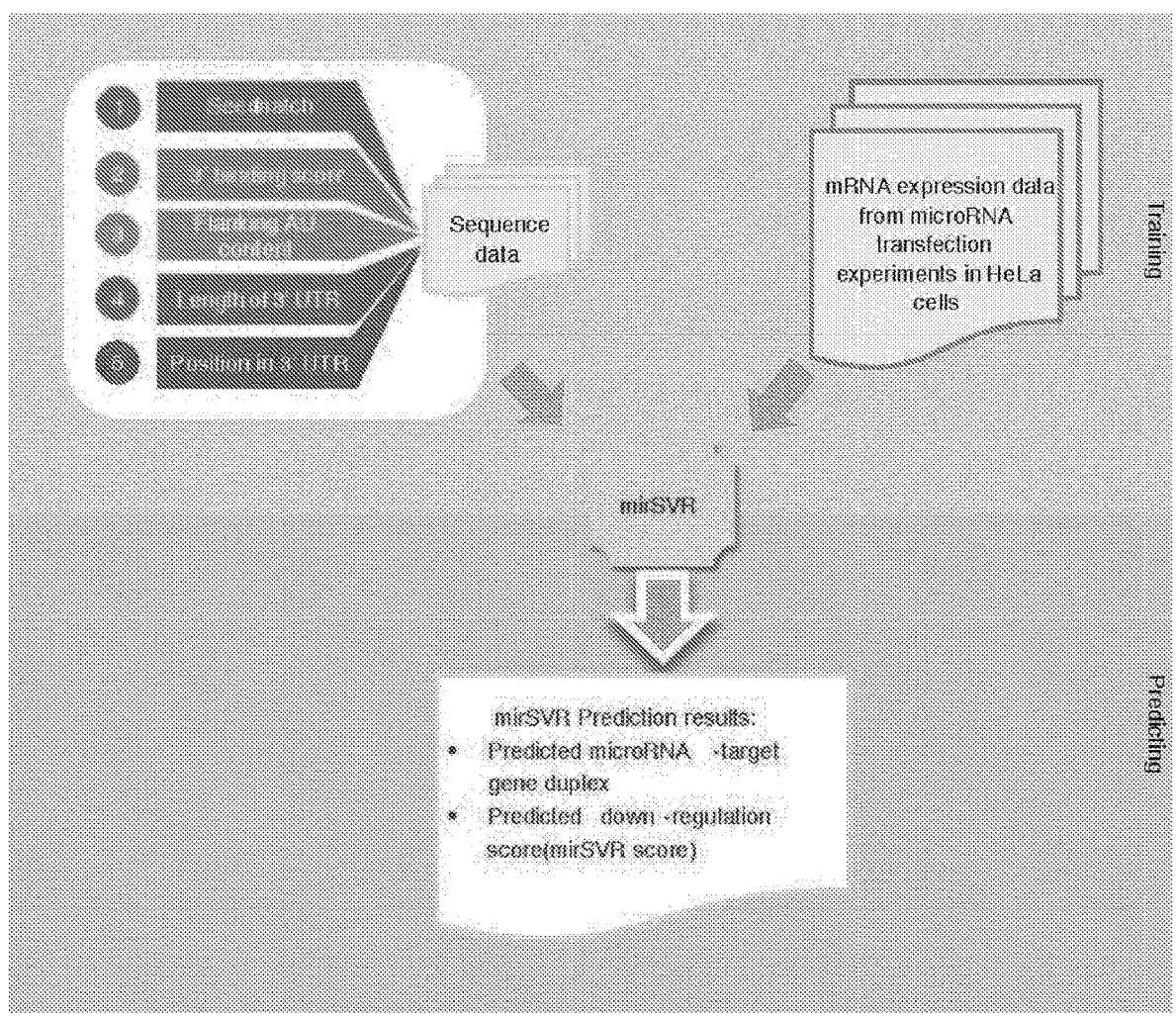
FIG. 8 depicts the overview of the approach used to predict miRNA targets via the program mirSVR.

Having identified SEN downregulated mRNAs and proteins in this way, the mirSVR prediction algorithm was applied to search for potential target genes of SA-miRNAs (FIGS. 5C and 5D) among these mRNAs and proteins. The mirSVR algorithm has been chosen because it combines miRNA-mRNA binding site sequence analysis with several additional sources of contextual information, including gene expression data from miRNA transfection experiments, in order to make target predictions (FIG. 8). Accordingly, mirSVR has been shown to yield a relatively low rate of false positive predictions for miRNA target identification (Betel, Koppal et al, 2010). mirSVR also provides scores in order to rank the predicted targets. For this study, a conservative approach is taken for miRNA prediction by only selecting targets with a score <−0.2 for further analysis. FIG. 8 depicts an overview of the approach used to predict miRNA targets via the program mirSVR. The mirSRV program's approach to identifying potential miRNA targets is distinguished by its use of mRNA expression data from miRNA transfection experiments in HeLa cells along with sequence and contextual data for miRNA-mRNA seed matching regions. Among 8367 targets predicted by mirSVR, 389 mRNAs and 418 proteins have been downregulated upon senescence of hADSCs (shown as Venn diagram in FIG. 7D). In FIG. 7D, a flowchart illustrating the approach to identifying downregulated SA-miRNA targets is shown along with a Venn-diagram indicating the numbers of genes or proteins identified via each method and the numbers identified by multiple methods.

Collectively, the SA-miRNA target genes captured by this approach represent numerous biological pathways (FIG. 14) relevant to the establishment and/or maintenance of the senescence phenotype pathways in hADSCs.

Example 4: Validity and Sensitivity of the integrated Transcriptome and Proteome Approach for the Identification of SA-miRNA Target Genes This example further characterizes and validates the identified downstream gene targets of senescence associated miRNAs.

Figure 9A:
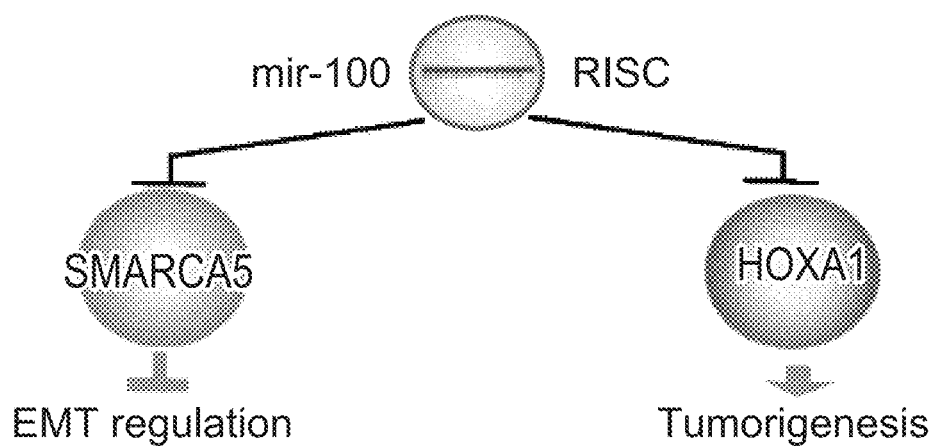
FIGS. 9A-B depict the regulation of SMARCA5 and HOXA1 by the MIR100HG cluster.
Figure 9B:
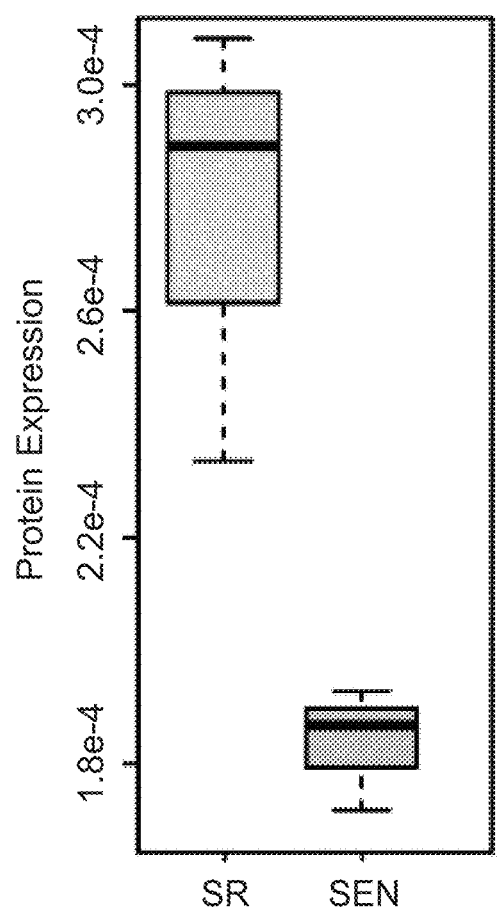
Figure 9B:
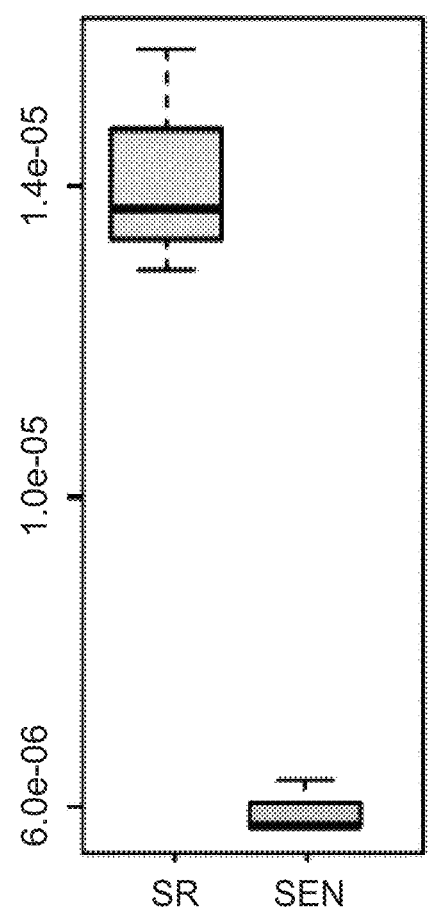

To verify the validity and sensitivity of the integrated approach for the identification of SA-miRNA target genes, gene expression of two previously established targets of mature mir-100 from the MIR100HG locus, the HOXA1 and SMARCA5 genes was evaluated (Sun, Lee et al. 2011, Chen, Sun et al. 2014). mir-100 directly targets these genes in mammary epithelial cells, imposing epithelial-to-mesenchymal transition (EMT) through downregulation of their expression (see FIG. 9A for schematic of previously demonstrated mir-100 regulation of SMARCA5 and HOXA1 along with the downstream functional effects). Consistent with published findings, the LC-MS/MS proteomic data demonstrate that the protein expression levels of both SMARCA5 and HOXA1 are significantly reduced upon senescence of hADSCs (FIG. 9B) in accordance with endogenous upregulation of mir-100-5p (FIG. 5D). FIG. 9B shows SR versus SEN protein expression levels for SMARCA5 and HOXA1. Protein expression values are shown for three replicates each for SR and SEN along with the significance of the differences (Student's t-test). Both SMARCA5 and HOXA1 mRNA levels in SEN cells do not show significant downregulation when compared to SR cells, thus suggesting that mir-100-5p operates via the translational repression pathway shown in FIG. 7A (right panel). These findings provide a proof that the approach is effective and reliable for deciphering targets of SA-miRNA action.

Example 5: Destabilization of mRNA and Translational Repression Through SA-miRNAs upon Senescence of hADSCs This example details the downstream mRNA and protein downregulation in SEN hADSCs.

Figure 10A:
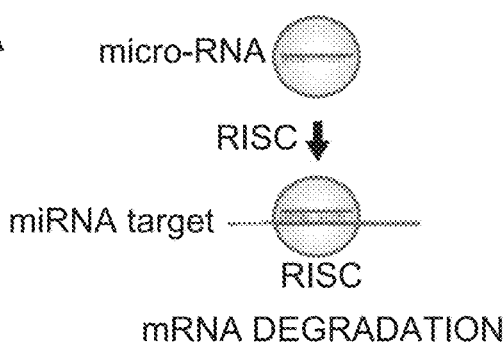
FIGS. 10A-E depict downregulation of SEN protein coding genes via miRNA-based mRNA degradation and experimental validation of SA-miRNA targets.
Figure 10B:
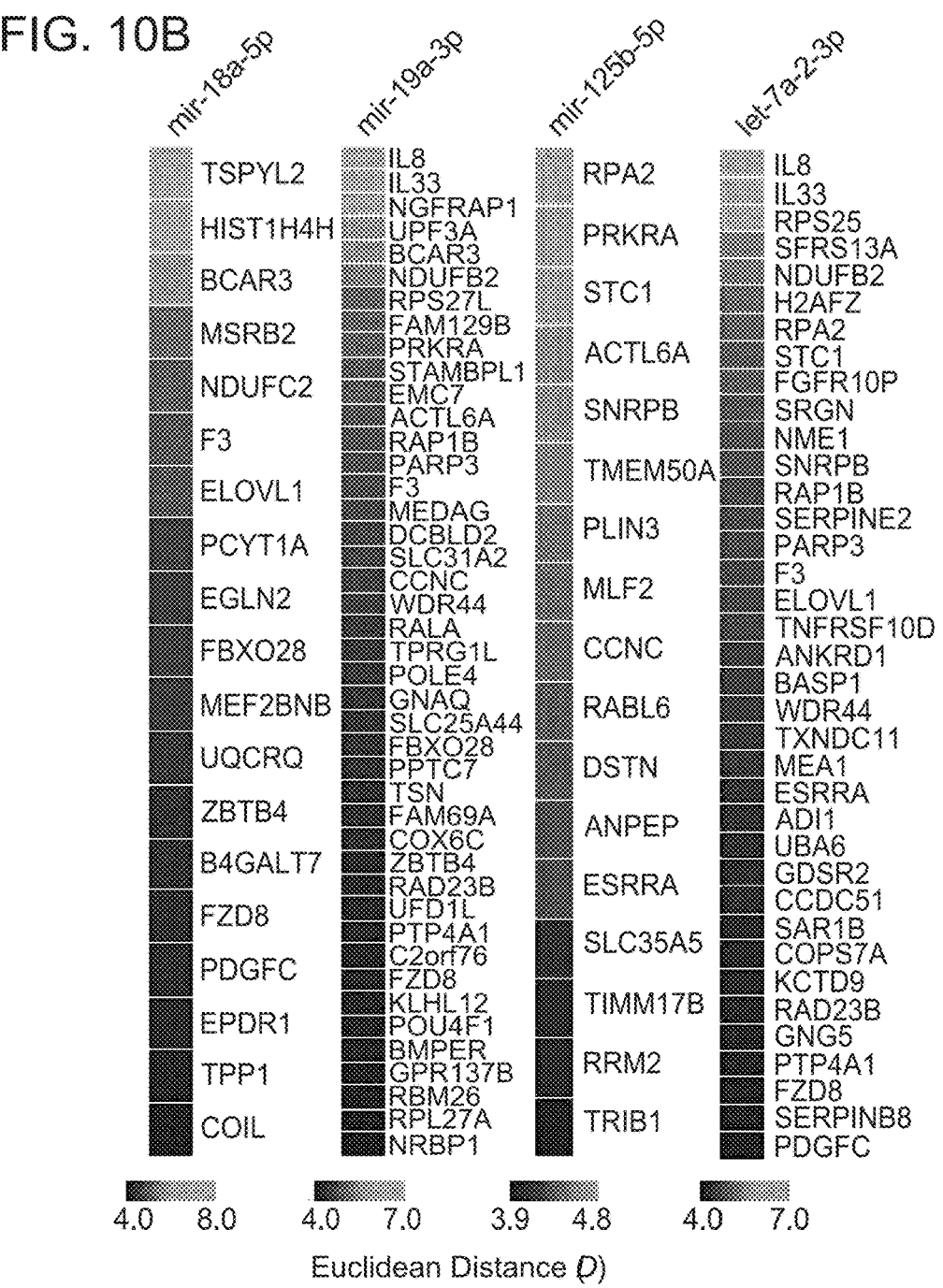
Figure 11A:
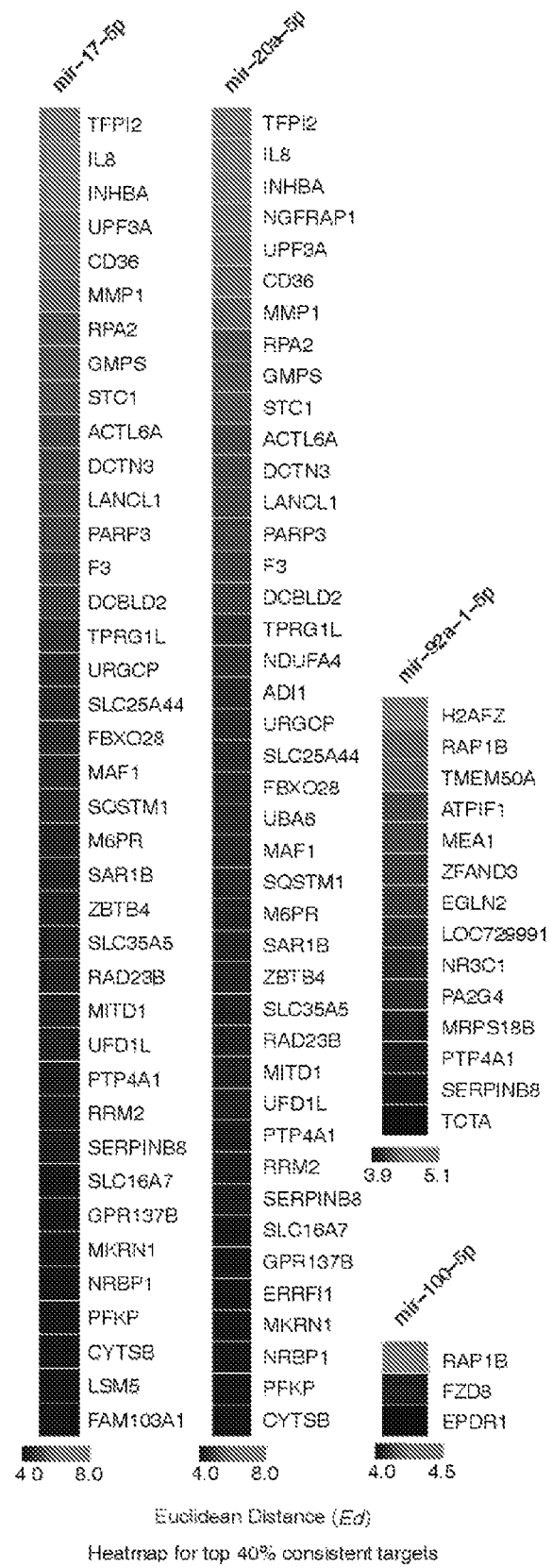
FIGS. 11A-B depict the coordinated regulation of SEN downregulated protein coding mRNAs by multiple SA-associated miRNAs.

The transcriptome analysis revealed 389 downregulated. mRNA representing senescence-associated degradation targets of SA-miRNAs in hADSCs (FIGS. 7 and 10A). FIG. 10A shows a schematic of miRNA regulation via mRNA degradation, resulting in reduction of mRNA levels). Representative heatmaps of transcriptional changes of SA-miRNA mRNA targets for each individual SA-miRNA are shown in FIG. 10B and FIG. 11A. FIG. 10B and FIG. 11A show SEN downregulated protein coding mRNAs targeted by SA-associated miRNAs. Differential expression levels are quantified by the Euclidean distance (Ed) as described in Example 1 and FIG. 4.

Table 2 provides a list of mRNA targets downregulated in SEN hADSCs through miRNAs.

TABLE 2 mRNA Targets Downregulated in SEN Through miRNAs

| Gene Symbol | RefSeq ID | mirSVR Score | SR | SEN | dRPKM | FC | D |
|---|---|---|---|---|---|---|---|
| mir-17-5p (MIMAT0000070) | | | | | | | |
| TFPI2 | NM_006528 | −0.25 | 528.90 | 225.72 | −303.17 | −1.23 | 8.34 |
| IL8 | NM_000584 | −1.18 | 89.60 | 8.90 | −80.69 | −3.33 | 7.16 |
| INHBA | NM_002192 | −0.36 | 282.13 | 177.25 | −104.88 | −0.67 | 6.75 |
| UPF3A | NM_023011 | −0.31 | 18.45 | 1.27 | −17.18 | −3.86 | 5.63 |
| CD36 | NM_001127443 | −0.28 | 47.21 | 11.74 | −35.47 | −2.01 | 5.53 |
| MMP1 | NM_002421 | −0.33 | 69.30 | 31.02 | −38.28 | −1.16 | 5.38 |
| RPA2 | NM_002946 | −0.64 | 16.56 | 1.76 | −14.79 | −3.23 | 5.05 |
| GMPS | NM_003875 | −0.29 | 13.70 | 1.24 | −12.47 | −3.47 | 5.03 |
| STC1 | NM_003155 | −1.12 | 39.40 | 13.31 | −26.09 | −1.57 | 4.96 |
| ACTL6A | NM_004301 | −0.29 | 23.69 | 4.90 | −18.79 | −2.27 | 4.80 |
| DCTN3 | NM_024348 | −0.48 | 19.61 | 3.29 | −16.33 | −2.58 | 4.78 |
| LANCL1 | NM_001136574 | −0.63 | 8.61 | 0.67 | −7.93 | −3.68 | 4.74 |
| PARP3 | NM_001003931 | −0.44 | 12.09 | 1.29 | −10.80 | −3.23 | 4.71 |
| F3 | NM_001993 | −1.18 | 11.90 | 1.27 | −10.63 | −3.23 | 4.70 |
| DCBLD2 | NM_080927 | −0.58 | 63.32 | 39.36 | −23.96 | −0.69 | 4.63 |
| TPRG1L | NM_182752 | −1.03 | 35.20 | 16.26 | −18.95 | −1.11 | 4.39 |
| FBXO28 | NM_001136115 | −0.50 | 6.41 | 0.58 | −5.83 | −3.47 | 4.30 |
| URGCP | NM_001077663 | −0.31 | 7.87 | 0.84 | −7.03 | −3.23 | 4.28 |
| SLC25A44 | NM_014655 | −0.23 | 7.84 | 0.84 | −7.01 | −3.23 | 4.28 |
| FBXO28 | NM_015176 | −0.58 | 6.18 | 0.56 | −5.62 | −3.47 | 4.27 |
| MAF1 | NM_032272 | −0.35 | 18.96 | 5.13 | −13.83 | −1.89 | 4.23 |
| SQSTM1 | NM_003900 | −0.98 | 27.66 | 11.51 | −16.15 | −1.27 | 4.21 |
| M6PR | NM_002355 | −0.85 | 9.08 | 1.18 | −7.90 | −2.94 | 4.19 |
| SAR1B | NM_016103 | −1.28 | 14.67 | 3.25 | −11.41 | −2.17 | 4.13 |
| ZBTB4 | NM_020899 | −1.05 | 12.64 | 2.55 | −10.08 | −2.31 | 4.05 |
| UFD1L | NM_001035247 | −0.98 | 10.48 | 1.75 | −8.72 | −2.58 | 4.05 |
| SLC35AS | NM_017945 | −0.76 | 7.93 | 1.03 | −6.89 | −2.94 | 4.05 |
| RAD23B | NM_002874 | −0.76 | 30.48 | 15.32 | −15.17 | −0.99 | 4.05 |
| MITD1 | NM_138798 | −0.20 | 14.23 | 3.34 | −10.89 | −2.09 | 4.03 |
| UFD1L | NM_005659 | −0.99 | 10.16 | 1.70 | −8.46 | −2.58 | 4.02 |
| PTP4A1 | NM_003463 | −0.46 | 20.89 | 7.77 | −13.12 | −1.43 | 3.98 |
| RRM2 | NM_001034 | −0.73 | 7.13 | 0.93 | −6.21 | −2.94 | 3.95 |
| SERPINB8 | NM_002640 | −0.55 | 6.91 | 0.90 | −6.01 | −2.94 | 3.92 |
| SLC16A7 | NM_004731 | −0.51 | 6.58 | 0.86 | −5.72 | −2.94 | 3.87 |
| GPR137B | NM_003272 | −0.76 | 8.88 | 1.49 | −7.39 | −2.58 | 3.87 |
| MKRN1 | NM_013446 | −1.08 | 12.33 | 2.89 | −9.44 | −2.09 | 3.85 |
| NR8P1 | NM_013392 | −0.76 | 34.15 | 20.71 | −13.44 | −0.72 | 3.82 |
| PFKP | NM_002627 | −1.29 | 30.21 | 17.14 | −13.07 | −0.82 | 3.80 |
| CYTS8 | NM_001033553 | −0.65 | 5.90 | 0.77 | −5.13 | −2.94 | 3.77 |
| LSM5 | NM_012322 | −0.42 | 8.06 | 1.35 | −6.71 | −2.58 | 3.77 |
| FAM103A1 | NM_031452 | −0.89 | 11.30 | 2.65 | −8.65 | −2.09 | 3.75 |
| TPP1 | NM_000391 | −0.68 | 10.99 | 2.58 | −8.42 | −2.09 | 3.72 |
| GTDC1 | NM_001006636 | −1.08 | 6.73 | 1.13 | −5.60 | −2.58 | 3.58 |
| SLC39A6 | NM_012319 | −0.94 | 23.60 | 12.58 | −11.02 | −0.91 | 3.58 |
| ELK3 | NM_005230 | −1.22 | 13.24 | 4.23 | −9.01 | −1.64 | 3.57 |
| MYO10 | NM_012334 | −0.28 | 16.54 | 6.64 | −9.90 | −1.32 | 3.56 |
| VPS45 | NM_007259 | −0.40 | 6.43 | 1.08 | −5.36 | −2.58 | 3.54 |
| PURA | NM_005859 | −1.02 | 14.18 | 5.16 | −9.02 | −1.46 | 3.49 |
| MRPL24 | NM_145729 | −1.24 | 19.55 | 9.82 | −9.73 | −0.99 | 3.43 |
| MGAT2 | NM_002408 | −0.21 | 14.33 | 5.60 | −8.73 | −1.36 | 3.41 |
| ACIN1 | NM_014977 | −0.21 | 14.16 | 5.53 | −8.63 | −1.36 | 3.39 |
| TXNIP | NM_006472 | −1.27 | 27.42 | 17.63 | −9.79 | −0.64 | 3.35 |
| COMMD10 | NM_016144 | −0.30 | 20.00 | 10.66 | −9.34 | −0.91 | 3.35 |
| C1orf9 | NM_014283 | −1.12 | 9.61 | 2.68 | −6.93 | −1.84 | 3.35 |
| CCNDBP1 | NM_012142 | −0.34 | 9.22 | 2.49 | −6.73 | −1.89 | 3.33 |
| UBE2B | NM_003337 | −0.93 | 10.83 | 3.46 | −7.36 | −1.64 | 3.32 |

TABLE 2-continued mRNA Targets Downregulated in SEN Through miRNAs

| Gene Symbol | RefSeq ID | mirSVR Score | SR | SEN | dRPKM | FC | D |
|---|---|---|---|---|---|---|---|
| NTN4 | NM_021229 | −1.22 | 23.64 | 14.28 | −9.36 | −0.73 | 3.31 |
| RSU1 | NM_012425 | −0.21 | 15.87 | 7.28 | −8.59 | −1.12 | 3.30 |
| CENPQ | NM_018132 | −1.27 | 7.49 | 1.76 | −5.74 | −2.09 | 3.28 |
| SLC35F5 | NM_025181 | −1.02 | 22.73 | 13.86 | −8.87 | −0.71 | 3.23 |
| ABR | NM_021962 | −0.34 | 9.37 | 2.89 | −6.48 | −1.70 | 3.18 |
| RAB21 | NM_014999 | −0.43 | 18.73 | 10.40 | −8.33 | −0.85 | 3.17 |
| TBP | NM_003194 | −0.24 | 6.80 | 1.59 | −5.20 | −2.09 | 3.17 |
| GNPDA2 | NM_138335 | −1.25 | 6.75 | 1.58 | −5.17 | −2.09 | 3.16 |
| CDCA4 | NM_145701 | −0.22 | 6.72 | 1.58 | −5.14 | −2.09 | 3.16 |
| ABTB1 | NM_172027 | −0.27 | 11.79 | 4.61 | −7.18 | −1.36 | 3.15 |
| AKTIP | NM_022476 | −0.47 | 17.71 | 9.69 | −8.02 | −0.87 | 3.13 |
| YIPF2 | NM_024029 | −0.25 | 22.38 | 14.13 | −8.25 | −0.66 | 3.12 |
| MAGT1 | NM_032121 | −0.29 | 16.10 | 8.30 | −7.79 | −0.95 | 3.11 |
| GOLGB1 | NM_004487 | −0.34 | 12.27 | 5.16 | −7.11 | −1.25 | 3.09 |
| SFRS4 | NM_005626 | −0.24 | 13.30 | 6.00 | −7.30 | −1.15 | 3.09 |
| TIPARP | NM_015508 | −0.40 | 12.20 | 5.27 | −6.93 | −1.21 | 3.04 |
| CEP120 | NM_153223 | −1.19 | 7.14 | 1.93 | −5.21 | −1.89 | 3.04 |
| CHD9 | NM_025134 | −1.00 | 7.91 | 2.38 | −5.52 | −1.73 | 3.01 |
| KDSR | NM_002035 | −0.29 | 10.46 | 4.09 | −6.37 | −1.36 | 3.00 |
| ATMIN | NM_015251 | −0.60 | 9.05 | 3.12 | −5.93 | −1.54 | 2.99 |
| ZFP91 | NM_053023 | −0.61 | 11.31 | 4.77 | −6.53 | −1.24 | 2.98 |
| LIN7B | NM_022165 | −1.10 | 10.29 | 4.02 | −6.27 | −1.36 | 2.97 |
| UBE3C | NM_014671 | −0.54 | 14.49 | 7.62 | −6.88 | −0.93 | 2.93 |
| ACBD5 | NM_145698 | −0.71 | 9.75 | 3.81 | −5.94 | −1.36 | 2.91 |
| NAP1L1 | NM_004537 | −0.25 | 20.71 | 13.62 | −7.09 | −0.60 | 2.89 |
| NBL1 | NM_182744 | −0.35 | 13.82 | 7.36 | −6.45 | −0.91 | 2.84 |
| FGL2 | NM_006682 | −0.77 | 18.81 | 12.09 | −6.71 | −0.64 | 2.82 |
| RAB11FIP5 | NM_015470 | −1.13 | 12.52 | 6.29 | −6.23 | −0.99 | 2.82 |
| VPS26A | NM_001035260 | −0.69 | 9.11 | 3.56 | −5.55 | −1.36 | 2.82 |
| RBL2 | NM_005611 | −1.08 | 10.07 | 4.35 | −5.72 | −1.21 | 2.79 |
| PDZD11 | NM_016484 | −1.15 | 18.70 | 12.18 | −6.52 | −0.62 | 2.77 |
| SSFA2 | NM_006751 | −0.80 | 12.51 | 6.45 | −6.06 | −0.95 | 2.77 |
| NFAT5 | NM_138713 | −0.21 | 9.93 | 4.34 | −5.59 | −1.20 | 2.76 |
| VPS26A | NM_004896 | −0.71 | 8.63 | 3.37 | −5.26 | −1.36 | 2.75 |
| SSFA2 | NM_001130445 | −0.77 | 12.23 | 6.31 | −5.92 | −0.95 | 2.74 |
| CRK | NM_005206 | −0.90 | 12.79 | 6.82 | −5.97 | −0.91 | 2.73 |
| DPM2 | NM_003863 | −0.26 | 11.72 | 5.89 | −5.83 | −0.99 | 2.73 |
| PPP2R5E | NM_006246 | −1.19 | 10.00 | 4.51 | −5.49 | −1.15 | 2.71 |
| ARL1 | NM_001177 | −0.90 | 18.55 | 12.29 | −6.26 | −0.59 | 2.71 |
| ATP2B1 | NM_001682 | −0.50 | 10.31 | 4.93 | −5.39 | −1.07 | 2.65 |
| CRK | NM_016823 | −0.93 | 11.88 | 6.33 | −5.55 | −0.91 | 2.63 |
| ATP2B1 | NM_001001323 | −0.44 | 10.08 | 4.82 | −5.27 | −1.07 | 2.62 |
| MGLL | NM_001003794 | −0.24 | 16.69 | 10.87 | −5.82 | −0.62 | 2.61 |
| DYNC1U2 | NM_006141 | −1.14 | 16.12 | 10.50 | −5.62 | −0.62 | 2.57 |
| RHOT1 | NM_001033568 | −0.34 | 11.74 | 6.42 | −5.32 | −0.87 | 2.56 |
| RTCD1 | NM_001130841 | −0.43 | 10.85 | 5.78 | −5.07 | −0.91 | 2.51 |
| DNM1L | NM_012062 | −0.53 | 15.16 | 9.87 | −5.28 | −0.62 | 2.48 |
| mir-18a-5p (MIMAT0000072) | | | | | | | |
| TSPYL2 | NM_022117 | −0.30 | 665.60 | 381.06 | −284.54 | −0.80 | 8.19 |
| HIST1H4H | NM_003543 | −0.81 | 62.31 | 8.12 | −54.19 | −2.94 | 6.47 |
| BCAR3 | NM_003567 | −1.25 | 15.32 | 0.96 | −14.56 | −4.02 | 5.57 |
| MSRB2 | NM_012228 | −0.38 | 15.73 | 1.68 | −14.05 | −3.23 | 5.00 |
| NDUFC2 | NM_004549 | −0.75 | 26.15 | 6.13 | −20.02 | −2.09 | 4.80 |
| F3 | NM_001993 | −0.34 | 11.90 | 1.27 | −10.63 | −3.23 | 4.70 |
| ELOVL1 | NM_022821 | −0.72 | 36.66 | 14.33 | −22.34 | −1.36 | 4.68 |
| PCYT1A | NM_005017 | −0.79 | 21.26 | 5.75 | −15.51 | −1.89 | 4.38 |
| EGLN2 | NM_053046 | −0.35 | 10.38 | 1.35 | −9.03 | −2.94 | 4.33 |
| FBXO28 | NM_001136115 | −0.57 | 6.41 | 0.58 | −5.83 | −3.47 | 4.30 |
| FBXO28 | NM_015176 | −0.65 | 6.18 | 0.56 | −5.62 | −3.47 | 4.27 |
| MEF2BNB | NM_001145784 | −0.30 | 12.65 | 2.12 | −10.53 | −2.58 | 4.26 |
| UQCRQ | NM_014402 | −0.79 | 24.50 | 9.58 | −14.93 | −1.36 | 4.13 |
| ZBTB4 | NM_020899 | −1.16 | 12.64 | 2.55 | −10.08 | −2.31 | 4.05 |
| B4GALT7 | NM_007255 | −0.48 | 10.49 | 1.76 | −8.74 | −2.58 | 4.05 |
| FZD8 | NM_031866 | −0.47 | 7.31 | 0.95 | −6.36 | −2.94 | 3.97 |
| PDGFC | NM_016205 | −1.17 | 12.91 | 3.03 | −9.88 | −2.09 | 3.91 |
| EPDR1 | NM_017549 | −0.26 | 30.89 | 17.53 | −13.37 | −0.82 | 3.83 |
| TPP1 | NM_000391 | −0.41 | 10.99 | 2.58 | −8.42 | −2.09 | 3.72 |
| COIL | NM_004645 | −0.23 | 6.85 | 1.15 | −5.73 | −2.58 | 3.60 |
| CA12 | NM_001218 | −0.59 | 18.89 | 8.40 | −10.49 | −1.17 | 3.59 |
| NT5C3L | NM_052935 | −0.24 | 16.39 | 6.40 | −9.98 | −1.36 | 3.59 |
| NAPIL1 | NM_139207 | −0.21 | 23.85 | 12.96 | −10.89 | −0.86 | 3.56 |
| PAPSS2 | NM_001015860 | −0.99 | 20.80 | 10.23 | −10.58 | −1.02 | 3.55 |
| AP3S1 | NM_001284 | −1.26 | 22.10 | 11.77 | −10.32 | −0.91 | 3.49 |
| ACIN1 | NM_014977 | −0.24 | 14.16 | 5.53 | −8.63 | −1.36 | 3.39 |
| SNX5 | NM_014426 | −0.27 | 16.36 | 7.38 | −8.98 | −1.15 | 3.37 |

TABLE 2-continued mRNA Targets Downregulated in SEN Through miRNAs

| Gene Symbol | RefSeq ID | mirSVR Score | SR | SEN | dRPKM | FC | D |
|---|---|---|---|---|---|---|---|
| C1orf9 | NM_014283 | −1.04 | 9.61 | 2.68 | −6.93 | −1.84 | 3.35 |
| NAE1 | NM_003905 | −1.34 | 12.85 | 5.02 | −7.83 | −1.36 | 3.26 |
| TSC22D3 | NM_198057 | −1.10 | 14.84 | 6.69 | −8.15 | −1.15 | 3.24 |
| C9orf114 | NM_016390 | −0.71 | 6.98 | 1.64 | −5.34 | −2.09 | 3.20 |
| GNPDA2 | NM_138335 | −0.87 | 6.75 | 1.58 | −5.17 | −2.09 | 3.16 |
| DDX42 | NM_203499 | −1.09 | 16.50 | 8.51 | −7.99 | −0.95 | 3.15 |
| GCLC | NM_001498 | −0.99 | 12.91 | 5.57 | −7.33 | −1.21 | 3.12 |
| VPS4B | NM_004869 | −0.33 | 11.50 | 4.49 | −7.00 | −1.36 | 3.12 |
| SORBS3 | NM_005775 | −0.31 | 9.12 | 2.92 | −6.20 | −1.64 | 3.10 |
| DUSPS | NM_004419 | −0.28 | 13.31 | 6.00 | −7.31 | −1.15 | 3.09 |
| NDFIP1 | NM_030571 | −0.90 | 15.12 | 7.60 | −7.52 | −0.99 | 3.08 |
| NTSC2 | NM_001134373 | −0.31 | 8.29 | 2.65 | −5.64 | −1.64 | 2.99 |
| HSBP1L1 | NM_001136180 | −0.30 | 10.34 | 4.04 | −6.30 | −1.36 | 2.98 |
| ITGA2 | NM_002203 | −0.63 | 11.52 | 5.01 | −6.50 | −1.20 | 2.96 |
| MKI67IP | NM_032390 | −0.27 | 19.37 | 12.23 | −7.14 | −0.66 | 2.91 |
| PRKAR2A | NM_004157 | −0.47 | 9.79 | 3.82 | −5.96 | −1.36 | 2.91 |
| RBL2 | NM_005611 | −0.61 | 10.07 | 4.35 | −5.72 | −1.21 | 2.79 |
| SEL1L3 | NM_015187 | −0.80 | 17.64 | 11.34 | −6.30 | −0.64 | 2.73 |
| PPP2R5E | NM_006246 | −0.32 | 10.00 | 4.51 | −5.49 | −1.15 | 2.71 |
| ENDOD1 | NM_015036 | −0.24 | 8.28 | 3.23 | −5.04 | −1.36 | 2.70 |
| XPO6 | NM_015171 | −0.35 | 14.64 | 8.92 | −5.71 | −0.71 | 2.61 |
| mir-19a-3p (MIMAT0000073) | | | | | | | |
| IL8 | NM_000584 | −0.46 | 89.60 | 8.90 | −80.69 | −3.33 | 7.16 |
| IL33 | NM_033439 | −0.59 | 35.40 | 1.12 | −34.28 | −4.98 | 7.13 |
| NGFRAP1 | NM_206915 | −0.66 | 34.92 | 3.15 | −31.77 | −3.47 | 6.08 |
| NGFRAP1 | NM_014380 | −0.65 | 31.96 | 3.41 | −28.56 | −3.23 | 5.82 |
| UPF3A | NM_023011 | −0.29 | 18.45 | 1.27 | −17.18 | −3.86 | 5.63 |
| BCAR3 | NM_003567 | −0.22 | 15.52 | 0.96 | −14.56 | −4.02 | 5.57 |
| NDUFB2 | NM_004546 | −0.43 | 68.00 | 30.66 | −37.34 | −1.15 | 5.35 |
| RPS27L | NM_015920 | −0.62 | 78.82 | 47.61 | −31.22 | −0.73 | 5.02 |
| FAM129B | NM_022833 | −1.14 | 87.20 | 56.11 | −31.09 | −0.64 | 5.00 |
| PRKRA | NM_003690 | −0.95 | 15.60 | 1.66 | −13.93 | −3.23 | 4.99 |
| STAMBPL1 | NM_020799 | −0.54 | 14.26 | 1.52 | −12.74 | −3.23 | 4.89 |
| EMC7 | NM_020154 | −0.53 | 46.72 | 20.18 | −26.54 | −1.21 | 4.88 |
| ACTL6A | NM_004301 | −0.52 | 23.69 | 4.50 | −18.79 | −2.27 | 4.80 |
| RAP1B | NM_001010942 | −1.15 | 55.53 | 30.38 | −25.15 | −0.87 | 4.73 |
| PARP3 | NM_001003931 | −0.78 | 12.09 | 1.29 | −10.80 | −3.23 | 4.71 |
| F3 | NM_001993 | −1.04 | 11.90 | 1.27 | −10.63 | −3.23 | 4.70 |
| MEDAG | NM_032849 | −1.18 | 53.08 | 29.21 | −23.87 | −0.86 | 4.66 |
| DCBLD2 | NM_080927 | −0.32 | 63.32 | 39.36 | −23.96 | −0.69 | 4.63 |
| SLC31A2 | NM_001860 | −1.22 | 13.14 | 1.71 | −11.42 | −2.94 | 4.58 |
| CCNC | NM_005190 | −0.41 | 19.08 | 3.95 | −15.13 | −2.27 | 4.53 |
| WDR44 | NM_019045 | −1.34 | 8.12 | 0.73 | −7.39 | −3.47 | 4.51 |
| RALA | NM_005402 | −0.42 | 35.93 | 16.20 | −19.73 | −1.15 | 4.45 |
| TPRG1L | NM_182752 | −0.55 | 35.20 | 16.26 | −18.95 | −1.11 | 4.39 |
| POLE4 | NM_019896 | −0.75 | 18.60 | 4.36 | −14.24 | −2.09 | 4.37 |
| GNAQ | NM_002072 | −0.27 | 17.69 | 4.15 | −13.54 | −2.09 | 4.30 |
| SLC25A44 | NM_014655 | −0.39 | 7.84 | 0.84 | −7.01 | −3.23 | 4.28 |
| FBXO28 | NM_015176 | −0.23 | 6.18 | 0.56 | −5.62 | −3.47 | 4.27 |
| PPTC7 | NM_139283 | −0.70 | 7.60 | 0.81 | −6.79 | −3.23 | 4.25 |
| TSN | NM_004622 | −0.68 | 17.48 | 4.45 | −13.02 | −1.97 | 4.20 |
| FAM69A | NM_001006605 | −0.96 | 8.97 | 1.17 | −7.80 | −2.94 | 4.17 |
| COX6C | NM_004374 | −0.84 | 25.30 | 9.89 | −15.41 | −1.36 | 4.17 |
| ZBTB4 | NM_020899 | −0.90 | 12.64 | 2.55 | −10.08 | −2.31 | 4.05 |
| UFD1L | NM_001035247 | −0.69 | 10.48 | 1.75 | −8.72 | −2.58 | 4.05 |
| RAD23B | NM_002874 | −0.90 | 30.48 | 15.32 | −15.17 | −0.99 | 4.05 |
| UFD1L | NM_005659 | −0.71 | 10.16 | 1.70 | −8.46 | −2.58 | 4.02 |
| PTP4A1 | NM_003463 | −0.21 | 20.89 | 7.77 | −13.12 | −1.43 | 3.98 |
| C2orf76 | NM_001017927 | −0.26 | 13.63 | 3.20 | −10.43 | −2.09 | 3.98 |
| FZD8 | NM_031866 | −0.64 | 7.31 | 0.95 | −6.36 | −2.94 | 3.97 |
| KLHL12 | NM_021633 | −0.74 | 6.98 | 0.91 | −6.07 | −2.94 | 3.93 |
| POU4F1 | NM_006237 | −0.78 | 11.54 | 2.39 | −9.15 | −2.27 | 3.92 |
| BMPER | NM_133468 | −0.73 | 6.86 | 0.89 | −5.96 | −2.94 | 3.91 |
| GPR137B | NM_003272 | −0.95 | 8.88 | 1.49 | −7.39 | −2.58 | 3.87 |
| PIK3IP1 | NM_001135911 | −0.63 | 14.06 | 3.80 | −10.26 | −1.89 | 3.85 |
| RBM26 | NM_022118 | −0.27 | 6.45 | 0.84 | −5.61 | −2.94 | 3.85 |
| RPL27A | NM_000990 | −0.20 | 21.76 | 9.33 | −12.43 | −1.22 | 3.83 |
| NRBP1 | NM_013392 | −0.96 | 34.15 | 20.71 | −13.44 | −0.72 | 3.82 |
| PIK3IP1 | NM_052880 | −0.67 | 13.61 | 3.68 | −9.93 | −1.89 | 3.81 |
| REP15 | NM_001029874 | −0.30 | 11.37 | 2.67 | −8.70 | −2.09 | 3.76 |
| BMP6 | NM_001718 | −1.04 | 22.51 | 10.75 | −11.76 | −1.07 | 3.71 |
| TMEM167B | NM_020141 | −0.55 | 12.24 | 3.31 | −8.93 | −1.89 | 3.68 |
| SUPV3L1 | NM_003171 | −0.43 | 7.33 | 1.23 | −6.10 | −2.58 | 3.67 |
| RAB3B | NM_002867 | −0.90 | 26.41 | 14.89 | −11.52 | −0.83 | 3.62 |
| GNRH1 | NM_001083111 | −0.28 | 10.11 | 2.37 | −7.74 | −2.09 | 3.62 |

TABLE 2-continued mRNA Targets Downregulated in SEN Through miRNAs

| Gene Symbol | RefSeq ID | mirSVR Score | SR | SEN | dRPKM | FC | D |
| --- | --- | --- | --- | --- | --- | --- | --- |
| VDAC3 | NM_005662 | −0.20 | 30.78 | 19.10 | −11.68 | −0.69 | 3.61 |
| GTDC1 | NM_001006636 | −0.23 | 6.73 | 1.13 | −5.60 | −2.58 | 3.58 |
| ELK3 | NM_005230 | −1.08 | 13.24 | 4.23 | −9.01 | −1.64 | 3.57 |
| NCBP2 | NM_007362 | −0.61 | 13.12 | 4.20 | −8.93 | −1.64 | 3.56 |
| NAP1L1 | NM_139207 | −0.49 | 23.85 | 12.96 | −10.89 | −0.88 | 3.56 |
| CCNA2 | NM_001237 | −0.65 | 6.48 | 1.08 | −5.39 | −2.58 | 3.54 |
| SDC1 | NM_002997 | −1.15 | 18.60 | 8.53 | −10.07 | −1.12 | 3.52 |
| PHLDA1 | NM_007350 | −0.43 | 18.83 | 8.73 | −10.10 | −1.11 | 3.52 |
| PURA | NM_005859 | −1.19 | 14.18 | 5.16 | −9.02 | −1.46 | 3.49 |
| RAB13 | NM_002870 | −1.02 | 29.19 | 18.43 | −10.76 | −0.66 | 3.49 |
| SAP18 | NM_005870 | −0.51 | 12.38 | 3.96 | −8.42 | −1.64 | 3.49 |
| PSMD9 | NM_002813 | −0.31 | 12.16 | 3.89 | −8.27 | −1.64 | 3.46 |
| MGAT2 | NM_002408 | −0.39 | 14.33 | 5.60 | −8.73 | −1.36 | 3.41 |
| BOLA3 | NM_212552 | −0.37 | 14.02 | 5.48 | −8.54 | −1.36 | 3.38 |
| TMEM106C | NM_001143842 | −0.41 | 8.15 | 1.91 | −6.24 | −2.09 | 3.37 |
| SNX5 | NM_014426 | −0.89 | 16.36 | 7.38 | −8.98 | −1.15 | 3.37 |
| C1orf9 | NM_014283 | −1.18 | 9.61 | 2.68 | −6.93 | −1.84 | 3.35 |
| ANTXR2 | NM_058172 | −0.40 | 17.71 | 8.68 | −9.03 | −1.03 | 3.34 |
| UBE2O2 | NM_003339 | −1.01 | 10.54 | 3.37 | −7.17 | −1.64 | 3.28 |
| SEC14L1 | NM_003003 | −0.66 | 7.07 | 1.66 | −5.41 | −2.09 | 3.21 |
| ABR | NM_021962 | −0.97 | 9.37 | 2.89 | −6.48 | −1.70 | 3.18 |
| ATXN10 | NM_013236 | −1.11 | 16.33 | 8.20 | −8.12 | −0.99 | 3.18 |
| RAB21 | NM_014999 | −0.45 | 18.73 | 10.40 | −8.33 | −0.85 | 3.17 |
| TROVE2 | NM_004600 | −0.88 | 11.98 | 4.68 | −7.30 | −1.36 | 3.17 |
| UBE2V1 | NM_001032288 | −0.43 | 18.21 | 9.96 | −8.25 | −0.87 | 3.17 |
| NDFIP2 | NM_019080 | −1.04 | 11.68 | 4.56 | −7.12 | −1.36 | 3.14 |
| YTHDF2 | NM_016258 | −1.11 | 9.31 | 2.98 | −6.33 | −1.64 | 3.13 |
| AKTIP | NM_022476 | −0.36 | 17.71 | 9.69 | −8.02 | −0.87 | 3.13 |
| GCLC | NM_001498 | −0.23 | 12.91 | 5.57 | −7.33 | −1.21 | 3.12 |
| VPS4B | NM_004869 | −1.18 | 11.50 | 4.49 | −7.00 | −1.36 | 3.12 |
| GLRX5 | NM_016417 | −1.06 | 15.48 | 7.78 | −7.70 | −0.99 | 3.11 |
| SETD7 | NM_030648 | −0.31 | 12.92 | 5.63 | −7.30 | −1.20 | 3.11 |
| NDFIP1 | NM_030571 | −1.10 | 15.12 | 7.60 | −7.52 | −0.99 | 3.08 |
| SPRY2 | NM_005842 | −0.27 | 11.04 | 4.32 | −6.73 | −1.36 | 3.07 |
| UBA3 | NM_003968 | −1.26 | 20.77 | 12.89 | −7.88 | −0.69 | 3.06 |
| TIPARP | NM_015508 | −1.06 | 12.20 | 5.27 | −6.93 | −1.21 | 3.04 |
| INSIG1 | NM_196337 | −1.01 | 12.38 | 5.58 | −6.80 | −1.15 | 2.99 |
| ATMIN | NM_015251 | −1.02 | 9.05 | 3.12 | −5.93 | −1.54 | 2.99 |
| HNRNPF | NM_001098206 | −1.10 | 22.48 | 14.90 | −7.58 | −0.59 | 2.98 |
| ZFP91 | NM_053023 | −0.65 | 11.31 | 4.77 | −6.53 | −1.24 | 2.98 |
| ARL6IP1 | NM_015161 | −0.76 | 10.29 | 4.02 | −6.27 | −1.36 | 2.98 |
| ITGA2 | NM_002203 | −0.84 | 11.52 | 5.01 | −6.50 | −1.21 | 2.96 |
| ACBD5 | NM_145698 | −1.14 | 9.75 | 3.81 | −5.94 | −1.36 | 2.91 |
| NAP1L1 | NM_004537 | −0.36 | 20.71 | 13.62 | −7.09 | −0.60 | 2.89 |
| INSIG1 | NM_005542 | −1.02 | 11.18 | 5.04 | −6.14 | −1.15 | 2.86 |
| FMR1 | NM_002024 | −1.10 | 12.33 | 6.18 | −6.13 | −0.99 | 2.80 |
| UTRN | NM_007124 | −0.22 | 11.04 | 5.13 | −5.91 | −1.11 | 2.79 |
| PIP4K2B | NM_003559 | −0.30 | 7.68 | 2.65 | −5.03 | −1.54 | 2.79 |
| SECISBP2L | NM_014701 | −0.70 | 11.40 | 5.61 | −5.80 | −1.02 | 2.73 |
| TMEM189-UBE2V1 | NM_199203 | −0.43 | 13.31 | 7.28 | −6.03 | −0.87 | 2.73 |
| SEL1L3 | NM_015187 | −0.81 | 17.64 | 11.34 | −6.30 | −0.64 | 2.73 |
| PPP2R5E | NM_006246 | −1.23 | 10.00 | 4.51 | −5.49 | −1.15 | 2.71 |
| IER5L | NM_203434 | −0.24 | 16.24 | 10.06 | −6.16 | −0.69 | 2.71 |
| CS | NM_004077 | −0.76 | 13.05 | 7.14 | −5.91 | −0.87 | 2.71 |
| DYNC1LI2 | NM_006141 | −0.93 | 16.12 | 10.50 | −5.62 | −0.62 | 2.57 |
| NECAP1 | NM_015509 | −0.31 | 10.96 | 5.85 | −5.13 | −0.91 | 2.53 |
| RTCD1 | NM_001130841 | −0.29 | 10.85 | 5.78 | −5.07 | −0.91 | 2.51 |
| RUFY1 | NM_025158 | −0.52 | 10.85 | 5.78 | −5.07 | −0.91 | 2.51 |
| DNM1L | NM_012062 | −0.27 | 15.16 | 9.87 | −5.28 | −0.62 | 2.48 |
| TNIP1 | NM_006058 | −0.48 | 13.47 | 8.36 | −5.11 | −0.69 | 2.45 |
| mir-20a-5p (MIMAT0000075) | | | | | | | |
| TFIP2 | NM_006528 | −1.23 | 528.90 | 225.72 | −303.17 | −1.23 | 8.34 |
| IL8 | NM_000584 | −1.18 | 89.60 | 8.90 | −80.69 | −3.33 | 7.16 |
| INHBA | NM_002192 | −0.36 | 282.13 | 177.25 | −104.88 | −0.67 | 6.75 |
| NGFRAP1 | NM_014380 | −0.35 | 31.96 | 3.41 | −28.56 | −3.23 | 5.82 |
| UPF3A | NM_023011 | −0.31 | 18.45 | 1.27 | −17.18 | −3.86 | 5.63 |
| CD36 | NM_001127443 | −0.28 | 47.21 | 11.74 | −35.47 | −2.01 | 5.53 |
| MMP1 | NM_002421 | −0.31 | 69.30 | 31.02 | −38.28 | −1.16 | 5.38 |
| RPA2 | NM_002946 | −0.63 | 16.56 | 1.76 | −14.79 | −3.23 | 5.05 |
| GMPS | NM_003875 | −0.29 | 13.70 | 1.24 | −12.47 | −3.47 | 5.03 |
| STC1 | NM_003155 | −1.12 | 39.40 | 13.31 | −26.09 | −1.57 | 4.96 |
| ACTL6A | NM_004301 | −0.29 | 23.69 | 4.90 | −18.79 | −2.27 | 4.80 |
| DCTN3 | NM_024348 | −0.48 | 19.61 | 3.29 | −16.33 | −2.58 | 4.78 |
| LANCL1 | NM_001136574 | −0.63 | 2.61 | 0.67 | −7.93 | −3.68 | 4.74 |
| PARP3 | NM_001003931 | −0.43 | 12.09 | 1.29 | −10.80 | −3.23 | 4.71 |

TABLE 2-continued mRNA Targets Downregulated in SEN Through miRNAs

| Gene Symbol | RefSeq ID | mirSVR Score | SR | SEN | dRPKM | FC | D |
|---|---|---|---|---|---|---|---|
| F3 | NM_001993 | −1.18 | 11.90 | 1.27 | −10.63 | −3.23 | 4.70 |
| DCBLD2 | NM_080927 | −0.58 | 63.32 | 39.36 | −23.96 | −0.69 | 4.63 |
| TPRG1L | NM_182752 | −1.02 | 35.20 | 16.26 | −18.95 | −1.11 | 4.39 |
| NDUFA4 | NM_002489 | −1.00 | 41.52 | 22.13 | −19.39 | −0.91 | 4.37 |
| ADI1 | NM_018269 | −0.42 | 20.08 | 5.43 | −14.65 | −1.89 | 4.31 |
| FBXO28 | NM_001136115 | −0.50 | 6.41 | 0.58 | −5.83 | −3.47 | 4.30 |
| URGCP | NM_001077663 | −0.31 | 7.87 | 0.84 | −7.03 | −3.23 | 4.28 |
| SLC25A44 | NM_014655 | −0.23 | 7.84 | 0.84 | −7.01 | −3.23 | 4.28 |
| FBXO28 | NM_015176 | −0.58 | 6.18 | 0.56 | −5.62 | −3.47 | 4.27 |
| UBA6 | NM_018227 | −0.35 | 15.66 | 3.30 | −12.37 | −2.25 | 4.27 |
| MAF1 | NM_032272 | −0.36 | 18.96 | 5.13 | −13.63 | −1.89 | 4.23 |
| SQSTM1 | NM_003900 | −0.98 | 27.66 | 11.51 | −16.15 | −1.27 | 4.21 |
| M6PR | NM_002355 | −0.85 | 9.08 | 1.18 | −7.90 | −2.94 | 4.19 |
| SAR1B | NM_016103 | −1.28 | 14.67 | 3.25 | −11.41 | −2.17 | 4.13 |
| ZBTB4 | NM_020899 | −1.05 | 12.64 | 2.55 | −10.08 | −2.31 | 4.05 |
| UFD1L | NM_001035247 | −0.98 | 10.48 | 1.75 | −8.72 | −2.58 | 4.05 |
| SLC3SA5 | NM_017945 | −0.75 | 7.93 | 1.03 | −6.89 | −2.94 | 4.05 |
| RAD23B | NM_002874 | −0.76 | 30.48 | 15.32 | −15.17 | −0.99 | 4.05 |
| MITD1 | NM_138798 | −0.20 | 14.23 | 3.34 | −10.89 | −2.09 | 4.03 |
| UFD1L | NM_005659 | −0.99 | 10.16 | 1.70 | −8.46 | −2.58 | 4.02 |
| PTP4A1 | NM_003463 | −0.46 | 20.89 | 7.77 | −13.12 | −1.43 | 3.98 |
| RRM2 | NM_001034 | −0.73 | 7.13 | 0.93 | −6.21 | −2.94 | 3.95 |
| SERPINB8 | NM_002640 | −0.52 | 6.91 | 0.90 | −6.01 | −2.94 | 3.92 |
| SLC16A7 | NM_004731 | −0.51 | 6.58 | 0.86 | −5.72 | −2.94 | 3.87 |
| GPR137B | NM_003272 | −0.76 | 8.88 | 1.49 | −7.39 | −2.58 | 3.87 |
| ERRFI1 | NM_018948 | −0.41 | 12.41 | 2.91 | −9.50 | −2.09 | 3.86 |
| MKRN1 | NM_013446 | −1.08 | 12.33 | 2.89 | −9.44 | −2.09 | 3.86 |
| NRBP1 | NM_013392 | −0.76 | 34.15 | 20.71 | −13.44 | −0.72 | 3.82 |
| PFKP | NM_002627 | −1.29 | 30.21 | 17.14 | −13.07 | −0.82 | 3.80 |
| CYTSB | NM_001033553 | −0.65 | 5.90 | 0.77 | −5.13 | −2.94 | 3.77 |
| LSM5 | NM_012322 | −0.42 | 8.06 | 1.35 | −6.71 | −2.58 | 3.77 |
| LYRM5 | NM_001001660 | −0.87 | 11.41 | 2.67 | −8.73 | −2.09 | 3.76 |
| GTDC1 | NM_001006636 | −1.08 | 6.73 | 1.13 | −5.60 | −2.58 | 3.58 |
| SLC39A6 | NM_012319 | −0.94 | 23.60 | 12.58 | −11.02 | −0.91 | 3.58 |
| ELK3 | NM_005230 | −1.22 | 13.24 | 4.23 | −9.01 | −1.64 | 3.57 |
| MYO10 | NM_012334 | −0.28 | 16.54 | 6.64 | −9.90 | −1.32 | 3.56 |
| PURA | NM_005859 | −1.02 | 14.18 | 5.16 | −9.02 | −1.46 | 3.49 |
| TXNDC12 | NM_015913 | −0.64 | 14.57 | 5.70 | −8.88 | −1.36 | 3.43 |
| MRPL24 | NM_145729 | −1.24 | 19.55 | 9.82 | −9.73 | −0.99 | 3.43 |
| MGAT2 | NM_002408 | −0.21 | 14.33 | 5.60 | −8.73 | −1.36 | 3.41 |
| ACIN1 | NM_014977 | −0.21 | 14.16 | 5.53 | −8.63 | −1.36 | 3.39 |
| C4orf33 | NM_001099783 | −0.81 | 8.15 | 1.91 | −6.24 | −2.09 | 3.37 |
| TXNIP | NM_006472 | −1.27 | 27.42 | 17.63 | −9.79 | −0.64 | 3.35 |
| COMMD10 | NM_016144 | −0.30 | 20.00 | 10.66 | −9.34 | −0.91 | 3.35 |
| C1orf9 | NM_014283 | −1.06 | 9.61 | 2.68 | −6.93 | −1.84 | 3.35 |
| CCND8P1 | NM_012142 | −0.34 | 9.22 | 2.49 | −6.73 | −1.89 | 3.33 |
| UBE2B | NM_003337 | −0.93 | 10.83 | 3.46 | −7.36 | −1.64 | 3.32 |
| NTN4 | NM_021229 | −1.21 | 23.64 | 14.28 | −9.36 | −0.73 | 3.31 |
| RSU1 | NM_012425 | −0.21 | 15.87 | 7.28 | −8.59 | −1.12 | 3.30 |
| CENPQ | NM_018132 | −1.27 | 7.49 | 1.76 | −5.74 | −2.09 | 3.28 |
| COPG2 | NM_012133 | −0.46 | 7.47 | 1.75 | −5.72 | −2.09 | 3.27 |
| SLC35F5 | NM_025181 | −1.02 | 22.73 | 13.86 | −8.87 | −0.71 | 3.23 |
| ABR | NM_021962 | −0.34 | 9.37 | 2.89 | −6.48 | −1.70 | 3.18 |
| RAB21 | NM_014999 | −0.43 | 18.73 | 10.40 | −8.33 | −0.85 | 3.17 |
| TBP | NM_003194 | −0.24 | 6.80 | 1.59 | −5.20 | −2.09 | 3.17 |
| GNPDA2 | NM_138335 | −1.25 | 6.75 | 1.58 | −5.17 | −2.09 | 3.16 |
| CDCA4 | NM_145701 | −0.22 | 6.72 | 1.58 | −5.14 | −2.09 | 3.16 |
| ABTB1 | NM_172027 | −0.27 | 11.79 | 4.61 | −7.18 | −1.36 | 3.15 |
| HMGN4 | NM_006353 | −0.78 | 6.58 | 1.54 | −5.04 | −2.09 | 3.13 |
| AKTIP | NM_022476 | −0.47 | 17.71 | 9.69 | −8.02 | −0.87 | 3.13 |
| YIPF2 | NM_024029 | −0.25 | 22.38 | 14.13 | −8.25 | −0.66 | 3.12 |
| MAGT1 | NM_032121 | −0.29 | 16.10 | 8.30 | −7.79 | −0.95 | 3.11 |
| GOLGB1 | NM_004487 | −0.34 | 12.27 | 5.16 | −7.11 | −1.25 | 3.09 |
| SFRS4 | NM_005626 | −0.24 | 13.30 | 6.00 | −7.30 | −1.15 | 3.09 |
| DCAF16 | NM_017741 | −0.85 | 7.40 | 2.00 | −5.40 | −1.89 | 3.08 |
| TIPARP | NM_015508 | −0.40 | 12.20 | 5.27 | −6.93 | −1.21 | 3.04 |
| CEP120 | NM_153223 | −1.19 | 7.14 | 1.93 | −5.21 | −1.89 | 3.04 |
| CHD9 | NM_025134 | −1.00 | 7.91 | 2.38 | −5.52 | −1.73 | 3.01 |
| KDSR | NM_002035 | −0.29 | 10.46 | 4.09 | −6.37 | −1.36 | 3.00 |
| ATMIN | NM_015251 | −0.60 | 9.05 | 3.12 | −5.93 | −1.54 | 2.99 |
| ZFP91 | NM_053023 | −0.61 | 11.31 | 4.77 | −6.53 | −1.24 | 2.98 |
| LIN7B | NM_022165 | −1.10 | 10.29 | 4.02 | −6.27 | −1.36 | 2.97 |
| UBE3C | NM_014671 | −0.54 | 14.49 | 7.62 | −6.88 | −0.93 | 2.93 |
| AC8D5 | NM_145698 | −0.71 | 9.75 | 3.81 | −5.94 | −1.36 | 2.91 |
| NAP1L1 | NM_004537 | −0.24 | 20.71 | 13.62 | −7.09 | −0.60 | 2.89 |
| NBL1 | NM_182744 | −0.36 | 13.82 | 7.36 | −6.45 | −0.91 | 2.84 |

TABLE 2-continued mRNA Targets Downregulated in SEN Through miRNAs

| Gene Symbol | RefSeq ID | mirSVR Score | SR | SEN | dRPKM | FC | D |
|---|---|---|---|---|---|---|---|
| FGL2 | NM_006682 | −0.77 | 18.81 | 12.09 | −6.71 | −0.64 | 2.82 |
| RAB11FIP5 | NM_015470 | −1.13 | 12.52 | 6.29 | −6.23 | −0.99 | 2.82 |
| VPS26A | NM_001035260 | −0.69 | 9.11 | 3.56 | −5.55 | −1.36 | 2.82 |
| MAPKSP1 | NM_021970 | −0.30 | 9.07 | 3.55 | −5.53 | −1.36 | 2.81 |
| RBL2 | NM_005611 | −1.07 | 10.07 | 4.35 | −5.72 | −1.21 | 2.79 |
| PDZD11 | NM_016484 | −1.15 | 18.70 | 12.18 | −6.52 | −0.62 | 2.77 |
| SSFA2 | NM_006751 | −0.80 | 12.51 | 6.45 | −6.06 | −0.95 | 2.77 |
| VPS26A | NM_004896 | −0.70 | 8.63 | 3.37 | −5.26 | −1.36 | 2.75 |
| SSFA2 | NM_001130445 | −0.77 | 12.23 | 6.31 | −5.92 | −0.95 | 2.74 |
| CRK | NM_005206 | −0.91 | 12.79 | 6.82 | −5.97 | −0.91 | 2.73 |
| DPM2 | NM_003863 | −0.26 | 11.72 | 5.89 | −5.83 | −0.99 | 2.73 |
| PPP2R5E | NM_006276 | −1.19 | 10.00 | 4.51 | −5.49 | −1.15 | 2.71 |
| ARL1 | NM_001177 | −0.90 | 18.55 | 12.29 | −6.26 | −0.59 | 2.71 |
| ATP2B1 | NM_001682 | −0.52 | 10.31 | 4.93 | −5.39 | −1.07 | 2.65 |
| CRK | NM_016823 | −0.93 | 11.88 | 6.33 | −5.55 | −0.91 | 2.63 |
| ATP2B1 | NM_001001323 | −0.46 | 10.08 | 4.82 | −5.27 | −1.07 | 2.62 |
| MGLL | NM_001003794 | −0.24 | 16.69 | 10.87 | −5.82 | −0.62 | 2.61 |
| DYNC1LI2 | NM_006141 | −1.14 | 16.12 | 10.50 | −5.62 | −0.62 | 2.57 |
| RHOT1 | NM_001033568 | −0.34 | 11.74 | 6.42 | −5.32 | −0.87 | 2.56 |
| RTCD1 | NM_001130841 | −0.62 | 10.85 | 5.78 | −5.07 | −0.91 | 2.51 |
| DNM1L | NM_012062 | −0.50 | 15.16 | 9.87 | −5.28 | −0.62 | 2.48 |
| mir-100-5p (MIMAT0000098) | | | | | | | |
| RAP1B | NM_001010942 | −1.14 | 55.53 | 30.38 | −25.15 | −0.87 | 4.73 |
| FZD5 | NM_031866 | −1.14 | 7.31 | 0.95 | −6.36 | −2.94 | 3.97 |
| EPDR1 | NM_017549 | −0.37 | 30.89 | 17.53 | −13.37 | −0.82 | 3.83 |
| PL-5283 | NM_001130929 | −0.39 | 13.47 | 3.65 | −9.83 | −1.89 | 3.80 |
| SIAH2 | NM_005067 | −1.15 | 6.92 | 1.16 | −5.76 | −2.58 | 3.61 |
| TSC22D3 | NM_198057 | −0.60 | 14.84 | 6.69 | −8.15 | −1.15 | 3.24 |
| C9orf123 | NM_033428 | −0.92 | 9.37 | 3.66 | −5.71 | −1.36 | 2.86 |
| mir-125b-5p (MIMAT0000423) | | | | | | | |
| RPA2 | NM_002946 | −0.41 | 16.56 | 1.76 | −14.79 | −3.23 | 5.05 |
| PRKRA | NM_003690 | −0.22 | 15.60 | 1.66 | −13.93 | −3.23 | 4.99 |
| STC1 | NM_003155 | −0.56 | 39.40 | 13.31 | −26.09 | −1.57 | 4.96 |
| ACTL6A | NM_004301 | −0.28 | 23.69 | 4.90 | −18.79 | −2.27 | 4.80 |
| SNRPB | NM_003091 | −0.62 | 29.19 | 7.90 | −21.29 | −1.89 | 4.80 |
| TMEM50A | NM_014313 | −0.44 | 43.86 | 19.78 | −24.09 | −1.15 | 4.73 |
| PLIN3 | NM_005817 | −0.32 | 38.73 | 16.86 | −21.86 | −1.20 | 4.61 |
| MLF2 | NM_005439 | −0.34 | 24.20 | 6.55 | −17.65 | −1.89 | 4.55 |
| CCNC | NM_005190 | −0.42 | 19.08 | 3.95 | −15.13 | −2.27 | 4.53 |
| RABL6 | NM_024718 | −0.36 | 9.10 | 0.97 | −8.13 | −3.23 | 4.42 |
| DSTN | NM_006870 | −0.22 | 56.15 | 35.73 | −20.41 | −0.65 | 4.40 |
| ANPEP | NM_001150 | −0.32 | 58.88 | 39.09 | −19.79 | −0.59 | 4.35 |
| ESRRA | NM_004451 | −0.93 | 10.49 | 1.37 | −9.13 | −2.94 | 4.34 |
| SLC35A5 | NM_017945 | −0.24 | 7.93 | 1.03 | −6.89 | −2.94 | 4.05 |
| TIMM17B | NM_005834 | −0.28 | 13.63 | 3.20 | −10.43 | −2.09 | 3.98 |
| RRM2 | NM_001034 | −0.35 | 7.13 | 0.93 | −6.21 | −2.94 | 3.95 |
| TRIB1 | NM_025195 | −0.30 | 6.42 | 0.84 | −5.58 | −2.94 | 3.85 |
| HAX1 | NM_006118 | −0.25 | 19.83 | 7.75 | −12.08 | −1.36 | 3.84 |
| TCTA | NM_022171 | −0.26 | 8.44 | 1.41 | −7.03 | −2.58 | 3.82 |
| ZNF828 | NM_001164145 | −0.96 | 6.17 | 0.80 | −5.36 | −2.94 | 3.84 |
| KIAAD174 | NM_014761 | −0.65 | 20.94 | 9.05 | −11.90 | −1.21 | 3.77 |
| OSBPL9 | NM_148909 | −1.22 | 9.94 | 2.33 | −7.61 | −2.09 | 3.60 |
| NT5C3L | NM_052935 | −0.45 | 16.39 | 6.40 | −9.98 | −1.36 | 3.59 |
| TBC1D1 | NM_015173 | −0.40 | 10.47 | 2.67 | −7.80 | −1.97 | 3.56 |
| PSMD9 | NM_002813 | −0.95 | 12.16 | 3.89 | −8.27 | −1.64 | 3.46 |
| TXNIP | NM_006472 | −0.45 | 27.42 | 17.63 | −9.79 | −0.64 | 3.35 |
| PRRC1 | NM_130809 | −0.96 | 10.49 | 3.24 | −7.25 | −1.70 | 3.32 |
| FIBP | NM_198897 | −0.83 | 19.64 | 10.47 | −9.17 | −0.91 | 3.32 |
| MRPL10 | NM_145255 | −0.21 | 7.40 | 1.74 | −5.67 | −2.09 | 3.26 |
| TSC22D3 | NM_198057 | −0.71 | 14.84 | 6.69 | −8.15 | −1.15 | 3.24 |
| MED15 | NM_015889 | −0.22 | 11.93 | 4.66 | −7.27 | −1.36 | 3.17 |
| ABTB1 | NM_172027 | −0.30 | 11.79 | 4.61 | −7.18 | −1.36 | 3.15 |
| DDX42 | NM_203499 | −0.48 | 16.50 | 8.51 | −7.99 | −0.95 | 3.15 |
| ZSWIM6 | NM_020928 | −1.26 | 8.94 | 2.76 | −6.18 | −1.70 | 3.13 |
| VPS4B | NM_004869 | −1.11 | 11.50 | 4.49 | −7.00 | −1.36 | 3.12 |
| GOLGB1 | NM_004487 | −0.23 | 12.27 | 5.16 | −7.11 | −1.25 | 3.09 |
| OAZ2 | NM_002537 | −0.40 | 14.86 | 7.92 | −6.94 | −0.91 | 2.94 |
| PSMG3 | NM_001134340 | −0.22 | 9.97 | 3.90 | −6.07 | −1.36 | 2.93 |
| TAF9B | NM_015975 | −1.04 | 8.67 | 3.39 | −5.28 | −1.36 | 2.76 |
| HAS1 | NM_001523 | −0.35 | 16.13 | 10.18 | −5.95 | −0.66 | 2.66 |

TABLE 2-continued mRNA Targets Downregulated in SEN Through miRNAs

| Gene Symbol | RefSeq ID | mirSVR Score | SR | SEN | dRPKM | FC | D |
|---|---|---|---|---|---|---|---|
| MRPS10 | NM_018141 | −0.21 | 15.73 | 9.93 | −5.80 | −0.66 | 2.62 |
| SLC39A9 | NM_018375 | −0.84 | 13.90 | 8.43 | −5.47 | −0.72 | 2.56 |
| RTCD1 | NM_001130841 | −0.43 | 10.85 | 5.78 | −5.07 | −0.91 | 2.51 |
| mir-92a-1-Sp (MIMAT0004507) | | | | | | | |
| H2AFZ | NM_002106 | −0.30 | 68.35 | 35.26 | −33.09 | −0.95 | 5.14 |
| RAP1B | NM_001010942 | −0.22 | 55.53 | 30.38 | −25.15 | −0.87 | 4.73 |
| TMEM5QA | NM_014313 | −1.03 | 43.86 | 19.78 | −24.09 | −1.15 | 4.73 |
| ATPIF1 | NM_178191 | −0.24 | 25.56 | 7.88 | −17.67 | −1.70 | 4.48 |
| MEA1 | NM_014623 | −0.51 | 44.85 | 24.54 | −20.31 | −0.87 | 4.43 |
| ZFAND3 | NM_021943 | −0.20 | 8.55 | 0.91 | −7.63 | −3.23 | 4.36 |
| EGLN2 | NM_053046 | −0.37 | 10.38 | 1.35 | −9.03 | −2.94 | 4.33 |
| LOC729991 | NM_001145784 | −0.46 | 12.65 | 2.12 | −10.53 | −2.58 | 4.26 |
| NR3C1 | NM_001020825 | −0.64 | 26.80 | 10.96 | −15.84 | −1.29 | 4.19 |
| PA2G4 | NM_006191 | −0.81 | 22.68 | 8.09 | −14.59 | −1.49 | 4.14 |
| MRPS18B | NM_014046 | −0.25 | 18.57 | 5.94 | −12.63 | −1.64 | 4.01 |
| PTP4A1 | NM_003463 | −0.51 | 20.89 | 7.77 | −13.12 | −1.43 | 3.98 |
| SERPINB8 | NM_002640 | −0.49 | 6.91 | 0.90 | −6.01 | −2.94 | 3.92 |
| TCTA | NM_022171 | −0.21 | 8.44 | 1.41 | −7.03 | −2.58 | 3.82 |
| CYTSB | NM_001033553 | −0.21 | 5.90 | 0.77 | −5.13 | −2.94 | 3.77 |
| TPP1 | NM_000391 | −0.55 | 10.99 | 2.58 | −8.42 | −2.09 | 3.72 |
| HIST1H28M | NM_003521 | −0.29 | 17.42 | 6.81 | −10.61 | −1.36 | 3.67 |
| IP6K2 | NM_001005911 | −0.59 | 10.42 | 2.44 | −7.98 | −2.09 | 3.65 |
| ABCF1 | NM_001025091 | −0.27 | 18.69 | 7.89 | −10.80 | −1.24 | 3.65 |
| SIAH2 | NM_005067 | −0.63 | 6.92 | 1.16 | −5.76 | −2.58 | 3.61 |
| OSBPL9 | NM_148909 | −0.54 | 9.94 | 2.33 | −7.61 | −2.09 | 3.60 |
| IP6K2 | NM_001146179 | −0.56 | 9.89 | 2.32 | −7.57 | −2.09 | 3.59 |
| C17orf49 | NM_001142798 | −0.24 | 20.07 | 10.08 | −9.99 | −0.99 | 3.47 |
| AIDA | NM_022831 | −0.21 | 24.98 | 15.15 | −9.83 | −0.72 | 3.38 |
| DPT | NM_001937 | −1.04 | 7.49 | 1.76 | −5.74 | −2.09 | 3.28 |
| CCDC92 | NM_025140 | −0.33 | 7.22 | 1.69 | −5.53 | −2.09 | 3.23 |
| NOL10 | NM_024894 | −0.59 | 14.08 | 6.08 | −8.00 | −1.21 | 3.23 |
| MED15 | NM_015889 | −0.24 | 11.93 | 4.66 | −7.27 | −1.36 | 3.17 |
| C20orf132 | NM_213632 | −0.24 | 11.75 | 4.59 | −7.16 | −1.36 | 3.15 |
| AKTIP | NM_022476 | −0.25 | 17.71 | 9.69 | −8.02 | −0.87 | 3.13 |
| TPBG | NM_006670 | −0.21 | 12.96 | 6.27 | −6.71 | −1.05 | 2.94 |
| SRR | NM_021947 | −0.95 | 9.41 | 3.68 | −5.73 | −1.36 | 2.86 |
| POGK | NM_017542 | −0.87 | 7.39 | 2.36 | −5.03 | −1.64 | 2.85 |
| DDX24 | NM_020414 | −0.26 | 20.20 | 13.39 | −6.81 | −0.59 | 2.83 |
| DPM2 | NM_003863 | −0.32 | 11.72 | 5.89 | −5.83 | −0.99 | 2.73 |
| let-7a-2-3p (MIMAT0010195) | | | | | | | |
| IL8 | NM_000584 | −0.31 | 89.60 | 8.90 | −80.69 | −3.33 | 7.16 |
| IL33 | NM_033439 | −1.22 | 35.40 | 1.12 | −34.28 | −4.98 | 7.13 |
| RPS25 | NM_001028 | −1.27 | 268.93 | 142.20 | −126.74 | −0.92 | 7.05 |
| SFRS13A | NM_054016 | −0.29 | 14.40 | 0.99 | −13.41 | −3.86 | 5.38 |
| NDUFB2 | NM_004546 | −0.37 | 68.00 | 30.66 | −37.34 | −1.15 | 5.35 |
| H2AFZ | NM_002106 | −0.26 | 68.35 | 35.26 | −33.09 | −0.95 | 5.14 |
| RPA2 | NM_002946 | −0.24 | 16.56 | 1.76 | −14.79 | −3.23 | 5.05 |
| SNRPB | NM_198216 | −0.67 | 33.43 | 9.04 | −24.38 | −1.89 | 4.98 |
| STC1 | NM_003155 | −1.19 | 39.40 | 13.31 | −26.09 | −1.57 | 4.96 |
| FGFR1OP | NM_007045 | −1.26 | 15.11 | 1.61 | −13.50 | −3.23 | 4.95 |
| SRGN | NM_002727 | −0.72 | 64.01 | 36.31 | −27.70 | −0.82 | 4.86 |
| NME1 | NM_198175 | −0.30 | 52.74 | 26.50 | −26.24 | −0.99 | 4.82 |
| SNRP8 | NM_003091 | −0.82 | 29.19 | 7.90 | −21.29 | −1.89 | 4.80 |
| RAP1B | NM_001010942 | −0.48 | 55.53 | 30.38 | −25.15 | −0.87 | 4.73 |
| SERPINE2 | NM_006216 | −0.41 | 69.92 | 44.34 | −25.57 | −0.66 | 4.72 |
| PARP3 | NM_001003931 | −0.66 | 12.09 | 1.29 | −10.80 | −3.23 | 4.71 |
| F3 | NM_001993 | −0.29 | 11.90 | 1.27 | −10.63 | −3.23 | 4.70 |
| ELOVL1 | NM_022821 | −0.40 | 36.66 | 14.33 | −22.34 | −1.36 | 4.68 |
| TNFRSF10D | NM_003840 | −0.26 | 57.91 | 33.52 | −24.39 | −0.79 | 4.68 |
| ANKRD1 | NM_014391 | −0.21 | 30.17 | 10.76 | −19.40 | −1.49 | 4.53 |
| BASP1 | NM_006317 | −0.59 | 50.43 | 28.72 | −21.71 | −0.81 | 4.51 |
| WDR44 | NM_019045 | −0.40 | 8.12 | 0.73 | −7.39 | −3.47 | 4.51 |
| TXNDC11 | NM_015914 | −0.23 | 9.35 | 1.00 | −8.35 | −3.23 | 4.45 |
| MEA1 | NM_014623 | −1.13 | 44.85 | 24.54 | −20.31 | −0.87 | 4.43 |
| ESRRA | NM_004451 | −0.69 | 10.49 | 1.37 | −9.13 | −2.94 | 4.34 |
| ADI1 | NM_018269 | −0.52 | 20.08 | 5.43 | −14.65 | −1.89 | 4.31 |
| UBA6 | NM_016227 | −0.23 | 15.66 | 3.30 | −12.37 | −2.25 | 4.27 |
| GOSR2 | NM_054022 | −0.48 | 12.34 | 2.07 | −10.27 | −2.58 | 4.24 |
| CCDC51 | NM_024661 | −0.24 | 12.03 | 2.02 | −10.02 | −2.58 | 4.21 |
| SAR1B | NM_016103 | −0.38 | 14.67 | 3.25 | −11.41 | −2.17 | 4.13 |
| COPS7A | NM_016319 | −0.58 | 26.65 | 11.51 | −15.14 | −1.21 | 4.10 |
| KCTD9 | NM_017634 | −0.27 | 26.65 | 11.60 | −15.04 | −1.20 | 4.09 |
| RAD23B | NM_002874 | −0.66 | 30.48 | 15.32 | −15.17 | −0.99 | 4.05 |
| GNG5 | NM_005274 | −0.99 | 41.76 | 26.36 | −15.40 | −0.66 | 4.00 |

TABLE 2-continued mRNA Targets Downregulated in SEN Through miRNAs

| Gene Symbol | RefSeq ID | mirSVR Score | SR | SEN | dRPKM | FC | D |
|---|---|---|---|---|---|---|---|
| PTP4A1 | NM_003463 | −0.82 | 20.89 | 7.77 | −13.12 | −1.43 | 3.98 |
| FZD8 | NM_031866 | −0.59 | 7.31 | 0.95 | −6.36 | −2.94 | 3.97 |
| SERPINB8 | NM_002640 | −0.92 | 6.91 | 0.90 | −6.01 | −2.94 | 3.92 |
| PDGFC | NM_016205 | −0.41 | 12.91 | 3.03 | −9.88 | −2.09 | 3.91 |
| GPR137B | NM_003272 | −0.43 | 8.88 | 1.49 | −7.39 | −2.58 | 3.87 |
| TRIB1 | NM_025195 | −0.38 | 6.42 | 0.84 | −5.58 | −2.94 | 3.85 |
| PTPLAD1 | NM_016395 | −0.32 | 15.33 | 4.73 | −10.60 | −1.70 | 3.81 |
| KIAAD174 | NM_014761 | −0.54 | 20.94 | 9.05 | −11.90 | −1.21 | 3.77 |
| HMGN1 | NM_004965 | −0.24 | 33.75 | 20.95 | −12.80 | −0.69 | 3.74 |
| BMP6 | NM_001716 | −0.26 | 22.51 | 10.75 | −11.76 | −1.07 | 3.71 |
| DHX36 | NM_020865 | −0.64 | 10.76 | 2.52 | −8.23 | −2.09 | 3.69 |
| TPM3 | NM_001043352 | −0.57 | 24.53 | 12.71 | −11.82 | −0.95 | 3.69 |
| BAG3 | NM_004281 | −1.28 | 7.05 | 1.18 | −5.87 | −2.58 | 3.63 |
| COIL | NM_004645 | −1.05 | 6.88 | 1.15 | −5.73 | −2.58 | 3.60 |
| WSB1 | NM_015626 | −0.94 | 22.86 | 11.79 | −11.07 | −0.95 | 3.60 |
| DENR | NM_003677 | −0.85 | 19.45 | 8.93 | −10.53 | −1.12 | 3.58 |
| TBC1D1 | NM_015173 | −0.58 | 10.47 | 2.67 | −7.80 | −1.97 | 3.56 |
| NAPIL1 | NM_139207 | −0.52 | 23.85 | 12.96 | −10.89 | −0.88 | 3.56 |
| PAPSS2 | NM_001015880 | −0.94 | 20.80 | 10.23 | −10.58 | −1.02 | 3.55 |
| SDC1 | NM_002997 | −0.48 | 18.60 | 8.53 | −10.07 | −1.12 | 3.52 |
| PURA | NM_005859 | −0.22 | 14.18 | 5.16 | −9.02 | −1.46 | 3.49 |
| MPPE1 | NM_023075 | −0.80 | 6.13 | 1.03 | −5.10 | −2.58 | 3.49 |
| AP3S1 | NM_001284 | −0.31 | 22.10 | 11.77 | −10.32 | −0.91 | 3.49 |
| DCTN2 | NM_006400 | −1.31 | 22.62 | 12.38 | −10.24 | −0.87 | 3.47 |
| SEC62 | NM_003262 | −0.46 | 16.23 | 6.96 | −9.27 | −1.22 | 3.44 |
| SFRS13A | NM_006625 | −0.29 | 17.03 | 7.68 | −9.35 | −1.15 | 3.42 |
| DCAF12 | NM_015397 | −0.59 | 9.17 | 2.48 | −6.69 | −1.89 | 3.33 |
| GM2A | NM_000405 | −0.37 | 9.13 | 2.47 | −6.66 | −1.89 | 3.32 |
| UBE2B | NM_003337 | −0.41 | 10.83 | 3.46 | −7.36 | −1.64 | 3.32 |
| FAM24A | NM_001029888 | −0.23 | 13.03 | 5.09 | −7.94 | −1.36 | 3.28 |
| PSMA5 | NM_002790 | −1.18 | 8.80 | 2.38 | −6.42 | −1.89 | 3.28 |
| DEPDC7 | NM_001077242 | −0.23 | 7.38 | 1.73 | −5.65 | −2.09 | 3.26 |
| RNF152 | NM_173557 | −1.23 | 7.17 | 1.68 | −5.49 | −2.09 | 3.23 |
| RHBDL2 | NM_017821 | −1.28 | 7.05 | 1.65 | −5.39 | −2.09 | 3.21 |
| ANP32B | NM_006401 | −1.34 | 17.62 | 9.39 | −8.23 | −0.91 | 3.17 |
| TROVE2 | NM_004600 | −0.92 | 11.98 | 4.68 | −7.30 | −1.36 | 3.17 |
| TBP | NM_003194 | −1.24 | 6.80 | 1.59 | −5.20 | −2.09 | 3.17 |
| RPF1 | NM_025065 | −1.25 | 11.80 | 4.61 | −7.19 | −1.36 | 3.15 |
| METTL3 | NM_019852 | −0.27 | 6.62 | 1.55 | −5.07 | −2.09 | 3.14 |
| YTHDF2 | NM_016258 | −0.27 | 9.31 | 2.96 | −6.33 | −1.64 | 3.13 |
| VPS4B | NM_004869 | −0.77 | 11.50 | 4.49 | −7.00 | −1.36 | 3.12 |
| SNX2 | NM_003100 | −1.21 | 11.27 | 4.40 | −6.86 | −1.36 | 3.09 |
| SFRS4 | NM_005626 | −1.17 | 13.30 | 6.00 | −7.30 | −1.15 | 3.09 |
| KLHL7 | NM_001031710 | −0.94 | 8.97 | 2.87 | −6.10 | −1.64 | 3.08 |
| SPRY2 | NM_005842 | −0.31 | 11.04 | 4.32 | −6.73 | −1.36 | 3.07 |
| INSIG1 | NM_198337 | −0.75 | 12.38 | 5.58 | −6.80 | −1.15 | 2.99 |
| CSTF3 | NM_001033506 | −1.28 | 10.37 | 4.05 | −6.32 | −1.36 | 2.98 |
| LIN7B | NM_022165 | −0.61 | 10.29 | 4.02 | −6.27 | −1.36 | 2.97 |
| STXBP1 | NM_001032221 | −0.24 | 10.11 | 3.95 | −6.16 | −1.36 | 2.95 |
| MFSD1 | NM_022736 | −1.12 | 9.87 | 3.86 | −6.01 | −1.36 | 2.92 |
| STXBP1 | NM_003165 | −0.22 | 9.79 | 3.83 | −5.96 | −1.36 | 2.91 |
| PRKAR2A | NM_004157 | −1.19 | 9.79 | 3.82 | −5.96 | −1.36 | 2.91 |
| NAPIL1 | NM_004537 | −0.39 | 20.71 | 13.62 | −7.09 | −0.60 | 2.89 |
| C1QBP | NM_001212 | −1.34 | 20.04 | 13.05 | −6.99 | −0.62 | 2.87 |
| SLC33A1 | NM_004733 | −0.22 | 7.48 | 2.39 | −5.09 | −1.64 | 2.87 |
| INSIG1 | NM_005542 | −0.76 | 11.18 | 5.04 | −6.14 | −1.15 | 2.86 |
| LZIC | NM_032368 | −0.42 | 12.88 | 6.47 | −6.41 | −0.99 | 2.86 |
| ANKRD17 | NM_032217 | −0.50 | 9.11 | 3.56 | −5.55 | −1.36 | 2.82 |
| FMR1 | NM_002024 | −1.08 | 12.33 | 6.19 | −6.13 | −0.99 | 2.80 |
| ATP2B1 | NM_001682 | −0.24 | 10.31 | 4.93 | −5.39 | −1.07 | 2.65 |
| ATP2B1 | NM_001001323 | −0.20 | 10.08 | 4.82 | −5.27 | −1.07 | 2.62 |

TABLE 2-continued mRNA Targets Downregulated in SEN Through miRNAs

| Gene Symbol | RefSeq ID | mirSVR Score | SR | SEN | dRPKM | FC | D |
|---|---|---|---|---|---|---|---|
| FAHD1 | NM_031208 | −0.67 | 10.76 | 5.41 | −5.35 | −0.99 | 2.62 |
| DYNC1LI2 | NM_006141 | −0.53 | 16.12 | 10.50 | −5.62 | −0.62 | 2.57 |
| RHOT1 | NM_001033568 | −0.21 | 11.74 | 6.42 | −5.32 | −0.87 | 2.56 |

Similarly, 418 out of 8367 targets predicted by mirSVR targets show downregulation at the level of protein expression based on the results of the LC-MS/MS proteomic analysis, Table 3.

TABLE 3

Protein Targets Downregulated in SEN

| Gene Symbol | RefSeq ID | mirSVR Score | SR | SEN | Diff Mean | P-value |
|---|---|---|---|---|---|---|
| mir-17-5p (MIMAT0000070) | | | | | | |
| FPR1 | NP_002020 | −0.21 | 9.26E−06 | 2.59E−06 | −6.67E−06 | 7.93E−05 |
| SH3GLB1 | NP_057093 | −0.44 | 1.92E−05 | 6.38E−06 | −1.28E−05 | 1.18E−04 |
| DNALI1 | NP_003453 | −0.20 | 3.16E−05 | 1.51E−05 | −1.65E−05 | 1.61E−04 |
| RCN2 | NP_002893 | −0.21 | 1.11E−05 | 6.78E−05 | −4.30E−06 | 3.58E−04 |
| IGFBP7 | NP_001544 | −0.23 | 1.20E−05 | 4.12E−06 | −7.89E−06 | 3.70E−04 |
| CA10 | NP_001076002 | −0.67 | 2.84E−05 | 7.68E−06 | −2.08E−05 | 4.35E−04 |
| ZEB2 | NP_055610 | −0.54 | 3.21E−05 | 8.87E−06 | −2.32E−05 | 5.33E−04 |
| KIAA1598 | NP_060800 | −1.25 | 5.37E−05 | 3.34E−05 | −2.03E−05 | 5.48E−05 |
| NUP205 | NP_055950 | −1.28 | 2.54E−05 | 1.12E−05 | −1.43E−05 | 5.66E−04 |
| MAP2 | NP_002365 | −0.33 | 8.61E−05 | 3.58E−05 | −5.03E−05 | 5.76E−04 |
| FGDS | NP_689749 | −1.18 | 1.52E−05 | 9.77E−05 | −5.40E−06 | 6.26E−04 |
| COL15A1 | NP_001846 | −0.83 | 3.44E−05 | 1.26E−05 | −2.18E−05 | 7.09E−04 |
| AHNAK | NP_001611 | −1.29 | 2.98E−03 | 2.02E−03 | −9.63E−04 | 7.28E−04 |
| U2AF1 | NP_001020374 | −0.24 | 7.00E−05 | 3.10E−05 | −3.90E−05 | 9.26E−04 |
| TCTEX1D1 | NP_689878 | −0.89 | 1.36E−05 | 5.81E−06 | −7.81E−06 | 1.10E−03 |
| ESR1 | NP_000116 | −0.40 | 3.86E−05 | 1.47E−05 | −2.39E−05 | 1.11E−03 |
| KTN1 | NP_001072989 | −0.32 | 2.25E−04 | 1.51E−04 | −7.40E−05 | 1.18E−03 |
| ANTXR1 | NP_444262 | −0.48 | 1.15E−05 | 5.19E−06 | −6.26E−06 | 1.19E−03 |
| TAOK2 | NP_057235 | −1.12 | 1.14E−04 | 7.57E−05 | −3.85E−05 | 1.25E−03 |
| VASP | NP_003361 | −0.22 | 1.75E−05 | 8.17E−06 | −9.37E−06 | 1.26E−03 |
| ATXN2 | NP_002964 | −1.08 | 1.17E−05 | 5.04E−06 | −6.65E−06 | 1.31E−03 |
| SIN3A | NP_001138829 | −0.54 | 1.10E−04 | 8.09E−05 | −2.93E−05 | 1.35E−03 |
| CHD2 | NP_001262 | −0.78 | 4.19E−05 | 1.49E−05 | −2.70E−05 | 1.49E−03 |
| RIT1 | NP_008843 | −0.50 | 1.67E−05 | 7.30E−06 | −9.41E−06 | 1.52E−03 |
| RB1 | NP_000312 | −0.72 | 3.99E−04 | 2.18E−04 | −1.81E−04 | 1.56E−03 |
| HN1 | NP_057269 | −1.29 | 1.86E−05 | 9.90E−06 | −8.73E−06 | 1.64E−03 |
| SUV39H2 | NP_001180353 | −0.48 | 4.11E−04 | 2.37E−04 | −1.74E−04 | 1.80E−03 |
| CHD4 | NP_001264 | −0.73 | 9.12E−06 | 2.78E−06 | −6.34E−06 | 1.97E−03 |
| ARID5B | NP_115575 | −0.30 | 2.46E−05 | 1.97E−05 | −4.90E−06 | 2.14E−03 |
| DYNC1U2 | NP_006132 | −1.14 | 2.42E−05 | 1.46E−05 | −9.64E−06 | 2.14E−03 |
| FTL | NP_000137 | −0.64 | 8.54E−06 | 3.95E−06 | −4.59E−06 | 2.24E−03 |
| TGM2 | NP_004604 | −1.09 | 2.95E−04 | 2.21E−04 | −7.42E−05 | 2.46E−03 |
| ETF1 | NP_004721 | −0.31 | 3.52E−05 | 2.30E−05 | −1.22E−05 | 2.47E−03 |
| CCT5 | NP_036205 | −0.44 | 3.76E−05 | 2.72E−05 | −1.04E−05 | 2.60E−03 |
| NEB | NP_001157980 | −0.23 | 4.45E−04 | 2.92E−04 | −1.53E−04 | 2.63E−03 |
| ARID1B | NP_059989 | −0.40 | 2.15E−04 | 1.20E−04 | −9.52E−05 | 2.93E−03 |
| DSTYK | NP_955749 | −0.23 | 1.00E−04 | 4.89E−05 | −5.15E−05 | 3.28E−03 |
| ANKRD11 | NP_037407 | −0.23 | 4.89E−05 | 3.12E−05 | −1.78E−05 | 3.56E−03 |
| DDX43 | NP_061135 | −0.39 | 5.40E−05 | 3.45E−05 | −1.95E−05 | 3.62E−03 |
| TRIM22 | NP_006065 | −0.99 | 8.68E−06 | 3.86E−06 | −4.82E−06 | 3.69E−03 |
| CHD9 | NP_079410 | −1.00 | 4.29E−04 | 9.94E−05 | −3.30E−04 | 3.92E−03 |
| PDE8A | NP_002596 | −0.24 | 8.89E−05 | 6.25E−05 | −2.64E−05 | 4.05E−03 |
| RBBP6 | NP_008841 | −0.46 | 2.61E−05 | 1.61E−05 | −1.00E−05 | 4.07E−03 |
| GPD2 | NP_001076581 | −0.29 | 7.59E−05 | 2.22E−05 | −5.37E−05 | 4.20E−03 |
| ZHX2 | NP_055758 | −0.75 | 5.23E−05 | 3.02E−05 | −2.21E−05 | 4.43E−03 |
| CTSA | NP_001121167 | −0.94 | 4.21E−05 | 3.13E−05 | −1.08E−05 | 4.60E−03 |
| CCDC88A | NP_001129069 | −0.83 | 9.08E−05 | 6.46E−05 | −2.62E−05 | 4.77E−03 |
| TIAM1 | NP_003244 | −1.25 | 6.62E−05 | 3.46E−05 | −3.16E−05 | 4.82E−03 |
| TOPORS | NP_005793 | −1.08 | 2.14E−04 | 1.49E−04 | −6.42E−04 | 4.91E−03 |
| ACCS | NP_115981 | −0.47 | 1.63E−05 | 9.45E−06 | −6.80E−06 | 4.91E−03 |
| NPM1 | NP_002511 | −1.06 | 5.48E−05 | 2.47E−05 | −3.01E−05 | 5.35E−03 |
| JAK3 | NP_000206 | −0.65 | 2.73E−05 | 1.11E−05 | −1.62E−05 | 5.41E−03 |
| MSR1 | NP_619729 | −1.11 | 3.63E−05 | 2.64E−05 | −9.85E−06 | 5.53E−03 |
| RPS6KA5 | NP_004746 | −1.31 | 5.24E−05 | 1.51E−05 | −3.73E−05 | 6.19E−03 |
| CIR1 | NP_004873 | −0.22 | 2.56E−05 | 9.07E−06 | −1.65E−05 | 6.52E−03 |
| HNRNPC | NP_112604 | −0.97 | 1.38E−04 | 6.56E−05 | −7.23E−05 | 6.56E−03 |

TABLE 3-continued

Protein Targets Downregulated in SEN

| Gene Symbol | RefSeq ID | mirSVR Score | SR | SEN | Diff Mean | P-value |
|---|---|---|---|---|---|---|
| HSPA8 | NP_006588 | −1.28 | 7.15E−04 | 5.35E−04 | −1.79E−04 | 7.09E−03 |
| SEPT2 | NP_004395 | −1.02 | 1.94E−04 | 1.50E−04 | −4.31E−05 | 7.52E−03 |
| FLG2 | NP_001014364 | −0.33 | 1.98E−05 | 1.42E−05 | −5.58E−06 | 7.83E−03 |
| COQ2 | NP_056512 | −0.62 | 6.27E−05 | 4.40E−05 | −1.86E−05 | 8.19E−03 |
| PAFAH1B2 | NP_002563 | −0.94 | 2.13E−05 | 1.48E−05 | −6.49E−06 | 8.73E−03 |
| NKTR | NP_005376 | −0.31 | 1.04E−04 | 7.38E−05 | −3.07E−05 | 8.45E−03 |
| PLEKHO2 | NP_001181988 | −0.53 | 4.92E−05 | 3.09E−05 | −1.83E−05 | 8.52E−03 |
| SEC24D | NP_055637 | −0.62 | 3.76E−05 | 2.56E−05 | −1.21E−05 | 8.52E−03 |
| LMAN1 | NP_005561 | −0.37 | 2.14E−04 | 1.42E−04 | −7.19E−05 | 9.04E−03 |
| ITSN1 | NP_001001132 | −0.41 | 1.95E−05 | 7.95E−06 | −1.15E−05 | 9.45E−03 |
| ZNF362 | NP_689706 | −0.84 | 2.62E−05 | 8.99E−06 | −1.73E−05 | 9.47E−03 |
| GKAP1 | NP_001129425 | −0.70 | 2.58E−05 | 1.20E−05 | −1.38E−05 | 9.93E−03 |
| RBL1 | NP_899662 | −0.77 | 2.40E−05 | 1.08E−05 | −1.32E−05 | 9.96E−03 |
| MAGI3 | NP_001136254 | −1.21 | 6.99E−05 | 4.91E−05 | −2.08E−05 | 1.00E−02 |
| RAB5B | NP_002859 | −0.98 | 4.41E−04 | 3.03E−04 | −1.38E−04 | 1.03E−02 |
| PDIK1L | NP_690048 | −0.92 | 1.71E−05 | 6.95E−06 | −1.02E−05 | 1.08E−02 |
| CALD1 | NP_149129 | −1.32 | 4.01E−04 | 2.30E−04 | −1.71E−04 | 1.13E−02 |
| IKBIP | NP_710154 | −0.85 | 1.08E−04 | 6.84E−05 | −3.96E−05 | 1.15E−02 |
| H2AFV | NP_619541 | −0.31 | 7.13E−06 | 3.77E−06 | −3.36E−06 | 1.17E−02 |
| TMMCC1 | NP_001017395 | −0.47 | 9.96E−05 | 1.66E−05 | −8.31E−05 | 1.24E−02 |
| SORL1 | NP_003096 | −0.81 | 3.49E−05 | 2.19E−05 | −1.29E−85 | 1.35E−02 |
| KIAA1109 | NP_056127 | −0.21 | 2.99E−05 | 2.46E−04 | −5.31E−05 | 1.40E−02 |
| KCNJ8 | NP_004973 | −0.85 | 1.61E−05 | 8.29E−06 | −7.83E−06 | 1.46E−02 |
| VASH2 | NP_001129947 | −0.47 | 1.92E−04 | 9.82E−05 | −9.34E−05 | 1.51E−02 |
| IQCE | NP_689771 | −0.20 | 8.70E−05 | 4.53E−05 | −4.18E−05 | 1.53E−02 |
| LATS2 | NP_055387 | −0.21 | 1.61E−04 | 1.04E−04 | −5.69E−05 | 1.57E−02 |
| IFRD1 | NP_001541 | −0.91 | 1.05E−04 | 8.19E−05 | −2.34E−05 | 1.57E−02 |
| TRPS1 | NP_054831 | −0.25 | 6.73E−05 | 5.49E−05 | −1.24E−05 | 1.60E−02 |
| NEFH | NP_066554 | −0.21 | 2.58E−05 | 1.94E−05 | −6.45E−06 | 1.65E−02 |
| ACSM5 | NP_060358 | −0.37 | 8.77E−05 | 5.29E−05 | −3.47E−05 | 1.68E−02 |
| BDH1 | NP_976059 | −0.50 | 3.36E−05 | 2.66E−05 | −6.98E−06 | 1.74E−02 |
| MTHFD1 | NP_005947 | −0.98 | 5.37E−05 | 4.33E−05 | −1.03E−05 | 1.76E−02 |
| CCDC150 | NP_001074008 | −0.27 | 5.16E−05 | 4.72E−05 | −4.38E−06 | 1.77E−02 |
| TACC2 | NP_008928 | −0.91 | 2.17E−05 | 1.54E−05 | −6.30E−06 | 1.82E−02 |
| SULF1 | NP_055985 | −0.65 | 1.11E−05 | 6.48E−06 | −4.57E−06 | 1.85E−02 |
| SMARCA5 | NP_003592 | −0.32 | 2.66E−04 | 1.80E−04 | −8.64E−05 | 1.89E−02 |
| ERG | NP_001129626 | −0.79 | 2.57E−05 | 1.33E−05 | −1.24E−05 | 1.92E−02 |
| EPB41L4B | NP_060694 | −0.70 | 2.20E−05 | 1.54E−05 | −6.58E−06 | 1.94E−02 |
| MAP3K12 | NP_006292 | −0.63 | 1.80E−05 | 1.04E−05 | −7.59E−06 | 1.97E−02 |
| ANKRD42 | NP_872409 | −0.44 | 3.12E−05 | 2.07E−05 | −1.05E−05 | 2.04E−02 |
| SYNC | NP_001155180 | −0.44 | 2.68E−04 | 1.83E−04 | −8.50E−05 | 2.05E−02 |
| SYNE2 | NP_878918 | −0.51 | 1.38E−04 | 1.02E−04 | −3.66E−05 | 2.08E−02 |
| PLIN1 | NP_001138783 | −0.51 | 5.44E−06 | 3.29E−06 | −2.16E−06 | 2.14E−02 |
| UBE3C | NP_055486 | −1.29 | 2.87E−05 | 2.02E−05 | −8.44E−06 | 2.15E−02 |
| PXDN | NP_036425 | −0.98 | 5.53E−06 | 3.89E−06 | −1.64E−06 | 2.31E−02 |
| NAP1L1 | NP_004528 | −0.25 | 1.93E−06 | 8.63E−06 | −1.07E−06 | 2.35E−02 |
| CD109 | NP_598000 | −0.44 | 3.01E−05 | 1.72E−05 | −1.28E−05 | 2.44E−02 |
| ANKS1B | NP_690001 | −1.06 | 2.50E−04 | 2.06E−04 | −4.33E−05 | 2.51E−02 |
| SEZ6 | NP_849191 | −0.47 | 4.24E−05 | 2.42E−05 | −1.81E−05 | 2.58E−02 |
| C3orf70 | NP_001020437 | −0.42 | 5.92E−05 | 1.97E−05 | −3.95E−05 | 2.64E−02 |
| WAC | NP_567823 | −0.92 | 1.16E−03 | 7.24E−04 | −4.41E−04 | 2.65E−02 |
| CYP2U1 | NP_898898 | −0.58 | 3.03E−05 | 2.67E−05 | −3.66E−06 | 2.78E−02 |
| HNRNPA1 | NP_002127 | −0.61 | 6.01E−05 | 4.06E−05 | −1.94E−05 | 2.80E−02 |
| MYO5B | NP_001073936 | −0.79 | 4.18E−04 | 1.79E−04 | −2.38E−04 | 2.82E−02 |
| DPP8 | NP_569118 | −0.38 | 5.25E−05 | 2.21E−05 | −3.04E−05 | 2.83E−02 |
| NECAB3 | NP_112509 | −0.21 | 5.21E−06 | 4.05E−06 | −1.16E−06 | 2.96E−02 |
| GOLGB1 | NP_004478 | −0.34 | 1.10E−05 | 5.72E−06 | −5.31E−06 | 2.96E−02 |
| AP4E1 | NP_031373 | −0.99 | 1.63E−05 | 9.88E−06 | −6.44E−06 | 2.97E−02 |
| KAT2B | NP_003875 | −1.10 | 4.13E−04 | 3.74E−04 | −3.89E−05 | 3.12E−02 |
| DDX5 | NP_004387 | −0.89 | 3.92E−05 | 2.32E−05 | −1.60E−05 | 3.15E−02 |
| PDIA5 | NP_006801 | −0.40 | 3.02E−05 | 1.97E−05 | −1.06E−05 | 3.28E−02 |
| SETDB2 | NP_001153780 | −0.30 | 9.39E−05 | 6.74E−05 | −2.64E−05 | 3.37E−02 |
| CLUL1 | NP_055225 | −0.44 | 1.31E−05 | 9.54E−06 | −3.52E−06 | 3.38E−02 |
| KIF5C | NP_004513 | −0.65 | 3.74E−05 | 2.77E−05 | −9.65E−06 | 3.40E−02 |
| DOCK5 | NP_079216 | −0.37 | 1.15E−05 | 6.57E−06 | −4.96E−06 | 3.42E−02 |
| ZMYM1 | NP_079048 | −0.70 | 9.78E−05 | 5.86E−05 | −3.92E−05 | 3.44E−02 |
| SNRPD3 | NP_004166 | −0.32 | 5.81E−05 | 3.88E−05 | −1.93E−05 | 3.45E−02 |
| CPNE1 | NP_690904 | −0.86 | 2.21E−05 | 1.71E−05 | −4.99E−06 | 3.47E−02 |
| KIF23 | NP_004847 | −1.22 | 3.96E−06 | 1.79E−06 | −2.17E−06 | 3.52E−02 |
| ZNF462 | NP_067047 | −0.68 | 2.38E−04 | 1.93E−04 | −4.46E−05 | 3.55E−02 |
| TAGAP | NP_473455 | −0.94 | 4.99E−05 | 3.21E−05 | −1.78E−05 | 3.69E−02 |
| BCL6 | NP_001124317 | −0.32 | 2.67E−05 | 2.01E−05 | −6.50E−06 | 3.80E−02 |
| ZEB1 | NP_001121600 | −0.32 | 7.96E−06 | 5.67E−06 | −2.29E−06 | 3.82E−02 |
| RBM20 | NP_001127835 | −0.82 | 2.52E−05 | 1.78E−05 | −7.44E−06 | 4.00E−02 |
| AHCTF1 | NP_056261 | −1.06 | 1.25E−04 | 1.01E−04 | −2.43E−05 | 4.08E−02 |
| LASP1 | NP_006139 | −0.36 | 5.47E−05 | 4.39E−05 | −1.09E−05 | 4.14E−02 |

TABLE 3-continued

| Gene Symbol | RefSeq ID | mirSVR Score | SR | SEN | Diff Mean | P-value |
|---|---|---|---|---|---|---|
| | Protein Targets Downregulated in SEN |
| TLR8 | NP_619542 | −0.72 | 8.64E−06 | 4.37E−06 | −4.27E−06 | 4.20E−02 |
| KLHL2 | NP_001154993 | −1.08 | 4.48E−05 | 1.86E−05 | −2.62E−05 | 4.33E−02 |
| CAB39L | NP_112187 | −0.44 | 1.99E−05 | 1.25E−05 | −7.32E−06 | 4.40E−02 |
| RALYL | NP_001093861 | −1.20 | 3.22E−05 | 1.78E−05 | −1.45E−05 | 4.43E−02 |
| PIP4K2C | NP_001139731 | −0.52 | 4.63E−05 | 3.60E−05 | −1.03E−05 | 4.54E−02 |
| SKI | NP_003027 | −0.59 | 1.92E−05 | 1.43E−05 | −4.92E−06 | 4.56E−02 |
| ZC3H11A | NP_055642 | −0.23 | 1.57E−04 | 8.50E−05 | −7.22E−05 | 4.59E−02 |
| DPY19L1 | NP_056098 | −0.23 | 3.63E−05 | 2.16E−05 | −1.47E−05 | 4.62E−02 |
| PCDH15 | NP_001136239 | −0.77 | 1.09E−05 | 7.87E−06 | −3.00E−06 | 4.72E−02 |
| PRDM6 | NP_001129711 | −1.22 | 1.93E−04 | 1.51E−04 | −4.26E−05 | 4.72E−02 |
| FAF2 | NP_055428 | −0.46 | 9.62E−06 | 8.20E−06 | −1.42E−06 | 4.90E−02 |
| TMEM87A | NP_056312 | −0.47 | 2.92E−05 | 2.12E−05 | −8.01E−06 | 4.95E−02 |
| | mir-18a-5p (MIMAT0000072) |
| CTNNA1 | NP_001894 | −0.52 | 8.46E−05 | 6.23E−05 | −2.23E−05 | 1.01E−05 |
| ANXA5 | NP_001145 | −0.36 | 7.40E−04 | 3.08E−04 | −4.32E−04 | 4.28E−05 |
| PCSK6 | NP_612193 | −0.24 | 3.60E−05 | 1.05E−05 | −2.55E−05 | 6.86E−05 |
| EPDR1 | NP_060019 | −0.26 | 2.78E−05 | 1.43E−05 | −1.35E−05 | 9.83E−05 |
| RNASE9 | NP_001103831 | −1.12 | 1.94E−05 | 7.13E−06 | −1.22E−05 | 1.41E−04 |
| MATR3 | NP_061322 | −1.21 | 4.91E−05 | 2.33E−05 | −2.57E−05 | 1.49E−04 |
| ANXA7 | NP_001147 | −0.72 | 3.71E−05 | 7.51E−06 | −2.96E−05 | 1.93E−04 |
| VCP | NP_009057 | −0.67 | 1.82E−04 | 1.41E−04 | −4.14E−05 | 2.31E−04 |
| LRBA | NP_006717 | −0.74 | 5.36E−05 | 3.31E−05 | −2.05E−05 | 5.55E−04 |
| HNRNPR | NP_005817 | −0.32 | 9.09E−05 | 5.69E−05 | −3.40E−05 | 8.82E−04 |
| ALS2CR11 | NP_001161693 | −0.39 | 2.70E−05 | 1.68E−05 | −1.02E−05 | 9.11E−04 |
| NRP1 | NP_003864 | −0.30 | 5.15E−05 | 2.84E−05 | −2.31E−05 | 9.36E−04 |
| BCAR3 | NP_003558 | −1.25 | 5.82E−05 | 4.24E−05 | −1.57E−05 | 1.02E−03 |
| TLL2 | NP_036597 | −0.64 | 1.37E−05 | 8.27E−06 | −5.39E−06 | 1.09E−03 |
| TCTEX1D1 | NP_689878 | −1.06 | 1.36E−05 | 5.81E−06 | −7.81E−06 | 1.10E−03 |
| ESR1 | NP_000116 | −0.70 | 3.86E−05 | 1.47E−05 | −2.39E−05 | 1.11E−03 |
| UBA6 | NP_060697 | −0.59 | 2.59E−05 | 1.32E−05 | −1.27E−05 | 1.24E−03 |
| TAOK2 | NP_057235 | −0.40 | 1.14E−04 | 7.57E−05 | −3.85E−05 | 1.25E−03 |
| COL8A2 | NP_005193 | −0.21 | 5.78E−05 | 3.13E−05 | −2.65E−05 | 1.28E−03 |
| EXOSC10 | NP_001001998 | −1.12 | 5.72E−05 | 4.32E−05 | −1.40E−05 | 1.42E−03 |
| CHD2 | NP_001262 | −0.67 | 4.19E−05 | 1.49E−05 | −2.70E−05 | 1.49E−03 |
| RIT1 | NP_008843 | −0.89 | 1.67E−05 | 7.30E−06 | −9.41E−06 | 1.52E−03 |
| ALB | NP_000468 | −0.57 | 1.15E−03 | 7.41E−04 | −4.08E−04 | 2.18E−03 |
| RC3H2 | NP_001094058 | −0.45 | 2.38E−04 | 9.35E−05 | −1.44E−04 | 2.44E−03 |
| DDX3Y | NP_001116137 | −0.25 | 1.47E−05 | 5.02E−06 | −9.64E−06 | 2.54E−03 |
| CCT5 | NP_036205 | −0.68 | 3.76E−05 | 2.72E−05 | −1.04E−05 | 2.60E−03 |
| RUVBL1 | NP_003698 | −1.13 | 1.80E−04 | 1.49E−04 | −3.07E−05 | 2.68E−03 |
| CCDC8 | NP_114429 | −0.71 | 3.31E−05 | 2.15E−05 | −1.16E−05 | 2.85E−03 |
| ABCC3 | NP_003777 | −0.48 | 1.84E−05 | 6.58E−06 | −1.19E−05 | 2.98E−03 |
| TARDBP | NP_031401 | −0.35 | 2.35E−05 | 1.80E−05 | −5.47E−06 | 3.25E−03 |
| ACACB | NP_001084 | −0.31 | 4.19E−05 | 3.38E−05 | −8.10E−06 | 3.30E−03 |
| DDX43 | NP_061135 | −0.23 | 5.40E−05 | 3.45E−05 | −1.95E−05 | 3.62E−03 |
| HNRNPUL1 | NP_008971 | −0.46 | 3.21E−05 | 1.89E−05 | −1.32E−05 | 3.66E−03 |
| ACACA | NP_942131 | −0.47 | 2.59E−05 | 1.28E−05 | −1.31E−05 | 4.07E−03 |
| RBBP6 | NP_008841 | −1.24 | 2.61E−05 | 1.61E−05 | −1.00E−05 | 4.07E−03 |
| KCTD12 | NP_612453 | −0.35 | 2.45E−05 | 1.42E−05 | −1.03E−05 | 4.32E−03 |
| ZHX2 | NP_055758 | −0.78 | 5.23E−05 | 3.02E−05 | −2.21E−05 | 4.43E−03 |
| MAFB | NP_005452 | −0.23 | 4.03E−05 | 2.23E−05 | −1.81E−05 | 4.46E−03 |
| CCDC88A | NP_001129069 | −0.34 | 9.08E−05 | 6.46E−05 | −2.62E−05 | 4.77E−03 |
| STXBP3 | NP_009200 | −0.53 | 1.47E−05 | 8.20E−06 | −6.50E−06 | 4.98E−03 |
| SEC24C | NP_940999 | −0.22 | 2.01E−04 | 1.09E−04 | −9.14E−05 | 5.67E−03 |
| RPS6KA5 | NP_004746 | −0.98 | 5.24E−05 | 1.51E−05 | −3.73E−05 | 6.19E−03 |
| ARF6 | NP_001654 | −1.10 | 2.23E−05 | 1.46E−05 | −7.69E−06 | 6.32E−03 |
| AKR1D1 | NP_005980 | −0.27 | 4.21E−05 | 2.83E−06 | −3.92E−05 | 6.39E−03 |
| SEPT2 | NP_004395 | −0.25 | 1.94E−04 | 1.50E−04 | −4.31E−05 | 7.52E−03 |
| NRL | NP_006168 | −0.21 | 6.69E−05 | 3.30E−05 | −3.39E−05 | 8.47E−03 |
| TPM3 | NP_705935 | −0.31 | 7.60E−05 | 5.26E−05 | −2.34E−05 | 8.49E−03 |
| CDK5RAP2 | NP_060719 | −0.25 | 4.41E−05 | 2.89E−05 | −1.52E−05 | 9.06E−03 |
| ITSN1 | NP_001001232 | −0.34 | 1.95E−05 | 7.95E−06 | −1.15E−05 | 9.45E−03 |
| FBXO30 | NP_115521 | −0.31 | 1.44E−05 | 6.49E−06 | −7.90E−06 | 9.70E−03 |
| SEL1L3 | NP_056002 | −0.80 | 3.16E−05 | 1.67E−05 | −1.49E−05 | 9.76E−03 |
| MAGI3 | NP_001136254 | −0.53 | 6.99E−05 | 4.91E−05 | −2.08E−05 | 1.00E−02 |
| RAB5B | NP_002859 | −0.22 | 4.41E−04 | 3.03E−04 | −1.38E−04 | 1.03E−02 |
| EFS | NP_005855 | −0.81 | 4.56E−05 | 1.85E−05 | −2.70E−05 | 1.06E−02 |
| PDIK1L | NP_690048 | −0.57 | 1.71E−05 | 6.95E−06 | −1.02E−05 | 1.08E−02 |
| PABPC4 | NP_001129125 | −0.30 | 3.90E−05 | 2.92E−05 | −9.81E−06 | 1.11E−02 |
| ANKLE2 | NP_055929 | −0.33 | 2.09E−04 | 1.24E−04 | −8.45E−05 | 1.68E−02 |
| FAM46B | NP_443175 | −0.23 | 4.06E−05 | 1.83E−05 | −2.23E−05 | 1.69E−02 |
| CX3CL1 | NP_002987 | −0.26 | 2.71E−05 | 1.67E−05 | −1.04E−05 | 1.75E−02 |
| TAF15 | NP_631961 | −0.76 | 2.13E−05 | 1.39E−05 | −7.48E−06 | 1.86E−02 |
| EPB41L4B | NP_060894 | −0.21 | 2.20E−05 | 1.54E−05 | −6.58E−06 | 1.94E−02 |
| CDC42 | NP_001782 | −1.21 | 1.34E−04 | 7.02E−05 | −6.37E−05 | 2.05E−02 |

TABLE 3-continued

Protein Targets Downregulated in SEN

| Gene Symbol | RefSeq ID | mirSVR Score | SR | SEN | Diff Mean | P-value |
|---|---|---|---|---|---|---|
| SYNC | NP_001155180 | −0.64 | 2.68E−04 | 1.83E−04 | −8.50E−05 | 2.05E−02 |
| ICT1 | NP_001536 | −0.28 | 3.12E−04 | 1.33E−04 | −1.80E−04 | 2.14E−02 |
| NAP1L1 | NP_004528 | −0.21 | 1.93E−05 | 8.63E−06 | −1.07E−05 | 2.35E−02 |
| CTH | NP_001893 | −0.39 | 1.33E−05 | 5.24E−06 | −8.09E−06 | 2.38E−02 |
| PSME4 | NP_055429 | −0.97 | 1.37E−05 | 9.08E−06 | −4.58E−06 | 2.41E−02 |
| NAA50 | NP_079422 | −0.69 | 3.77E−05 | 2.07E−05 | −1.71E−05 | 2.43E−02 |
| HNRNPA1 | NP_002127 | −0.92 | 6.01E−05 | 4.06E−05 | −1.94E−05 | 2.80E−02 |
| DOCK5 | NP_079216 | −0.74 | 1.15E−05 | 6.57E−06 | −4.96E−06 | 3.42E−02 |
| SNRPD3 | NP_004166 | −1.11 | 5.81E−05 | 3.88E−05 | −1.93E−05 | 3.45E−02 |
| GMIP | NP_057657 | −1.20 | 2.21E−05 | 1.71E−05 | −4.99E−06 | 3.47E−02 |
| CIRH1A | NP_116219 | −0.35 | 6.90E−06 | 4.55E−06 | −2.35E−06 | 3.49E−02 |
| VSIG4 | NP_009199 | −0.22 | 4.58E−05 | 1.93E−05 | −2.65E−05 | 3.67E−02 |
| TNK2 | NP_001010938 | −0.29 | 4.98E−05 | 3.22E−05 | −1.76E−05 | 3.72E−02 |
| TMCC2 | NP_055673 | −0.53 | 1.31E−05 | 7.49E−06 | −5.61E−06 | 3.84E−02 |
| PPP1R9A | NP_001159633 | −0.35 | 1.44E−05 | 5.21E−06 | −9.20E−06 | 3.87E−02 |
| MKI57 | NP_002408 | −0.29 | 2.97E−04 | 2.61E−04 | −3.63E−05 | 4.01E−02 |
| AHCTF1 | NP_056261 | −0.50 | 1.25E−04 | 1.01E−04 | −2.43E−05 | 4.08E−02 |
| PYGB | NP_002853 | −0.23 | 3.97E−06 | 1.59E−06 | −2.38E−06 | 4.22E−02 |
| KCNA1 | NP_000208 | −0.40 | 1.53E−05 | 8.08E−06 | −7.20E−06 | 4.32E−02 |
| CENP8D1 | NP_659476 | −0.45 | 1.09E−05 | 8.18E−06 | −2.70E−06 | 4.49E−02 |
| TBC1D22B | NP_060242 | −0.36 | 4.74E−05 | 2.69E−05 | −2.05E−05 | 4.53E−02 |
| MAP4K3 | NP_003609 | −0.77 | 4.64E−05 | 3.07E−05 | −1.57E−05 | 4.55E−02 |
| RIMS2 | NP_055492 | −1.15 | 9.44E−05 | 6.87E−05 | −2.58E−05 | 4.69E−02 |
| PRDM6 | NP_001129711 | −1.15 | 1.93E−04 | 1.51E−04 | −4.26E−05 | 4.72E−02 |
| MYO1H | NP_001094891 | −0.29 | 3.09E−05 | 2.39E−05 | −6.93E−06 | 4.91E−02 |
| PDCD6 | NP_037364 | −0.85 | 5.74E−06 | 3.26E−06 | −2.48E−06 | 4.97E−02 |
| mir-19a-3p (MIMAT0000073) | | | | | | |
| CTNNA1 | NP_001894 | −1.18 | 8.46E−05 | 6.23E−05 | −2.23E−05 | 1.01E−05 |
| PKD1L1 | NP_612152 | −0.99 | 1.20E−04 | 6.22E−05 | −5.76E−05 | 1.24E−05 |
| DNAJA2 | NP_005871 | −0.68 | 5.65E−06 | 3.04E−06 | −2.61E−06 | 2.88E−05 |
| SCN9A | NP_002968 | −0.48 | 9.38E−05 | 5.27E−05 | −4.11E−05 | 4.48E−05 |
| PCSK6 | NP_612193 | −0.27 | 3.60E−05 | 1.05E−05 | −2.55E−05 | 6.86E−05 |
| ABCA5 | NP_758424 | −1.12 | 2.19E−05 | 7.82E−06 | −1.40E−05 | 9.05E−05 |
| SETX | NP_055861 | −0.76 | 8.11E−05 | 3.78E−05 | −4.33E−05 | 9.14E−05 |
| JAG2 | NP_002217 | −0.51 | 3.58E−05 | 1.21E−05 | −2.37E−05 | 1.09E−04 |
| OR12D3 | NP_112221 | −0.95 | 1.58E−05 | 5.97E−06 | −9.85E−06 | 1.54E−04 |
| ANXA7 | NP_001147 | −0.61 | 3.71E−06 | 7.51E−06 | −2.96E−05 | 1.93E−04 |
| COL1A2 | NP_000080 | −1.14 | 8.86E−04 | 4.01E−04 | −4.85E−04 | 1.98E−04 |
| CRABP1 | NP_004369 | −0.39 | 1.04E−04 | 2.69E−05 | −7.68E−05 | 2.12E−04 |
| RCN2 | NP_002893 | −0.46 | 1.11E−05 | 6.78E−06 | −4.30E−06 | 3.58E−04 |
| ZEB2 | NP_055610 | −0.40 | 3.21E−05 | 8.87E−06 | −2.32E−05 | 5.33E−04 |
| KIAA1598 | NP_060800 | −0.80 | 5.37E−05 | 3.34E−05 | −2.03E−05 | 5.48E−04 |
| GRK6 | NP_002073 | −0.88 | 2.45E−05 | 1.25E−05 | −1.21E−05 | 7.26E−04 |
| DNM3 | NP_001129599 | −1.27 | 3.87E−05 | 2.77E−05 | −1.09E−05 | 7.91E−04 |
| E2F7 | NP_976328 | −1.02 | 1.93E−05 | 6.30E−06 | −1.30E−05 | 9.19E−04 |
| NRP1 | NP_003864 | −0.44 | 5.15E−05 | 2.84E−05 | −2.31E−05 | 9.36E−04 |
| BCAR3 | NP_003558 | −0.22 | 5.82E−05 | 4.24E−05 | −1.57E−05 | 1.02E−03 |
| TLL2 | NP_036597 | −0.70 | 1.37E−05 | 8.27E−06 | −5.39E−06 | 1.09E−03 |
| ESR1 | NP_000116 | −0.41 | 3.86E−05 | 1.47E−05 | −2.39E−05 | 1.11E−03 |
| ANTXR1 | NP_444262 | −0.39 | 1.15E−05 | 5.19E−06 | −6.26E−06 | 1.19E−03 |
| CS | NP_004068 | −0.76 | 1.49E−04 | 8.20E−05 | −6.70E−05 | 1.20E−03 |
| DBN1 | NP_004386 | −1.16 | 7.88E−05 | 4.24E−05 | −3.65E−05 | 1.36E−03 |
| PBX2 | NP_002577 | −0.80 | 2.00E−05 | 5.62E−06 | −1.44E−05 | 1.39E−03 |
| CHD2 | NP_001262 | −1.00 | 4.19E−05 | 1.49E−05 | −2.70E−05 | 1.49E−03 |
| GRB10 | NP_005302 | −0.74 | 1.86E−05 | 9.90E−06 | −8.73E−06 | 1.62E−03 |
| SETD7 | NP_085151 | −0.31 | 8.13E−05 | 1.71E−05 | −6.42E−05 | 1.66E−03 |
| NCBP1 | NP_002477 | −0.62 | 1.11E−03 | 5.55E−04 | −5.51E−04 | 1.75E−03 |
| IGFBP3 | NP_001013416 | −1.11 | 1.22E−03 | 5.43E−04 | −6.80E−04 | 1.81E−03 |
| PABPC1L2B | NP_001035971 | −0.35 | 6.46E−05 | 4.61E−05 | −1.85E−05 | 1.84E−03 |
| LRRC16A | NP_060110 | −0.31 | 1.95E−05 | 1.37E−05 | −5.84E−06 | 1.87E−03 |
| ANXA4 | NP_001144 | −0.93 | 1.77E−04 | 9.63E−05 | −8.11E−05 | 2.01E−03 |
| ARID5B | NP_115575 | −0.75 | 2.46E−05 | 1.97E−05 | −4.90E−06 | 2.14E−03 |
| DYNC1U2 | NP_006132 | −0.93 | 2.42E−05 | 1.46E−05 | −9.64E−06 | 2.14E−03 |
| TGM2 | NP_004604 | −0.32 | 2.95E−04 | 2.21E−04 | −7.42E−05 | 2.46E−03 |
| DDX3Y | NP_001116137 | −0.98 | 1.47E−05 | 5.02E−06 | −9.64E−06 | 2.54E−03 |
| ZC3H13 | NP_055885 | −1.05 | 8.71E−06 | 3.87E−06 | −4.84E−06 | 2.54E−03 |
| KIF1B | NP_055889 | −0.34 | 2.81E−05 | 1.50E−05 | −1.31E−05 | 2.56E−03 |
| MECOM | NP_001098547 | −1.10 | 2.44E−05 | 1.48E−05 | −9.65E−06 | 2.74E−03 |
| CCDC8 | NP_114429 | −0.24 | 3.31E−05 | 2.15E−05 | −1.16E−05 | 2.85E−03 |
| FAM178A | NP_001129595 | −0.46 | 3.30E−05 | 2.15E−05 | −1.15E−05 | 2.92E−03 |
| DAAM1 | NP_055807 | −1.22 | 2.64E−04 | 1.03E−04 | −1.61E−04 | 2.92E−03 |
| ABCC3 | NP_003777 | −1.04 | 1.84E−05 | 6.58E−06 | −1.19E−05 | 2.98E−03 |
| HIVEP2 | NP_006725 | −0.24 | 1.31E−04 | 8.79E−05 | −4.35E−05 | 3.01E−03 |
| POP1 | NP_001139333 | −0.36 | 1.01E−04 | 4.89E−05 | −5.17E−05 | 3.43E−03 |
| ANKRD11 | NP_037407 | −0.33 | 4.89E−05 | 3.12E−05 | −1.78E−05 | 3.56E−03 |

TABLE 3-continued

| Protein Targets Downregulated in SEN | | | | | | |
|---|---|---|---|---|---|---|
| Gene Symbol | RefSeq ID | mirSVR Score | SR | SEN | Diff Mean | P-value |
| CAND1 | NP_060918 | −1.11 | 2.76E−04 | 1.33E−04 | −1.43E−04 | 3.62E−03 |
| HNRNPUL1 | NP_008971 | −0.87 | 3.21E−05 | 1.89E−05 | −1.32E−05 | 3.66E−03 |
| FAM84B | NP_777571 | −0.41 | 5.26E−05 | 2.78E−05 | −2.48E−05 | 3.77E−03 |
| PLCXD2 | NP_695000 | −0.74 | 2.19E−05 | 1.50E−05 | −6.91E−06 | 3.92E−03 |
| ACACA | NP_942131 | −0.31 | 2.59E−05 | 1.28E−05 | −1.31E−05 | 4.07E−03 |
| GPD2 | NP_001076581 | −0.22 | 7.59E−05 | 2.22E−05 | −5.37E−05 | 4.20E−03 |
| RPSA | NP_001012321 | −0.69 | 2.06E−04 | 1.70E−04 | −3.60E−05 | 4.69E−03 |
| CCDC88A | NP_001129069 | −1.06 | 9.08E−05 | 6.46E−05 | −2.62E−05 | 4.77E−03 |
| CLTC | NP_004850 | −0.50 | 1.30E−03 | 1.17E−03 | −1.33E−04 | 4.87E−03 |
| HUWE1 | NP_113584 | −0.22 | 1.66E−04 | 1.18E−04 | −4.77E−05 | 5.01E−03 |
| MTF2 | NP_001157864 | −1.00 | 3.63E−05 | 2.65E−05 | −9.79E−06 | 5.41E−03 |
| PPM1K | NP_689755 | −0.41 | 1.85E−05 | 1.20E−05 | −6.48E−06 | 5.71E−03 |
| TTF2 | NP_003585 | −0.48 | 1.06E−05 | 4.96E−06 | −5.63E−06 | 5.99E−03 |
| RPS6KAS | NP_004746 | −1.02 | 5.24E−05 | 1.51E−05 | −3.73E−05 | 6.19E−03 |
| PALMD | NP_060204 | −0.20 | 9.34E−06 | 6.89E−06 | −2.45E−06 | 6.21E−03 |
| SUZ12 | NP_056170 | −1.03 | 2.65E−05 | 1.54E−05 | −1.12E−05 | 6.65E−03 |
| TRIO | NP_009049 | −0.41 | 3.60E−05 | 1.71E−05 | −1.89E−05 | 7.69E−03 |
| ZBBX | NP_078963 | −0.20 | 1.34E−05 | 5.73E−06 | −7.62E−06 | 4.95E−03 |
| CXCL12 | NP_954637 | −0.48 | 2.43E−04 | 1.60E−04 | −8.23E−05 | 7.98E−03 |
| TUB | NP_003311 | −0.68 | 1.56E−05 | 1.23E−05 | −3.24E−06 | 8.01E−03 |
| AHSG | NP_001613 | −0.97 | 7.72E−05 | 3.88E−05 | −3.84E−05 | 8.29E−03 |
| PAFAH1B2 | NP_002563 | −0.61 | 2.13E−05 | 1.48E−05 | −6.49E−06 | 8.43E−03 |
| H2AFY | NP_001035248 | −0.21 | 2.91E−04 | 1.62E−04 | −1.29E−04 | 8.71E−03 |
| KIAA1841 | NP_001123465 | −0.31 | 4.35E−05 | 2.68E−05 | −1.67E−05 | 8.98E−03 |
| CDK5RAP2 | NP_060719 | −0.29 | 4.41E−05 | 2.89E−05 | −1.52E−05 | 9.06E−03 |
| FECH | NP_000131 | −0.21 | 3.31E−05 | 1.02E−05 | −2.29E−05 | 9.07E−03 |
| ITSN1 | NP_001001132 | −1.21 | 1.95E−05 | 7.95E−06 | −1.15E−05 | 9.45E−03 |
| MED13L | NP_056150 | −0.97 | 8.49E−05 | 4.77E−05 | −3.72E−05 | 9.63E−03 |
| SEL1L3 | NP_056002 | −0.81 | 3.16E−05 | 1.67E−05 | −1.49E−05 | 9.76E−03 |
| GKAP1 | NP_001129425 | −0.30 | 2.58E−05 | 1.20E−05 | −1.38E−05 | 9.93E−03 |
| RBL1 | NP_899662 | −0.42 | 2.40E−05 | 1.08E−05 | −1.32E−05 | 9.96E−03 |
| DDX3X | NP_001180345 | −1.07 | 2.18E−05 | 1.46E−05 | −7.15E−06 | 1.03E−02 |
| ARFGAP3 | NP_055385 | −0.93 | 5.09E−05 | 3.47E−05 | −1.62E−05 | 1.03E−02 |
| RAB5B | NP_002859 | −0.47 | 4.41E−04 | 3.03E−04 | −1.38E−04 | 1.03E−02 |
| ZNF518A | NP_055618 | −1.20 | 9.54E−04 | 4.97E−04 | −4.56E−04 | 1.04E−02 |
| PDIK1L | NP_690048 | −0.81 | 1.71E−05 | 6.95E−06 | −1.02E−05 | 1.08E−02 |
| IGF2BP3 | NP_006538 | −0.93 | 1.92E−05 | 1.32E−05 | −5.99E−06 | 1.11E−02 |
| CALD1 | NP_149129 | −0.70 | 4.01E−04 | 2.30E−04 | −1.71E−04 | 1.13E−02 |
| BCL3 | NP_005169 | −0.31 | 2.10E−05 | 1.24E−05 | −8.55E−06 | 1.14E−02 |
| ATP8A1 | NP_006086 | −0.39 | 1.06E−04 | 4.58E−05 | −5.98E−05 | 1.14E−02 |
| ZBTB11 | NP_055230 | −1.11 | 1.34E−04 | 1.05E−04 | −2.90E−05 | 1.48E−02 |
| IQCE | NP_6897771 | −0.87 | 8.70E−05 | 4.53E−05 | −4.18E−05 | 1.53E−02 |
| SAP18 | NP_005861 | −0.51 | 1.81E−04 | 1.19E−04 | −6.25E−05 | 1.55E−02 |
| AKAP1 | NP_003479 | −0.23 | 2.57E−05 | 1.36E−05 | −1.20E−05 | 1.57E−02 |
| TRPS1 | NP_054831 | −0.22 | 6.73E−05 | 5.49E−05 | −1.24E−05 | 1.60E−02 |
| SPATS2L | NP_001093894 | −0.63 | 1.62E−05 | 1.11E−05 | −5.11E−06 | 1.66E−02 |
| RELN | NP_005036 | −1.28 | 4.53E−06 | 3.30E−06 | −1.23E−06 | 1.69E−02 |
| FAM46B | NP_443175 | −0.94 | 4.06E−05 | 1.83E−05 | −2.23E−05 | 1.69E−02 |
| RNF141 | NP_057506 | −1.09 | 2.10E−04 | 1.25E−04 | −8.45E−05 | 1.77E−02 |
| SULF1 | NP_055985 | −0.85 | 1.11E−05 | 6.48E−06 | −4.57E−06 | 1.85E−02 |
| ERG | NP_001129626 | −0.36 | 2.57E−05 | 1.33E−05 | −1.24E−05 | 1.92E−02 |
| MAP3K12 | NP_006292 | −0.88 | 1.80E−05 | 1.04E−05 | −7.59E−06 | 1.97E−02 |
| EIF4E3 | NP_001128123 | −0.20 | 2.58E−05 | 1.35E−05 | −1.23E−05 | 2.01E−02 |
| ANKRD42 | NP_872409 | −1.25 | 3.12E−05 | 2.07E−05 | −1.05E−05 | 2.04E−02 |
| ZNHIT6 | NP_060423 | −0.38 | 7.97E−05 | 1.50E−05 | −6.48E−05 | 2.20E−02 |
| LBR | NP_002287 | −0.90 | 1.08E−05 | 4.98E−06 | −5.83E−06 | 2.21E−02 |
| EEF1A1 | NP_001393 | −1.30 | 1.81E−03 | 1.44E−03 | −3.64E−04 | 2.21E−02 |
| RFTN1 | NP_055965 | −0.54 | 3.05E−04 | 1.25E−04 | −1.79E−04 | 2.25E−02 |
| MAP7D2 | NP_001161937 | −0.60 | 2.26E−05 | 1.26E−05 | −1.00E−05 | 2.27E−02 |
| PXDN | NP_036425 | −0.73 | 5.53E−06 | 3.89E−06 | −1.64E−06 | 2.31E−02 |
| NAPIL1 | NP_004528 | −0.50 | 1.93E−05 | 8.63E−06 | −1.07E−05 | 2.35E−02 |
| CSMD2 | NP_443128 | −0.33 | 8.05E−05 | 5.85E−05 | −2.21E−05 | 2.39E−02 |
| CMYA5 | NP_705838 | −0.69 | 4.96E−05 | 3.41E−05 | −1.55E−05 | 2.42E−02 |
| ANKS1B | NP_690001 | −0.82 | 2.50E−04 | 2.06E−04 | −4.33E−05 | 2.51E−02 |
| C3orf70 | NP_001020437 | −0.91 | 5.92E−05 | 1.97E−05 | −3.95E−05 | 2.64E−02 |
| WAC | NP_567823 | −0.90 | 1.16E−03 | 7.24E−04 | −4.41E−04 | 2.65E−02 |
| ATP6V0A1 | NP_001123493 | −0.93 | 5.56E−05 | 3.58E−05 | −1.98E−05 | 2.69E−02 |
| DPM1 | NP_003850 | −0.35 | 9.42E−05 | 4.33E−05 | −5.09E−05 | 2.72E−02 |
| SNX18 | NP_001138899 | −0.23 | 1.32E−05 | 9.50E−06 | −3.69E−06 | 2.74E−02 |
| CYP2U1 | NP_898898 | −1.06 | 3.03E−05 | 2.67E−05 | −3.66E−06 | 2.78E−02 |
| HNRNPA1 | NP_002127 | −1.11 | 6.01E−05 | 4.06E−05 | −1.94E−05 | 2.80E−02 |
| MYO5B | NP_001073936 | −0.64 | 4.18E−04 | 1.79E−04 | −2.38E−04 | 2.82E−02 |
| AFTPH | NP_060127 | −1.31 | 2.39E−05 | 8.29E−06 | −1.56E−05 | 2.85E−02 |
| NECAB3 | NP_112509 | −0.71 | 5.21E−06 | 4.05E−06 | −1.16E−06 | 2.96E−02 |
| AP4E1 | NP_031373 | −0.28 | 1.63E−05 | 9.88E−06 | −6.44E−06 | 2.97E−02 |
| INSM2 | NP_115983 | −1.00 | 7.83E−05 | 5.52E−05 | −2.31E−05 | 3.04E−02 |

TABLE 3-continued

Protein Targets Downregulated in SEN

| Gene Symbol | RefSeq ID | mirSVR Score | SR | SEN | Diff Mean | P-value |
|---|---|---|---|---|---|---|
| CASP1 | NP_150637 | −1.22 | 9.13E−05 | 8.01E−05 | −1.12E−05 | 3.09E−02 |
| PDE4A | NP_006193 | −0.44 | 3.28E−05 | 1.91E−05 | −1.37E−05 | 3.10E−02 |
| VANGL2 | NP_065068 | −0.28 | 2.13E−05 | 1.59E−05 | −5.36E−06 | 3.10E−02 |
| ARHGAP11A | NP_055598 | −1.19 | 3.57E−05 | 2.67E−05 | −9.02E−06 | 3.11E−02 |
| CGNL1 | NP_116255 | −0.72 | 2.45E−05 | 2.08E−05 | −3.77E−06 | 3.15E−02 |
| CLUL1 | NP_055225 | −1.19 | 1.31E−05 | 9.54E−06 | −3.52E−06 | 3.38E−02 |
| KIF5C | NP_004513 | −0.68 | 3.74E−05 | 2.77E−05 | −9.65E−06 | 3.40E−02 |
| PPP1R12A | NP_001137357 | −1.09 | 1.25E−04 | 8.27E−05 | −4.26E−05 | 3.42E−02 |
| DOCK5 | NP_079216 | −0.80 | 1.15E−05 | 6.57E−06 | −4.96E−06 | 3.42E−02 |
| SNRPD3 | NP_004166 | −0.50 | 5.81E−05 | 3.88E−05 | −1.93E−05 | 3.45E−02 |
| PPP1R9A | NP_001159633 | −0.23 | 1.44E−05 | 5.21E−06 | −9.20E−06 | 3.87E−02 |
| RBM20 | NP_001127835 | −0.48 | 2.52E−05 | 1.78E−05 | −7.44E−06 | 4.00E−02 |
| AHCTF1 | NP_056261 | −1.10 | 1.25E−04 | 1.01E−04 | −2.43E−05 | 4.08E−02 |
| PYGB | NP_002853 | −0.31 | 3.97E−06 | 1.59E−06 | −2.38E−06 | 4.22E−02 |
| CAB39L | NP_112187 | −0.44 | 1.99E−05 | 1.25E−05 | −7.32E−06 | 4.40E−02 |
| TBC1D22B | NP_060242 | −0.36 | 4.74E−05 | 2.69E−05 | −2.05E−05 | 4.53E−02 |
| MAP4K2 | NP_003609 | −1.22 | 4.64E−05 | 3.07E−05 | −1.57E−05 | 4.55E−02 |
| ZC3H11A | NP_055642 | −0.87 | 1.57E−04 | 8.50E−05 | −7.22E−05 | 4.59E−02 |
| FAM193A | NP_003695 | −0.40 | 9.01E−05 | 5.01E−05 | −3.99E−05 | 4.70E−02 |
| POSTN | NP_006466 | −0.71 | 2.83E−04 | 2.17E−04 | −6.56E−05 | 4.71E−02 |
| PCDH15 | NP_001136239 | −0.87 | 1.09E−05 | 7.87E−06 | −3.00E−06 | 4.72E−02 |
| CEP350 | NP_055625 | −1.15 | 7.84E−05 | 6.00E−05 | −1.84E−05 | 4.94E−02 |
| PDCD6 | NP_037364 | −0.49 | 5.74E−06 | 3.26E−06 | −2.48E−06 | 4.97E−02 |
| mir-20a-5p (MIMAT0000075) | | | | | | |
| SH3GLB1 | NP_057093 | −0.44 | 1.92E−05 | 6.38E−06 | −1.28E−05 | 1.18E−04 |
| DNAU1 | NP_003453 | −0.20 | 3.16E−05 | 1.51E−05 | −1.65E−05 | 1.61E−04 |
| LCA5L | NP_689718 | −0.32 | 5.13E−05 | 1.36E−05 | −3.77E−05 | 1.87E−04 |
| CCDC141 | NP_775919 | −0.46 | 1.84E−05 | 8.26E−06 | −1.01E−05 | 3.15E−04 |
| RCN2 | NP_002893 | −0.21 | 1.11E−05 | 6.78E−06 | −4.30E−06 | 3.58E−04 |
| IGFBP7 | NP_001544 | −0.23 | 1.20E−05 | 4.12E−06 | −7.89E−06 | 3.70E−04 |
| CA10 | NP_001076002 | −0.66 | 2.84E−05 | 7.68E−06 | −2.08E−05 | 4.35E−04 |
| ZEB2 | NP_055610 | −0.56 | 3.21E−05 | 8.87E−06 | −2.32E−05 | 5.33E−04 |
| KIAA1598 | NP_060800 | −1.25 | 5.37E−05 | 3.34E−05 | −2.03E−05 | 5.48E−04 |
| NUP205 | NP_055950 | −1.28 | 2.54E−05 | 1.12E−05 | −1.43E−05 | 5.66E−04 |
| MAP2 | NP_002365 | −0.33 | 8.61E−05 | 3.58E−05 | −5.03E−05 | 5.76E−04 |
| FGD5 | NP_689749 | −1.19 | 1.52E−05 | 9.77E−06 | −5.40E−06 | 6.26E−04 |
| COL15A1 | NP_001846 | −0.83 | 3.44E−05 | 1.26E−05 | −2.18E−05 | 7.09E−04 |
| AHNAK | NP_001611 | −1.29 | 2.98E−03 | 2.02E−03 | −9.63E−04 | 7.28E−04 |
| U2AF1 | NP_001020374 | −0.24 | 7.00E−05 | 3.10E−05 | −3.90E−05 | 9.26E−04 |
| TCTEX1D1 | NP_689878 | −0.89 | 1.36E−05 | 5.81E−06 | −7.81E−06 | 1.10E−03 |
| ESR1 | NP_000116 | −0.40 | 3.86E−05 | 1.47E−05 | −2.39E−05 | 1.11E−03 |
| KTN1 | NP_001072989 | −0.31 | 2.25E−04 | 1.51E−04 | −7.40E−05 | 1.18E−03 |
| ANTXR1 | NP_444262 | −0.48 | 1.15E−05 | 5.19E−06 | −6.26E−06 | 1.19E−03 |
| UBA6 | NP_060697 | −0.35 | 2.59E−05 | 1.32E−05 | −1.27E−05 | 1.24E−03 |
| TAOK2 | NP_057235 | −1.12 | 1.14E−04 | 7.57E−05 | −3.85E−05 | 1.25E−03 |
| VASP | NP_003361 | −0.22 | 1.75E−05 | 8.17E−06 | −9.37E−06 | 1.26E−03 |
| ATXN2 | NP_002964 | −1.08 | 1.17E−05 | 5.04E−06 | −6.65E−06 | 1.31E−03 |
| SIN3A | NP_001138829 | −0.54 | 1.10E−04 | 8.09E−05 | −2.93E−05 | 1.35E−03 |
| CHD2 | NP_001262 | −0.78 | 4.19E−05 | 1.49E−05 | −2.70E−05 | 1.49E−03 |
| RIT1 | NP_006843 | −0.50 | 1.67E−05 | 7.30E−06 | −9.41E−06 | 1.52E−03 |
| RB1 | NP_000312 | −0.72 | 3.99E−04 | 2.18E−04 | −1.81E−04 | 1.56E−03 |
| HN1 | NP_057269 | −1.29 | 1.86E−05 | 9.90E−06 | −8.73E−06 | 1.64E−03 |
| SUV39H2 | NP_001180353 | −0.48 | 4.11E−04 | 2.37E−04 | −1.74E−04 | 1.80E−03 |
| CHD4 | NP_001264 | −0.73 | 9.12E−06 | 2.78E−06 | −6.34E−06 | 1.97E−03 |
| ARID5B | NP_115575 | −0.30 | 2.46E−05 | 1.97E−05 | −4.90E−06 | 2.14E−04 |
| DYNC1LI2 | NP_006132 | −1.14 | 2.42E−05 | 1.46E−05 | −9.64E−06 | 2.14E−03 |
| FTL | NP_000137 | −0.64 | 8.54E−06 | 3.95E−06 | −4.59E−06 | 2.24E−03 |
| TGM2 | NP_004604 | −1.09 | 2.95E−04 | 2.21E−04 | −7.42E−05 | 2.46E−03 |
| ETF1 | NP_004721 | −0.30 | 3.52E−05 | 2.30E−05 | −1.22E−05 | 2.47E−03 |
| CCT5 | NP_036205 | −0.44 | 3.76E−09 | 2.72E−05 | −1.04E−05 | 2.60E−03 |
| NEB | NP_001157980 | −0.24 | 4.45E−04 | 2.92E−04 | −1.53E−04 | 2.63E−03 |
| ARID1B | NP_059989 | −0.98 | 2.15E−04 | 1.20E−04 | −9.52E−05 | 2.93E−03 |
| DSTYK | NP_955749 | −0.24 | 1.00E−04 | 4.89E−05 | −5.15E−05 | 3.28E−03 |
| ANKRD11 | NP_037407 | −0.23 | 4.89E−05 | 3.12E−05 | −1.78E−05 | 3.56E−03 |
| TRIM22 | NP_006065 | −0.99 | 8.68E−06 | 3.86E−06 | −4.82E−06 | 3.69E−03 |
| CHD9 | NP_079410 | −1.00 | 4.29E−04 | 9.94E−05 | −3.30E−04 | 3.92E−03 |
| PDE8A | NP_002596 | −0.24 | 8.89E−05 | 6.25E−05 | −2.64E−05 | 4.05E−03 |
| PBBP6 | NP_008841 | −0.43 | 2.61E−05 | 1.61E−05 | −1.00E−05 | 4.07E−03 |
| GPD2 | NP_001076581 | −0.29 | 7.59E−05 | 2.22E−05 | −5.37E−05 | 4.20E−03 |
| ZHX2 | NP_055758 | −0.76 | 5.23E−05 | 3.02E−05 | −2.21E−05 | 4.43E−03 |
| CTSA | NP_001121167 | −0.34 | 4.21E−05 | 3.13E−05 | −1.08E−05 | 4.60E−03 |
| CCDC88A | NP_001129069 | −0.83 | 9.08E−05 | 6.46E−05 | −2.62E−05 | 4.77E−03 |
| TIAM1 | NP_003244 | −1.25 | 6.62E−05 | 3.46E−05 | −3.16E−05 | 4.82E−03 |
| TOPORS | NP_005793 | −1.08 | 2.14E−04 | 1.49E−04 | −6.42E−05 | 4.91E−03 |
| ACCS | NP_115981 | −0.47 | 1.63E−05 | 9.45E−06 | −6.80E−06 | 4.91E−03 |

TABLE 3-continued

| Protein Targets Downregulated in SEN | | | | | | |
|---|---|---|---|---|---|---|
| Gene Symbol | RefSeq ID | mirSVR Score | SR | SEN | Diff Mean | P-value |
| NPM1 | NP_002511 | −1.05 | 5.48E−05 | 2.47E−05 | −3.01E−05 | 5.35E−03 |
| JAK3 | NP_000206 | −0.65 | 2.73E−05 | 1.11E−05 | −1.62E−05 | 5.41E−03 |
| MSR1 | NP_619729 | −1.11 | 3.63E−05 | 2.64E−05 | −9.85E−06 | 5.53E−03 |
| RPS6KA5 | NP_004746 | −1.29 | 5.24E−05 | 1.51E−05 | −3.73E−05 | 6.19E−03 |
| CIR1 | NP_004873 | −0.22 | 2.56E−05 | 9.07E−06 | −1.65E−05 | 6.52E−03 |
| HNRNPC | NP_112604 | −0.97 | 1.38E−04 | 6.56E−05 | −7.23E−05 | 6.56E−03 |
| NDUFA4 | NP_002480 | −1.00 | 9.62E−06 | 7.11E−06 | −2.52E−06 | 6.68E−03 |
| HSPA8 | NP_006588 | −1.28 | 7.15E−04 | 5.35E−04 | −1.79E−04 | 7.09E−03 |
| SEPT2 | NP_004395 | −1.01 | 1.94E−04 | 1.50E−04 | −4.31E−05 | 7.52E−03 |
| FLG2 | NP_001014364 | −0.33 | 1.98E−05 | 1.42E−05 | −5.58E−06 | 7.83E−03 |
| COQ2 | NP_056512 | −0.62 | 6.27E−05 | 4.40E−05 | −1.86E−05 | 8.19E−03 |
| PAFAH1B2 | NP_002563 | −0.34 | 2.13E−05 | 1.48E−05 | −6.49E−06 | 8.43E−03 |
| NKTR | NP_005376 | −0.31 | 1.04E−04 | 7.38E−05 | −3.07E−05 | 8.45E−03 |
| PLEKHO2 | NP_001181988 | −0.40 | 4.92E−05 | 3.09E−05 | −1.83E−05 | 8.52E−03 |
| SEC24D | NP_055637 | −0.63 | 3.76E−05 | 2.56E−05 | −1.21E−05 | 8.52E−03 |
| UMAN1 | NP_005561 | −0.37 | 2.14E−04 | 1.42E−04 | −7.19E−05 | 9.04E−03 |
| ZNF362 | NP_689706 | −0.84 | 2.62E−05 | 8.99E−06 | −1.73E−05 | 9.47E−03 |
| FBXO30 | NP_115521 | −0.60 | 1.44E−05 | 6.49E−06 | −7.90E−06 | 9.70E−03 |
| GKAP1 | NP_001129425 | −0.70 | 2.58E−05 | 1.20E−05 | −1.38E−05 | 9.93E−03 |
| RBL1 | NP_899662 | −0.77 | 2.40E−05 | 1.08E−05 | −1.32E−05 | 9.96E−03 |
| MAGI3 | NP_001136254 | −1.21 | 6.99E−05 | 4.91E−05 | −2.08E−05 | 1.00E−02 |
| RAB5B | NP_002859 | −0.96 | 4.41E−04 | 3.03E−04 | −1.38E−04 | 1.03E−02 |
| PDIK1L | NP_690048 | −0.93 | 1.71E−05 | 6.95E−06 | −1.02E−05 | 1.08E−02 |
| CALD1 | NP_149129 | −1.32 | 4.01E−04 | 2.30E−04 | −1.71E−04 | 1.13E−02 |
| IKBIP | NP_710154 | −0.84 | 1.08E−04 | 6.84E−05 | −3.96E−05 | 1.15E−02 |
| H2AFV | NP_619541 | −0.31 | 7.13E−06 | 3.77E−06 | −3.36E−06 | 1.17E−02 |
| TMCC1 | NP_001017395 | −0.47 | 9.96E−05 | 1.66E−05 | −8.31E−05 | 1.24E−02 |
| SORL1 | NP_003096 | −0.81 | 3.49E−05 | 2.19E−05 | −1.29E−05 | 1.35E−02 |
| KIAA1109 | NP_056127 | −0.21 | 2.99E−04 | 2.46E−04 | −5.31E−05 | 1.40E−02 |
| KCNJ8 | NP_004973 | −0.85 | 1.61E−05 | 8.29E−06 | −7.83E−06 | 1.46E−02 |
| VASH2 | NP_001129947 | −0.47 | 1.92E−04 | 9.82E−05 | −9.34E−05 | 1.51E−02 |
| IQCE | NP_689771 | −0.20 | 8.70E−05 | 4.53E−05 | −4.18E−05 | 1.53E−02 |
| LATS2 | NP_055387 | −0.21 | 1.61E−04 | 1.04E−04 | −5.65E−05 | 1.57E−02 |
| IFRD1 | NP_001541 | −0.90 | 1.05E−04 | 8.19E−05 | −2.34E−05 | 1.57E−02 |
| TRPS1 | NP_054831 | −0.25 | 6.73E−05 | 5.49E−05 | −1.24E−05 | 1.60E−02 |
| NEFH | NP_066554 | −0.22 | 2.58E−05 | 1.94E−05 | −6.45E−06 | 1.65E−02 |
| ACSM5 | NP_060358 | −0.37 | 8.77E−05 | 5.29E−05 | −3.47E−05 | 1.68E−02 |
| BDH1 | NP_976059 | −0.50 | 3.36E−05 | 2.66E−05 | −6.98E−06 | 1.74E−02 |
| MTHFD1 | NP_005947 | −0.98 | 5.37E−05 | 4.33E−05 | −1.03E−05 | 1.76E−02 |
| CCDC150 | NP_001074008 | −0.27 | 5.16E−05 | 4.72E−05 | −4.38E−06 | 1.77E−02 |
| BTF3 | NP_001032726 | −0.20 | 1.83E−05 | 1.47E−05 | −3.53E−06 | 1.80E−02 |
| TACC2 | NP_008928 | −0.91 | 2.17E−05 | 1.54E−05 | −6.30E−06 | 1.82E−02 |
| SULF1 | NP_055985 | −0.65 | 1.11E−05 | 6.48E−06 | −4.57E−06 | 1.85E−02 |
| SMARCA5 | NP_003592 | −0.32 | 2.66E−04 | 1.80E−04 | −8.64E−05 | 1.89E−02 |
| CHGA | NP_001266 | −0.63 | 3.87E−05 | 2.07E−05 | −1.80E−05 | 1.91E−02 |
| ERG | NP_001129626 | −0.79 | 2.57E−05 | 1.33E−05 | −1.24E−05 | 1.92E−02 |
| EPB41L4B | NP_060894 | −0.70 | 2.20E−05 | 1.54E−05 | −6.58E−06 | 1.94E−02 |
| MAP3K12 | NP_006292 | −0.63 | 1.80E−05 | 1.04E−05 | −7.59E−06 | 1.97E−02 |
| ANKRD42 | NP_872409 | −0.44 | 3.12E−05 | 2.07E−05 | −1.05E−05 | 2.04E−02 |
| SYNC | NP_001155180 | −0.44 | 2.68E−04 | 1.83E−04 | −8.50E−05 | 2.05E−02 |
| SYNE2 | NP_878918 | −0.51 | 1.38E−04 | 1.02E−04 | −3.66E−05 | 2.08E−02 |
| PLIN1 | NP_001138783 | −0.51 | 5.44E−06 | 3.29E−06 | −2.16E−06 | 2.14E−02 |
| UBE3C | NP_055486 | −1.29 | 2.87E−05 | 2.02E−05 | −8.44E−06 | 2.15E−02 |
| PXDN | NP_036425 | −0.98 | 5.53E−06 | 3.89E−06 | −1.64E−06 | 2.31E−02 |
| MAP7D3 | NP_078873 | −0.64 | 6.86E−06 | 5.91E−06 | −9.46E−07 | 2.35E−02 |
| NAP1L1 | NP_004528 | −0.24 | 1.93E−05 | 8.63E−06 | −1.07E−05 | 2.35E−02 |
| CD109 | NP_598000 | −0.44 | 3.01E−05 | 1.72E−05 | −1.28E−05 | 2.44E−02 |
| ANKS1B | NP_690001 | −1.06 | 2.50E−04 | 2.06E−04 | −4.33E−05 | 2.51E−02 |
| SEZ6 | NP_849191 | −0.48 | 4.24E−05 | 2.42E−05 | −1.81E−05 | 2.58E−02 |
| GAK | NP_005246 | −0.25 | 6.45E−05 | 2.78E−05 | −3.67E−05 | 2.63E−02 |
| WAC | NP_567823 | −0.92 | 1.16E−03 | 7.24E−04 | −4.41E−04 | 2.65E−02 |
| CYP2U1 | NP_898898 | −0.58 | 3.03E−05 | 2.67E−05 | −3.66E−06 | 2.78E−02 |
| MYO5B | NP_001073936 | −0.79 | 4.18E−04 | 1.79E−04 | −2.38E−04 | 2.82E−02 |
| DPP8 | NP_569118 | −0.38 | 5.25E−05 | 2.21E−05 | −3.04E−05 | 2.83E−02 |
| NECAB3 | NP_112509 | −0.21 | 5.21E−06 | 4.05E−06 | −1.16E−06 | 2.96E−02 |
| GOLGB1 | NP_004478 | −0.34 | 1.10E−05 | 5.72E−06 | −5.31E−06 | 2.96E−02 |
| AP4E1 | NP_031373 | −0.99 | 1.63E−05 | 9.88E−06 | −6.44E−06 | 2.97E−02 |
| KAT2B | NP_003875 | −1.10 | 4.13E−04 | 3.74E−04 | −3.89E−05 | 3.12E−02 |
| DDX5 | NP_004387 | −0.89 | 3.92E−05 | 2.32E−05 | −1.60E−05 | 3.15E−02 |
| PDIA5 | NP_006801 | −0.40 | 3.02E−05 | 1.97E−05 | −1.06E−05 | 3.28E−02 |
| SETDB2 | NP_001153780 | −0.30 | 9.39E−05 | 6.74E−05 | −2.64E−05 | 3.37E−02 |
| CLUL1 | NP_055225 | −0.44 | 1.31E−05 | 9.54E−06 | −3.52E−06 | 3.38E−02 |
| KIF5C | NP_004513 | −0.66 | 3.74E−05 | 2.77E−05 | −9.65E−06 | 3.40E−02 |
| PPP1R12A | NP_001137357 | −1.02 | 1.25E−04 | 8.27E−05 | −4.26E−05 | 3.42E−02 |
| DOCK5 | NP_079216 | −0.40 | 1.15E−05 | 6.57E−06 | −4.96E−06 | 3.42E−02 |
| ZMYM1 | NP_079048 | −0.70 | 9.78E−05 | 5.86E−05 | −3.92E−05 | 3.44E−02 |

TABLE 3-continued

Protein Targets Downregulated in SEN

| Gene Symbol | RefSeq ID | mirSVR Score | SR | SEN | Diff Mean | P-value |
|---|---|---|---|---|---|---|
| SNRPD3 | NP_004166 | −0.32 | 5.81E−05 | 3.88E−05 | −1.93E−05 | 3.45E−02 |
| CPNE1 | NP_690904 | −0.89 | 2.21E−05 | 1.71E−05 | −4.99E−06 | 3.47E−02 |
| KIF23 | NP_004847 | −1.22 | 3.96E−06 | 1.79E−06 | −2.17E−06 | 3.52E−02 |
| TAGAP | NP_473455 | −0.94 | 4.99E−05 | 3.21E−05 | −1.78E−05 | 3.69E−02 |
| BCL6 | NP_001124317 | −0.32 | 2.67E−05 | 2.01E−05 | −6.50E−06 | 3.80E−02 |
| ZEB1 | NP_001121600 | −0.32 | 7.96E−06 | 5.67E−06 | −2.29E−06 | 3.82E−02 |
| RBM20 | NP_001127835 | −0.82 | 2.52E−05 | 1.78E−05 | −7.44E−06 | 4.00E−02 |
| AHCTF1 | NP_056261 | −1.06 | 1.25E−04 | 1.01E−04 | −2.43E−05 | 4.08E−02 |
| LASP1 | NP_006139 | −0.36 | 5.47E−05 | 4.39E−05 | −1.09E−05 | 4.14E−02 |
| TLR8 | NP_619542 | −0.72 | 8.64E−06 | 4.37E−06 | −4.27E−06 | 4.20E−02 |
| EXOSC3 | NP_057126 | −1.08 | 3.52E−05 | 2.12E−05 | −1.39E−05 | 4.23E−02 |
| KLHL2 | NP_001154993 | −1.08 | 4.48E−05 | 1.86E−05 | −2.62E−05 | 4.33E−02 |
| CAB39L | NP_112187 | −0.44 | 1.99E−05 | 1.25E−05 | −7.32E−06 | 4.40E−02 |
| RALYL | NP_001093861 | −1.19 | 3.22E−05 | 1.78E−05 | −1.45E−05 | 4.43E−02 |
| CENPBD1 | NP_659476 | −0.42 | 1.09E−05 | 8.18E−06 | −2.70E−05 | 4.49E−02 |
| PIP4K2C | NP_001139731 | −0.52 | 4.63E−05 | 3.60E−05 | −1.03E−05 | 4.54E−02 |
| SKI | NP_003027 | −0.59 | 1.92E−05 | 1.43E−05 | −4.92E−06 | 4.56E−02 |
| ZC3H11A | NP_055642 | −0.23 | 1.57E−04 | 8.50E−05 | −7.22E−05 | 4.59E−02 |
| DPY19L1 | NP_056098 | −0.23 | 3.63E−05 | 2.16E−05 | −1.47E−05 | 4.62E−02 |
| ZNF528 | NP_115799 | −0.49 | 1.74E−05 | 9.52E−06 | −7.87E−06 | 4.67E−02 |
| PCDH15 | NP_001136239 | −0.77 | 1.09E−05 | 7.87E−06 | −3.00E−06 | 4.72E−02 |
| PRDM6 | NP_001129711 | −1.22 | 1.93E−04 | 1.51E−04 | −4.26E−05 | 4.72E−02 |
| FAF2 | NP_055428 | −0.46 | 9.62E−06 | 8.20E−06 | −1.42E−06 | 4.90E−02 |
| TMEM87A | NP_056312 | −0.21 | 2.92E−05 | 2.12E−05 | −8.01E−05 | 4.95E−02 |
| mir-100-5p (MIMAT0000098) | | | | | | |
| EPDR1 | NP_060019 | −0.37 | 2.78E−05 | 1.43E−05 | −1.35E−05 | 9.83E−05 |
| CCDC141 | NP_775919 | −0.59 | 1.84E−05 | 8.26E−06 | −1.01E−05 | 3.15E−04 |
| ST5 | NP_631896 | −0.36 | 2.01E−05 | 5.56E−06 | −1.45E−05 | 1.28E−03 |
| TARDBP | NP_031401 | −0.92 | 2.35E−05 | 1.80E−05 | −5.47E−06 | 3.25E−03 |
| HNRNPH2 | NP_062543 | −0.41 | 3.11E−05 | 1.32E−05 | −1.79E−06 | 5.38E−03 |
| PTPRN2 | NP_570857 | −0.21 | 4.39E−05 | 2.90E−05 | −1.49E−05 | 5.59E−03 |
| VNN1 | NP_004657 | −0.97 | 6.24E−06 | 3.95E−06 | −2.29E−06 | 1.35E−02 |
| SMARCA5 | NP_003592 | −1.27 | 2.66E−04 | 1.80E−04 | −8.64E−05 | 1.89E−02 |
| HOXA1 | NP_005513 | −0.84 | 2.82E−06 | 1.53E−06 | −1.30E−06 | 3.08E−02 |
| NOP56 | NP_006383 | −0.29 | 8.98E−05 | 6.46E−05 | −2.52E−05 | 3.27E−02 |
| TBC1D22B | NP_060242 | −0.51 | 4.74E−05 | 2.69E−05 | −2.05E−05 | 4.53E−02 |
| mir-125b-5p (MIMAT0000423) | | | | | | |
| PLCB2 | NP_004564 | −0.44 | 1.96E−05 | 1.38E−05 | −5.79E−06 | 1.27E−05 |
| COL1A2 | NP_000080 | −0.37 | 8.86E−04 | 4.01E−04 | −4.85E−04 | 1.98E−04 |
| ACSBG2 | NP_112186 | −0.40 | 1.96E−05 | 9.43E−06 | −1.02E−05 | 3.52E−04 |
| ZEB2 | NP_055610 | −0.59 | 3.21E−05 | 8.87E−06 | −2.32E−05 | 5.33E−04 |
| KIAA1598 | NP_060800 | −0.55 | 5.37E−05 | 3.34E−05 | −2.03E−05 | 5.48E−04 |
| CALCA | NP_001029124 | −0.52 | 3.54E−04 | 1.72E−04 | −1.81E−04 | 1.28E−03 |
| EXOSC10 | NP_001001998 | −0.65 | 5.72E−05 | 4.32E−05 | −1.40E−05 | 1.42E−03 |
| RIT1 | NP_008843 | −0.51 | 1.67E−05 | 7.30E−06 | −9.41E−05 | 1.52E−03 |
| RB1 | NP_000312 | −0.51 | 3.99E−04 | 2.18E−04 | −1.81E−04 | 1.56E−03 |
| MUC5B | NP_002449 | −0.21 | 4.56E−05 | 2.80E−05 | −1.76E−05 | 1.84E−03 |
| ZC3H13 | NP_055885 | −0.36 | 8.71E−06 | 3.87E−06 | −4.84E−06 | 2.54E−03 |
| HIVEP2 | NP_006725 | −0.38 | 1.31E−04 | 8.79E−05 | −4.35E−05 | 3.01E−03 |
| NAIF1 | NP_931045 | −0.25 | 1.89E−05 | 1.24E−05 | −6.51E−06 | 4.23E−03 |
| SLC25A35 | NP_958928 | −0.99 | 3.38E−05 | 1.70E−05 | −1.69E−05 | 4.77E−03 |
| CASC3 | NP_031385 | −0.26 | 1.08E−04 | 5.58E−05 | −5.20E−05 | 5.14E−03 |
| PLIN3 | NP_005808 | −0.32 | 1.89E−05 | 1.49E−05 | −3.94E−06 | 5.70E−03 |
| ARNTL | NP_001025444 | −0.75 | 8.34E−05 | 4.87E−05 | −3.48E−05 | 6.16E−03 |
| AKR1S1 | NP_005980 | −0.40 | 4.21E−05 | 2.83E−06 | −3.92E−05 | 6.39E−03 |
| RGAG1 | NP_065820 | −0.32 | 7.88E−06 | 5.32E−06 | −2.57E−06 | 7.03E−03 |
| TRIO | NP_009049 | −0.83 | 3.60E−05 | 1.71E−05 | −1.89E−05 | 7.69E−03 |
| KIAA1B41 | NP_001123465 | −0.62 | 4.35E−05 | 2.68E−05 | −1.67E−05 | 8.98E−03 |
| CDK5RAP2 | NP_060719 | −0.72 | 4.41E−05 | 2.89E−05 | −1.52E−05 | 9.06E−03 |
| ITSN1 | NP_001001132 | −0.26 | 1.95E−05 | 7.95E−06 | −1.15E−05 | 9.45E−03 |
| EML6 | NP_001034842 | −0.29 | 3.57E−05 | 2.41E−05 | −1.16E−05 | 1.01E−02 |
| TOMM40 | NP_006105 | −0.21 | 4.57E−05 | 2.96E−05 | −1.61E−05 | 1.13E−02 |
| IKBIP | NP_710154 | −0.38 | 1.08E−04 | 6.84E−05 | −3.96E−05 | 1.15E−02 |
| MYO15A | NP_057323 | −0.42 | 4.59E−05 | 3.44E−05 | −1.15E−05 | 1.33E−02 |
| ARHGEF2 | NP_004714 | −0.33 | 2.66E−04 | 1.75E−04 | −9.17E−05 | 1.46E−02 |
| VASH2 | NP_001129947 | −0.49 | 1.92E−05 | 9.82E−05 | −9.34E−05 | 1.51E−02 |
| TRPS1 | NP_054831 | −0.31 | 6.73E−05 | 5.49E−05 | −1.24E−05 | 1.60E−02 |
| BDH1 | NP_976059 | −0.47 | 3.36E−05 | 2.66E−05 | −6.98E−06 | 1.74E−02 |
| RNF141 | NP_057506 | −0.77 | 2.10E−04 | 1.25E−04 | −8.45E−05 | 1.77E−02 |
| HNRNPA2B1 | NP_112533 | −0.32 | 1.33E−04 | 7.21E−05 | −6.06E−05 | 1.84E−02 |
| PDZD3 | NP_079067 | −1.09 | 4.08E−05 | 7.18E−06 | −3.36E−05 | 1.93E−02 |
| MAP3K12 | NP_006292 | −0.21 | 1.80E−05 | 1.04E−05 | −7.59E−06 | 1.97E−02 |
| PNPT1 | NP_149100 | −0.90 | 1.12E−05 | 7.93E−06 | −3.30E−06 | 1.99E−02 |
| MTMR14 | NP_001070993 | −0.78 | 1.15E−05 | 0.00E+00 | −1.15E−05 | 2.00E−02 |

TABLE 3-continued

| Gene Symbol | RefSeq ID | mirSVR Score | SR | SEN | Diff Mean | P-value |
|---|---|---|---|---|---|---|
| ANKRD42 | NP_872409 | −1.11 | 3.12E−05 | 2.07E−05 | −1.05E−05 | 2.04E−02 |
| PTPRS | NP_002841 | −0.28 | 1.16E−05 | 4.98E−06 | −6.62E−06 | 2.40E−02 |
| ANPEP | NP_001141 | −0.32 | 6.21E−04 | 5.01E−04 | −1.20E−04 | 2.44E−02 |
| CYP24A1 | NP_000773 | −0.73 | 3.33E−04 | 2.35E−04 | −9.80E−05 | 2.90E−02 |
| NECAB3 | NP_112509 | −0.39 | 5.21E−06 | 4.05E−06 | −1.16E−06 | 2.96E−02 |
| GOLGB1 | NP_004478 | −0.23 | 1.10E−05 | 5.72E−06 | −5.31E−06 | 2.96E−02 |
| ENTPD1 | NP_001767 | −0.22 | 3.15E−05 | 2.39E−05 | −7.61E−06 | 3.01E−02 |
| PPCDC | NP_068595 | −0.29 | 1.78E−05 | 1.41E−05 | −3.69E−06 | 3.17E−02 |
| GMIP | NP_057657 | −0.41 | 2.21E−05 | 1.71E−05 | −4.99E−06 | 3.47E−02 |
| KIF23 | NP_004847 | −0.45 | 3.96E−06 | 1.79E−06 | −2.17E−06 | 3.52E−02 |
| RBM20 | NP_001127835 | −0.79 | 2.52E−05 | 1.78E−05 | −7.44E−06 | 4.00E−02 |
| PCDH15 | NP_001136239 | −0.38 | 1.09E−05 | 7.87E−05 | −3.00E−06 | 4.72E−02 |
| PDCD6 | NP_037364 | −0.63 | 5.74E−06 | 3.26E−06 | −2.48E−06 | 4.97E−02 |
| mir-92a-1-5p (MIMAT0004507) | | | | | | |
| YWHAH | NP_003396 | −0.24 | 6.61E−05 | 1.92E−05 | −4.68E−05 | 8.56E−06 |
| COL1A1 | NP_000079 | −0.75 | 2.23E−03 | 6.76E−04 | −1.55E−03 | 7.25E−05 |
| ABCA5 | NP_758424 | −0.39 | 2.19E−05 | 1.82E−06 | −1.40E−05 | 9.05E−05 |
| CNTN5 | NP_780775 | −0.20 | 1.04E−04 | 2.67E−05 | −7.73E−05 | 1.95E−04 |
| VIM | NP_003371 | −0.29 | 5.05E−02 | 3.74E−02 | −1.31E−02 | 2.04E−04 |
| LMO7 | NP_056667 | −0.25 | 1.74E−05 | 7.66E−06 | −9.71E−06 | 4.43E−04 |
| ANO10 | NP_060545 | −0.27 | 4.65E−05 | 2.48E−05 | −2.18E−05 | 6.53E−04 |
| ANXA2 | NP_001129487 | −0.30 | 7.03E−03 | 4.42E−03 | −2.61E−03 | 1.26E−03 |
| LRCH4 | NP_002310 | −0.50 | 4.52E−05 | 2.59E−05 | −1.93E−05 | 1.30E−03 |
| ATXN2 | NP_002964 | −0.25 | 1.17E−05 | 5.04E−06 | −6.65E−06 | 1.31E−03 |
| SIN3A | NP_001138829 | −0.39 | 1.10E−04 | 8.09E−05 | −2.93E−05 | 1.35E−03 |
| CHD2 | NP_001262 | −0.43 | 4.19E−05 | 1.49E−05 | −2.70E−05 | 1.49E−03 |
| PPEF2 | NP_006230 | −0.29 | 4.69E−05 | 2.04E−05 | −2.65E−05 | 1.78E−03 |
| CANX | NP_001737 | −0.39 | 6.95E−04 | 4.89E−04 | −2.06E−04 | 2.12E−03 |
| FTL | NP_000137 | −0.50 | 8.54E−06 | 3.95E−06 | −4.59E−06 | 2.24E−03 |
| HNRNPK | NP_112553 | −0.91 | 3.12E−04 | 1.97E−04 | −1.15E−04 | 2.68E−03 |
| MECOM | NP_001098547 | −1.28 | 2.44E−05 | 1.48E−05 | −9.65E−06 | 2.74E−03 |
| FA2H | NP_077282 | −0.25 | 1.67E−04 | 8.13E−05 | −8.53E−05 | 3.09E−03 |
| NETO1 | NP_620416 | −0.84 | 2.85E−05 | 1.99E−05 | −8.57E−06 | 3.44E−03 |
| HNRNPUL1 | NP_008971 | −0.42 | 3.21E−05 | 1.89E−05 | −1.32E−05 | 3.66E−03 |
| PLCXD2 | NP_695000 | −0.25 | 2.19E−05 | 1.50E−05 | −6.91E−06 | 3.92E−03 |
| BGN | NP_001702 | −0.22 | 8.52E−05 | 6.24E−05 | −2.28E−05 | 4.83E−03 |
| NFYC | NP_055038 | −0.23 | 1.29E−04 | 4.74E−05 | −8.18E−05 | 4.89E−03 |
| HUWE1 | NP_113584 | −0.34 | 1.66E−04 | 1.18E−04 | −4.77E−05 | 5.01E−03 |
| JAK3 | NP_000206 | −0.35 | 2.73E−05 | 1.11E−05 | −1.62E−05 | 5.41E−03 |
| RRBP1 | NP_004578 | −0.32 | 1.90E−04 | 1.31E−04 | −5.93E−05 | 5.62E−03 |
| SEC24C | NP_940999 | −0.51 | 2.01E−04 | 1.09E−04 | −9.14E−05 | 5.67E−03 |
| PPM1K | NP_689755 | −0.48 | 1.85E−05 | 1.20E−05 | −6.48E−05 | 5.71E−03 |
| HAVCR2 | NP_116171 | −0.72 | 2.08E−05 | 1.18E−05 | −9.02E−05 | 6.39E−03 |
| LMAN2 | NP_006807 | −1.18 | 4.87E−05 | 3.50E−05 | −1.36E−05 | 7.56E−03 |
| KIAA1841 | NP_001123465 | −1.04 | 4.35E−05 | 2.68E−05 | −1.67E−05 | 8.98E−03 |
| CDK5RAP2 | NP_060719 | −0.23 | 4.41E−05 | 2.89E−05 | −1.52E−05 | 9.06E−03 |
| CRKL | NP_005198 | −0.27 | 1.82E−05 | 1.50E−05 | −3.17E−06 | 9.78E−03 |
| HDAC1 | NP_004955 | −0.61 | 7.01E−04 | 5.89E−04 | −1.12E−04 | 1.02E−02 |
| CALD1 | NP_149129 | −0.24 | 4.01E−04 | 2.30E−04 | −1.71E−04 | 1.13E−02 |
| NLRC3 | NP_849172 | −0.28 | 2.54E−05 | 1.32E−05 | −1.22E−05 | 1.16E−02 |
| RPTN | NP_001116437 | −0.41 | 3.03E−05 | 1.89E−05 | −1.14E−05 | 1.57E−02 |
| TRPS1 | NP_054831 | −0.92 | 6.73E−05 | 5.49E−05 | −1.24E−05 | 1.60E−02 |
| PDZRN3 | NP_055824 | −0.38 | 1.62E−05 | 1.11E−05 | −5.11E−06 | 1.66E−02 |
| VAT1 | NP_006364 | −0.39 | 3.54E−04 | 2.80E−04 | −7.40E−05 | 1.67E−02 |
| TAF15 | NP_631961 | −0.92 | 2.13E−05 | 1.39E−05 | −7.48E−06 | 1.86E−02 |
| TJAP1 | NP_001139489 | −0.35 | 1.13E−05 | 7.93E−06 | −3.34E−06 | 1.88E−02 |
| ERG | NP_001129626 | −0.25 | 2.57E−05 | 1.33E−05 | −1.24E−05 | 1.92E−02 |
| DPYSL3 | NP_001378 | −0.70 | 4.92E−05 | 4.25E−05 | −6.66E−06 | 2.04E−02 |
| PLIN1 | NP_001138783 | −0.55 | 5.44E−06 | 3.29E−06 | −2.16E−06 | 2.14E−02 |
| ADCY4 | NP_640340 | −0.21 | 5.82E−05 | 3.42E−05 | −2.39E−05 | 2.46E−02 |
| ANKS1B | NP_690001 | −0.35 | 2.50E−04 | 2.06E−04 | −4.33E−05 | 2.51E−02 |
| PPFIA4 | NP_055868 | −0.71 | 6.09E−06 | 3.38E−06 | −2.70E−06 | 2.57E−02 |
| DNAH5 | NP_001360 | −1.06 | 1.68E−04 | 1.00E−04 | −6.79E−05 | 2.57E−02 |
| CYP2B6 | NP_000758 | −0.48 | 1.25E−04 | 1.02E−04 | −2.37E−05 | 2.64E−02 |
| PPARGC1B | NP_001166170 | −0.29 | 4.56E−04 | 2.20E−04 | −2.36E−04 | 2.76E−02 |
| FGD6 | NP_060821 | −0.29 | 2.34E−04 | 1.85E−04 | −4.90E−05 | 2.86E−02 |
| INTS4 | NP_291025 | −0.26 | 7.03E−05 | 4.90E−05 | −2.12E−05 | 2.87E−02 |
| GALM | NP_620156 | −1.00 | 4.36E−05 | 2.69E−05 | −1.67E−05 | 2.95E−02 |
| PCOLCE | NP_002584 | −0.39 | 2.64E−05 | 1.90E−05 | −7.33E−05 | 3.01E−02 |
| CPNE1 | NP_690904 | −0.34 | 2.21E−05 | 1.71E−05 | −4.99E−06 | 3.47E−02 |
| NCSTN | NP_056146 | −0.35 | 3.96E−06 | 2.91E−06 | −1.05E−06 | 3.85E−02 |
| C12orf54 | NP_689532 | −0.27 | 1.44E−05 | 5.22E−06 | −9.19E−06 | 3.87E−02 |

TABLE 3-continued

Protein Targets Downregulated in SEN

| Gene Symbol | RefSeq ID | mirSVR Score | SR | SEN | Diff Mean | P-value |
|---|---|---|---|---|---|---|
| EBPL | NP_115954 | −0.66 | 1.71E−04 | 1.13E−04 | −5.88E−05 | 4.00E−02 |
| BEST2 | NP_060152 | −0.37 | 3.37E−05 | 2.02E−05 | −1.35E−05 | 4.13E−02 |
| TBC1D22B | NP_060242 | −0.58 | 4.74E−05 | 2.69E−05 | −2.05E−05 | 4.53E−02 |
| SKI | NP_003027 | −0.27 | 1.92E−05 | 1.43E−05 | −4.92E−06 | 4.56E−02 |
| let-7a-2-3p (MIMAT0010195) | | | | | | |
| YWHAH | NP_003396 | −0.58 | 6.61E−05 | 1.92E−05 | −4.68E−05 | 8.56E−06 |
| PLCB2 | NP_004564 | −0.46 | 1.96E−05 | 1.38E−05 | −5.97E−06 | 1.27E−05 |
| DNAJA2 | NP_005871 | −0.32 | 5.65E−06 | 3.04E−06 | −2.61E−06 | 2.88E−05 |
| CASS4 | NP_065089 | −0.86 | 3.14E−05 | 2.08E−05 | −1.06E−05 | 4.54E−05 |
| PCSK6 | NP_612193 | −0.77 | 3.60E−05 | 1.05E−05 | −2.55E−05 | 6.86E−05 |
| ELF1 | NP_001138825 | −0.21 | 5.78E−05 | 1.47E−05 | −4.31E−05 | 1.24E−04 |
| COL10A1 | NP_000484 | −0.22 | 1.90E−05 | 1.02E−05 | −8.82E−06 | 1.39E−04 |
| ANXA7 | NP_001147 | −0.26 | 3.71E−05 | 7.51E−06 | −2.96E−05 | 1.93E−04 |
| ZEB2 | NP_055610 | −0.65 | 3.21E−05 | 8.87E−06 | −2.32E−05 | 5.33E−04 |
| LRBA | NP_006717 | −0.70 | 5.36E−05 | 3.31E−05 | −2.05E−05 | 5.55E−04 |
| DST | NP_056363 | −0.28 | 4.49E−05 | 2.06E−05 | −2.43E−05 | 6.40E−04 |
| AHNAK | NP_001611 | −1.14 | 2.98E−03 | 2.02E−03 | −9.63E−4 | 7.28E−04 |
| DNM3 | NP_001129599 | −0.38 | 3.87E−05 | 2.77E−05 | −1.09E−05 | 7.91E−04 |
| NAPA | NP_003818 | −0.48 | 6.33E−04 | 4.23E−04 | −2.10E−04 | 9.95E−04 |
| CDH11 | NP_001788 | −0.81 | 1.18E−05 | 5.32E−06 | −6.52E−06 | 1.05E−03 |
| TCTEX1D1 | NP_689878 | −0.64 | 1.36E−05 | 5.81E−06 | −7.81E−06 | 1.10E−03 |
| ESR1 | NP_000116 | −0.21 | 3.86E−05 | 1.47E−05 | −2.39E−05 | 1.11E−03 |
| KTN1 | NP_001072989 | −0.30 | 2.25E−04 | 1.51E−04 | −7.40E−05 | 1.18E−03 |
| ANTXR1 | NP_444262 | −0.28 | 1.15E−05 | 5.19E−06 | −6.26E−06 | 1.19E−03 |
| CS | NP_004068 | −1.16 | 1.49E−04 | 8.20E−05 | −6.70E−05 | 1.20E−03 |
| KLHL7 | NP_001165899 | −0.94 | 2.59E−05 | 1.32E−05 | −1.27E−05 | 1.24E−03 |
| UBAG | NP_060597 | −0.23 | 2.59E−05 | 1.32E−05 | −1.27E−05 | 1.24E−03 |
| THAP11 | NP_065190 | −1.34 | 5.92E−05 | 3.28E−05 | −2.63E−05 | 1.30E−03 |
| LRCH4 | NP_002310 | −0.46 | 4.52E−05 | 2.59E−05 | −1.93E−05 | 1.30E−03 |
| RB1 | NP_000312 | −1.17 | 3.99E−04 | 2.18E−04 | −1.81E−04 | 1.56E−03 |
| GRB10 | NP_005302 | −0.72 | 1.86E−05 | 9.90E−06 | −8.73E−06 | 1.62E−03 |
| HN1 | NP_057269 | −0.98 | 1.86E−05 | 9.90E−06 | −8.73E−06 | 1.64E−03 |
| NCBP1 | NP_002477 | −0.30 | 1.11E−03 | 5.55E−04 | −5.51E−04 | 1.75E−03 |
| PLEKHAS | NP_001137293 | −0.57 | 3.64E−04 | 2.05E−04 | −1.60E−04 | 1.76E−03 |
| H1F0 | NP_005309 | −0.63 | 6.34E−03 | 2.55E−03 | −3.78E−03 | 1.93E−03 |
| DYNC1U2 | NP_006132 | −0.53 | 2.42E−05 | 1.46E−05 | −9.64E−06 | 2.14E−03 |
| ZNF10 | NP_056209 | −0.59 | 3.19E−05 | 1.85E−05 | −1.34E−05 | 2.40E−03 |
| RC3H2 | NP_001094058 | −0.23 | 2.38E−04 | 9.35E−05 | −1.44E−04 | 2.44E−03 |
| GTF2IRD1 | NP_005676 | −0.77 | 2.30E−05 | 4.49E−06 | −1.85E−05 | 2.46E−03 |
| COL3A1 | NP_000081 | −0.81 | 6.74E−04 | 4.16E−04 | −2.58E−04 | 2.49E−03 |
| ZC3H13 | NP_055885 | −1.04 | 8.71E−06 | 3.87E−06 | −4.84E−06 | 2.54E−03 |
| HNRNPK | NP_112553 | −0.26 | 3.12E−04 | 1.97E−04 | −1.15E−04 | 2.68E−03 |
| MECOM | NP_001098547 | −0.34 | 2.44E−05 | 1.48E−05 | −9.65E−06 | 2.74E−03 |
| FAM178A | NP_001129595 | −0.21 | 3.30E−05 | 2.15E−05 | −1.15E−05 | 2.92E−03 |
| ARID1B | NP_059989 | −0.53 | 2.15E−04 | 1.20E−04 | −9.52E−05 | 2.93E−03 |
| HIVEP2 | NP_006725 | −0.55 | 1.31E−04 | 8.79E−05 | −4.35E−05 | 3.01E−03 |
| ANKRD11 | NP_037407 | −0.81 | 4.89E−05 | 3.12E−05 | −1.78E−05 | 3.56E−03 |
| SP140 | NP_009168 | −0.30 | 2.28E−05 | 1.50E−05 | −7.79E−06 | 3.63E−03 |
| SRP72 | NP_008878 | −0.31 | 2.90E−05 | 2.02E−05 | −8.86E−06 | 3.80E−03 |
| ARHGAP36 | NP_659404 | −0.95 | 7.17E−05 | 5.47E−05 | −1.70E−05 | 3.92E−03 |
| RBBP6 | NP_008841 | −0.33 | 2.61E−05 | 1.61E−05 | −1.00E−05 | 4.07E−03 |
| CCDC88A | NP_001129069 | −0.39 | 9.08E−05 | 6.46E−05 | −2.62E−05 | 4.77E−03 |
| PSIP1 | NP_001121689 | −0.40 | 1.86E−05 | 1.20E−05 | −6.55E−06 | 4.77E−03 |
| PKP4 | NP_003619 | −0.25 | 3.67E−04 | 2.64E−04 | −1.03E−04 | 5.07E−03 |
| HNRNPH2 | NP_062543 | −0.83 | 3.11E−05 | 1.32E−05 | −1.79E−05 | 5.38E−03 |
| METTL6 | NP_689609 | −0.38 | 3.63E−05 | 2.65E−05 | −9.81E−06 | 5.44E−03 |
| PPM1K | NP_689755 | −0.27 | 1.85E−05 | 1.20E−05 | −6.48E−06 | 5.71E−03 |
| AKAP12 | NP_005091 | −0.51 | 1.08E−04 | 7.54E−05 | −3.26E−05 | 5.86E−03 |
| STAC2 | NP_945344 | −0.23 | 1.84E−04 | 1.33E−05 | −5.12E−06 | 6.01E−03 |
| NPVF | NP_071433 | −0.78 | 2.44E−05 | 1.16E−05 | −1.28E−05 | 6.07E−03 |
| RPS6KA5 | NP_004746 | −0.40 | 5.24E−05 | 1.51E−05 | −3.73E−05 | 6.19E−03 |
| SUZ12 | NP_056170 | −0.38 | 2.65E−05 | 1.54E−05 | −1.12E−05 | 6.65E−03 |
| EIF4ENIF1 | NP_062817 | −1.14 | 7.04E−05 | 4.89E−05 | −2.15E−05 | 7.11E−03 |
| MMRN2 | NP_079032 | −0.87 | 1.06E−05 | 3.89E−06 | −6.70E−06 | 7.43E−03 |
| TRIO | NP_009049 | −0.78 | 3.60E−05 | 1.71E−05 | −1.89E−05 | 7.69E−03 |
| FLG2 | NP_001014364 | −1.24 | 1.98E−05 | 1.42E−05 | −5.58E−06 | 7.83E−03 |
| PAFAH1B2 | NP_002563 | −0.88 | 2.13E−05 | 1.48E−05 | −6.49E−06 | 8.43E−03 |
| TPM3 | NP_705935 | −0.89 | 7.60E−05 | 5.26E−05 | −2.34E−05 | 8.49E−03 |
| SEC24D | NP_055637 | −0.44 | 3.76E−05 | 2.56E−05 | −1.21E−05 | 8.52E−03 |
| DOCK8 | NP_001177387 | −0.37 | 8.39E−06 | 2.33E−06 | −6.06E−06 | 8.83E−03 |
| KIAA1841 | NP_001123465 | −1.24 | 4.35E−05 | 2.68E−05 | −1.67E−05 | 8.98E−03 |
| ITSN1 | NP_001001132 | −0.80 | 1.95E−05 | 7.95E−06 | −1.15E−05 | 9.45E−03 |
| MED13L | NP_056150 | −0.99 | 8.49E−05 | 4.77E−05 | −3.72E−05 | 9.63E−03 |
| RAB5B | NP_002859 | −0.37 | 4.41E−04 | 3.03E−04 | −1.38E−04 | 1.03E−02 |
| ZNF518A | NP_055618 | −0.93 | 9.54E−04 | 4.97E−04 | −4.56E−04 | 1.04E−02 |

TABLE 3-continued

Protein Targets Downregulated in SEN

| Gene Symbol | RefSeq ID | mirSVR Score | SR | SEN | Diff Mean | P-value |
|---|---|---|---|---|---|---|
| KIDINS220 | NP_065789 | −0.31 | 4.02E−05 | 2.65E−05 | −1.36E−05 | 1.12E−02 |
| SYT13 | NP_065877 | −0.52 | 1.06E−04 | 4.56E−05 | −6.00E−05 | 1.12E−02 |
| CALD1 | NP_149129 | −0.23 | 4.01E−04 | 2.30E−04 | −1.71E−04 | 1.13E−02 |
| ATP8A1 | NP_006086 | −0.22 | 1.06E−04 | 4.58E−05 | −5.98E−05 | 1.14E−02 |
| IKBIP | NP_710154 | −0.38 | 1.08E−04 | 6.84E−05 | −3.96E−05 | 1.15E−02 |
| UBE2F | NP_542409 | −0.68 | 1.33E−05 | 5.30E−06 | −7.98E−06 | 1.33E−02 |
| SORL1 | NP_002096 | −0.25 | 3.49E−05 | 2.19E−05 | −1.29E−05 | 1.35E−02 |
| IFRD1 | NP_001541 | −0.45 | 1.05E−04 | 8.19E−05 | −2.34E−05 | 1.57E−02 |
| AKAP1 | NP_003479 | −0.97 | 2.57E−05 | 1.36E−05 | −1.20E−05 | 1.57E−02 |
| TRPS1 | NP_054831 | −0.37 | 6.73E−05 | 5.49E−05 | −1.24E−05 | 1.60E−02 |
| RALGAPA1 | NP_055805 | −0.66 | 6.20E−05 | 4.65E−05 | −1.55E−05 | 1.67E−02 |
| TMEM131 | NP_056163 | −0.77 | 3.41E−05 | 2.31E−05 | −1.10E−05 | 1.68E−02 |
| RNF141 | NP_057506 | −0.57 | 2.10E−04 | 1.25E−04 | −8.45E−05 | 1.77E−02 |
| BTF3 | NP_001032726 | −1.01 | 1.83E−05 | 1.47E−05 | −3.53E−06 | 1.80E−02 |
| HNRNPA2B1 | NP_112533 | −0.41 | 1.33E−04 | 7.21E−05 | −6.06E−05 | 1.84E−02 |
| SULF1 | NP_055985 | −1.07 | 1.11E−05 | 6.48E−06 | −4.57E−06 | 1.85E−02 |
| SMARCA5 | NP_0035925 | −1.28 | 2.66E−04 | 1.80E−04 | −8.64E−05 | 1.89E−02 |
| S100A6 | NP_055439 | −0.24 | 7.28E−06 | 4.17E−06 | −3.10E−06 | 1.92E−02 |
| PICALM | NP_009097 | −1.03 | 3.28E−05 | 1.87E−05 | −1.41E−05 | 2.12E−02 |
| ZNHIT6 | NP_060423 | −0.39 | 7.97E−05 | 1.50E−05 | −6.48E−05 | 2.20E−02 |
| NAP1L1 | NP_004528 | −0.53 | 1.93E−05 | 8.63E−06 | −1.07E−05 | 2.35E−02 |
| ANP32B | NP_006392 | −1.34 | 1.17E−05 | 8.69E−06 | −2.99E−06 | 2.37E−02 |
| PSME4 | NP_055429 | −0.42 | 1.37E−05 | 9.08E−06 | −4.58E−06 | 2.41E−02 |
| NAAS0 | NP_079422 | −0.24 | 3.77E−05 | 2.07E−05 | −1.71E−05 | 2.43E−02 |
| HKDC1 | NP_079406 | −0.30 | 1.14E−05 | 3.39E−06 | −8.06E−06 | 2.48E−02 |
| GAK | NP_005246 | −0.74 | 6.45E−05 | 2.78E−05 | −3.67E−05 | 2.63E−02 |
| CORO1C | NP_055140 | −0.77 | 4.36E−04 | 2.07E−04 | −2.29E−04 | 2.63E−02 |
| CYP2B6 | NP_000758 | −0.37 | 1.25E−04 | 1.02E−04 | −2.37E−05 | 2.64E−02 |
| NODAL | NP_060252 | −0.79 | 1.28E−05 | 9.55E−06 | −3.27E−06 | 2.68E−02 |
| C5orf34 | NP_940968 | −0.29 | 1.59E−04 | 5.98E−05 | −9.92E−05 | 2.72E−02 |
| INVS | NP_899068 | −0.61 | 6.32E−05 | 4.35E−05 | −1.97E−05 | 2.73E−02 |
| ANO5 | NP_001136121 | −0.44 | 5.54E−06 | 2.55E−06 | −2.99E−06 | 2.91E−02 |
| HOXA1 | NP_005513 | −1.07 | 2.82E−06 | 1.53E−06 | −1.30E−06 | 3.08E−02 |
| VANGL2 | NP_065068 | −1.31 | 2.13E−05 | 1.59E−05 | −5.36E−06 | 3.10E−02 |
| ARHGAP11A | NP_055598 | −0.96 | 3.57E−05 | 2.67E−05 | −9.02E−06 | 3.11E−02 |
| SETDB2 | NP_001153780 | −1.11 | 9.39E−05 | 6.74E−05 | −2.64E−05 | 3.37E−02 |
| KIF5C | NP_004513 | −0.71 | 3.74E−05 | 2.77E−05 | −9.65E−06 | 3.40E−02 |
| DOCK5 | NP_079216 | −0.43 | 1.15E−05 | 6.57E−06 | −4.96E−06 | 3.42E−02 |
| PCBP4 | NP_065151 | −0.78 | 2.36E−05 | 1.54E−05 | −8.20E−06 | 3.43E−02 |
| PSMC6 | NP_002797 | −0.27 | 1.59E−04 | 1.11E−04 | −4.72E−05 | 3.45E−02 |
| NID1 | NP_002499 | −0.86 | 2.41E−05 | 1.01E−05 | −1.40E−05 | 3.46E−02 |
| KIF23 | NP_004847 | −1.27 | 3.96E−06 | 1.79E−06 | −2.17E−06 | 3.52E−02 |
| BCL6 | NP_001124317 | −1.32 | 2.67E−05 | 2.01E−05 | −6.50E−06 | 3.80E−02 |
| ZEB1 | NP_001121600 | −1.05 | 7.96E−06 | 5.67E−06 | −2.29E−06 | 3.82E−02 |
| FKBP11 | NP_001137254 | −0.26 | 3.22E−05 | 2.04E−05 | −1.17E−05 | 3.85E−02 |
| FBXO38 | NP_110420 | −1.13 | 4.95E−05 | 3.38E−05 | −1.56E−05 | 3.91E−02 |
| RBM20 | NP_001127835 | −0.29 | 2.52E−05 | 1.78E−05 | −7.44E−06 | 4.00E−02 |
| FBXO25 | NP_036305 | −0.30 | 7.09E−05 | 5.34E−05 | −1.75E−05 | 4.22E−02 |
| ST18 | NP_055497 | −0.57 | 3.33E−05 | 1.47E−05 | −1.86E−05 | 4.27E−02 |
| RALYL | NP_001093861 | −1.30 | 3.22E−05 | 1.78E−05 | −1.45E−05 | 4.43E−02 |
| MTM1 | NP_000243 | −0.48 | 5.43E−06 | 2.91E−06 | −2.52E−06 | 4.47E−02 |
| CENPBD1 | NP_659476 | −0.33 | 1.09E−05 | 8.18E−06 | −2.70E−06 | 4.49E−02 |
| TBC1D22B | NP_060242 | −0.37 | 4.74E−05 | 2.69E−05 | −2.05E−05 | 4.53E−02 |
| PIP4K2C | NP_001139731 | −0.28 | 4.63E−05 | 3.60E−05 | −1.03E−05 | 4.54E−02 |
| MAP4K3 | NP_003609 | −0.99 | 4.64E−05 | 3.07E−05 | −1.57E−05 | 4.55E−02 |
| PCDH15 | NP_001136239 | −1.15 | 1.09E−05 | 7.87E−06 | −3.00E−06 | 4.72E−02 |
| PRDM6 | NP_001129711 | −0.22 | 1.93E−04 | 1.51E−04 | −4.26E−05 | 4.72E−02 |
| DSCAML1 | NP_065744 | −0.75 | 1.45E−05 | 1.17E−05 | −2.72E−06 | 4.84E−02 |
| CEP350 | NP_055625 | −0.79 | 7.84E−05 | 6.00E−05 | −1.84E−05 | 4.94E−02 |
| HMGB1 | NP_002119 | −1.16 | 8.94E−06 | 5.10E−06 | −3.84E−06 | 4.96E−02 |
| PDCD6 | NP_037364 | −0.60 | 5.74E−06 | 3.26E−06 | −2.48E−06 | 4.97E−02 |

Figure 12A:
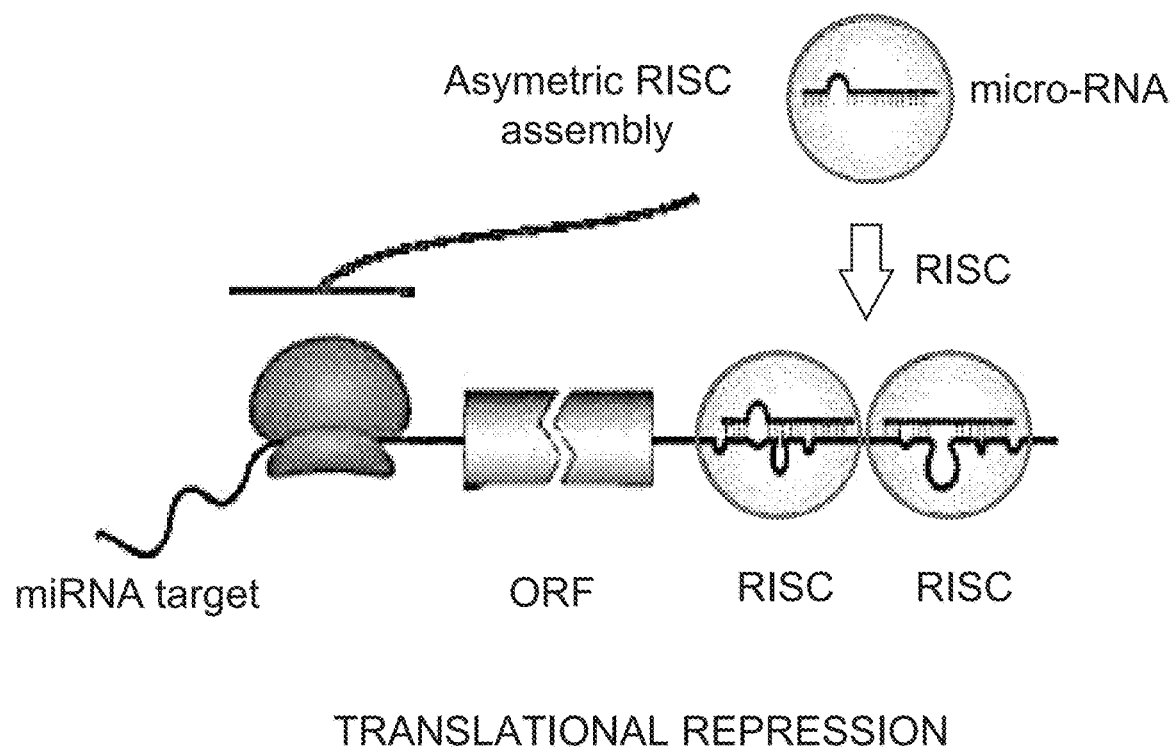
FIGS. 12A-F depict the downregulation of SEN proteins via miRNA-based translational repression and experimental validation of SA-miRNA targets.
Figure 12B:
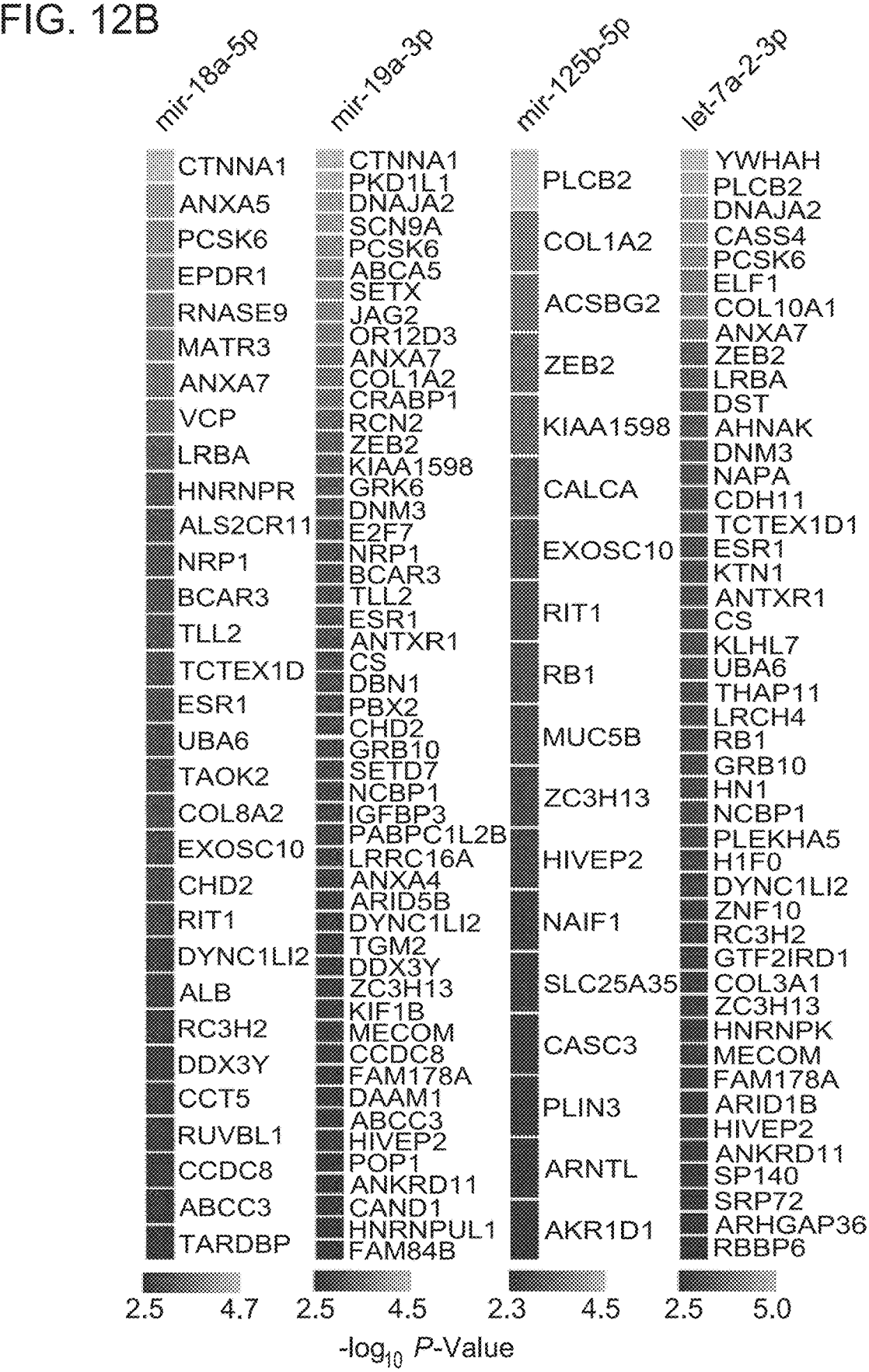
Figure 13A:
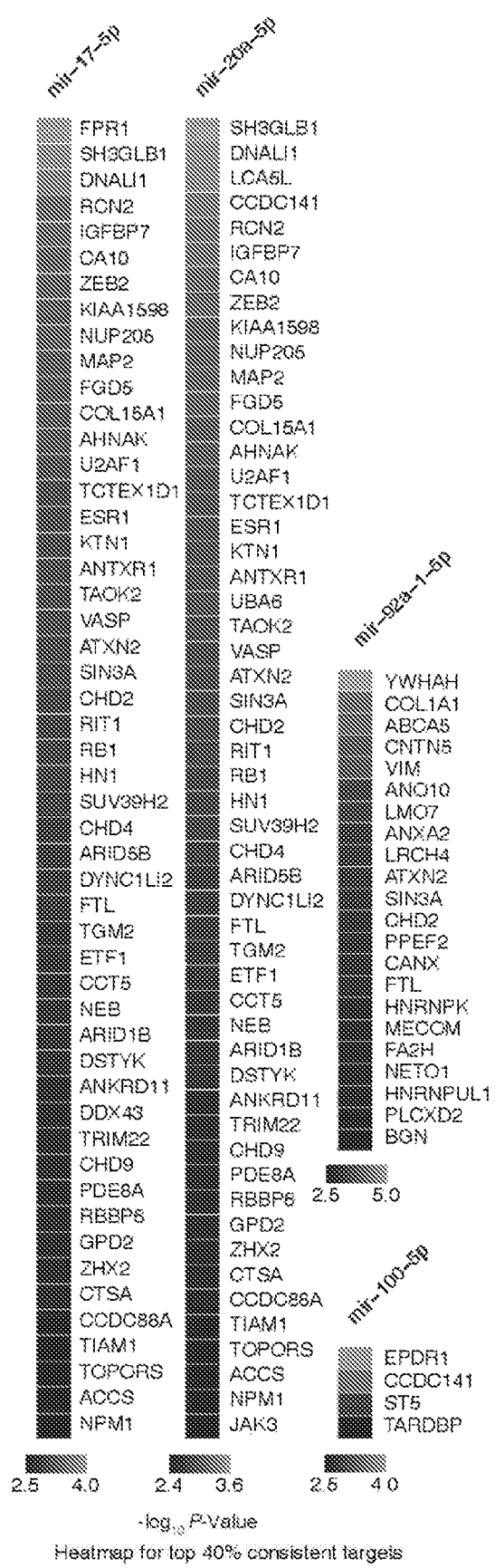
FIGS. 13A-B depict the coordinated regulation of SEN downregulated proteins by multiple. SA-associated miRNAs. Individual miRNAS are shown.

The heatmaps of representative targets of the individual SA-miRNAs are shown in FIGS. 12B and 13A, and detailed in Table 2.

Specifically, FIG. 12A depicts schematic of miRNA regulation via translational repression, resulting in reduction of protein levels. FIG. 13A depicts SEN down-regulated proteins targeted by SEN upregulated miRNAs. Differential protein expression is quantified by the Students' t-test ($-\log_{10}$ P-values shown) as described in Example 1.

Figure 10C:
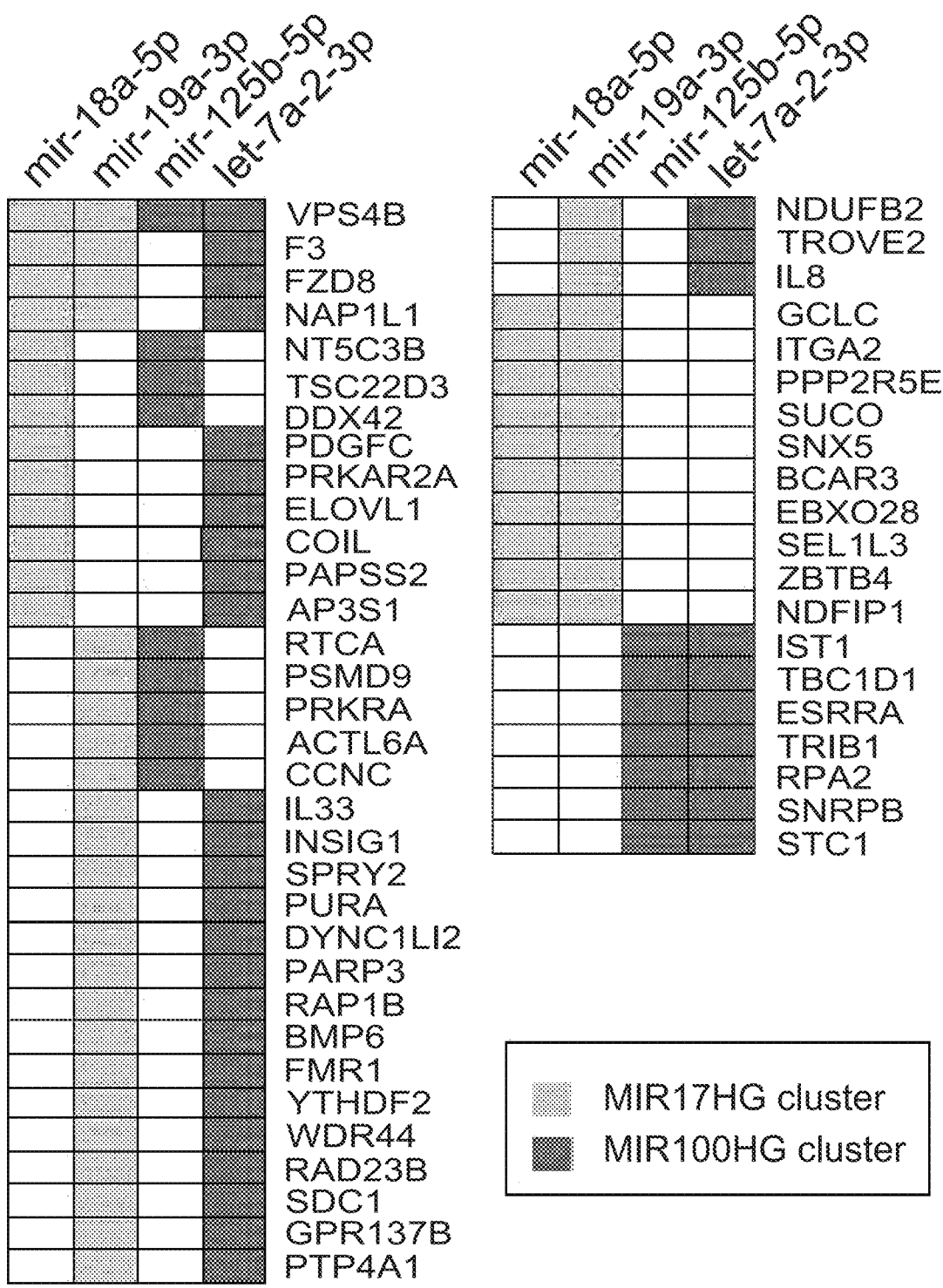
Figure 11B:
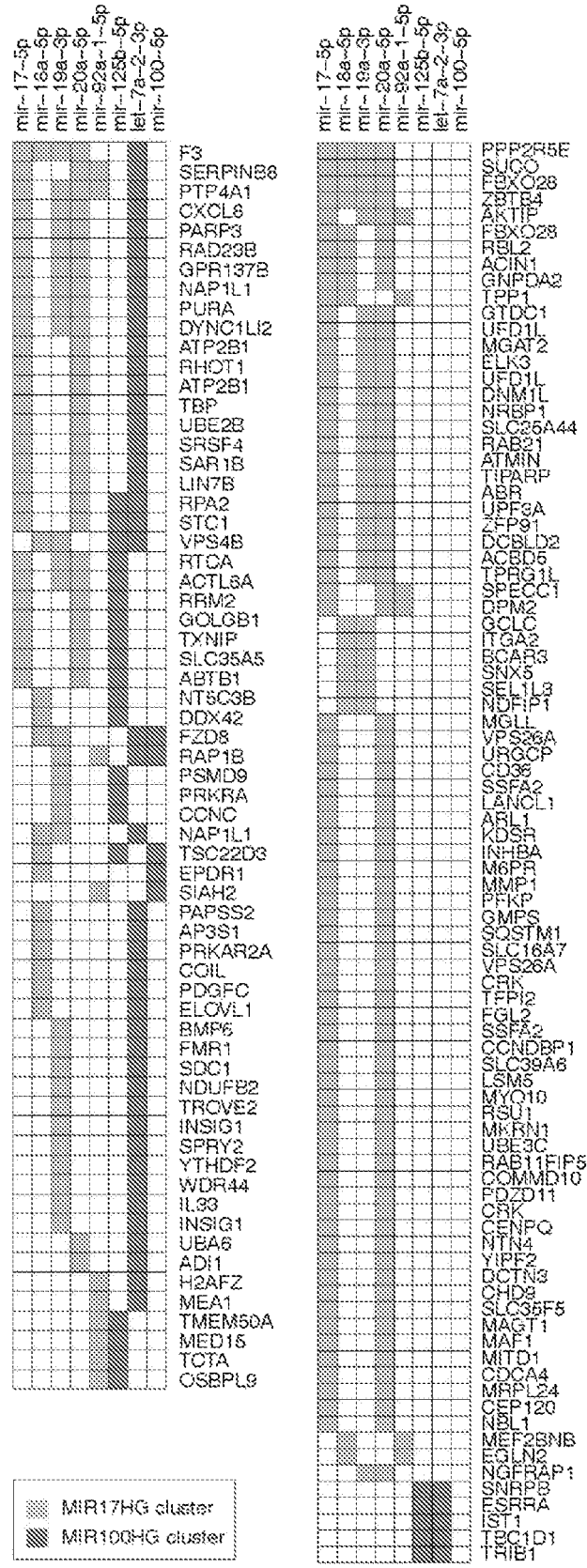
Figure 12C:
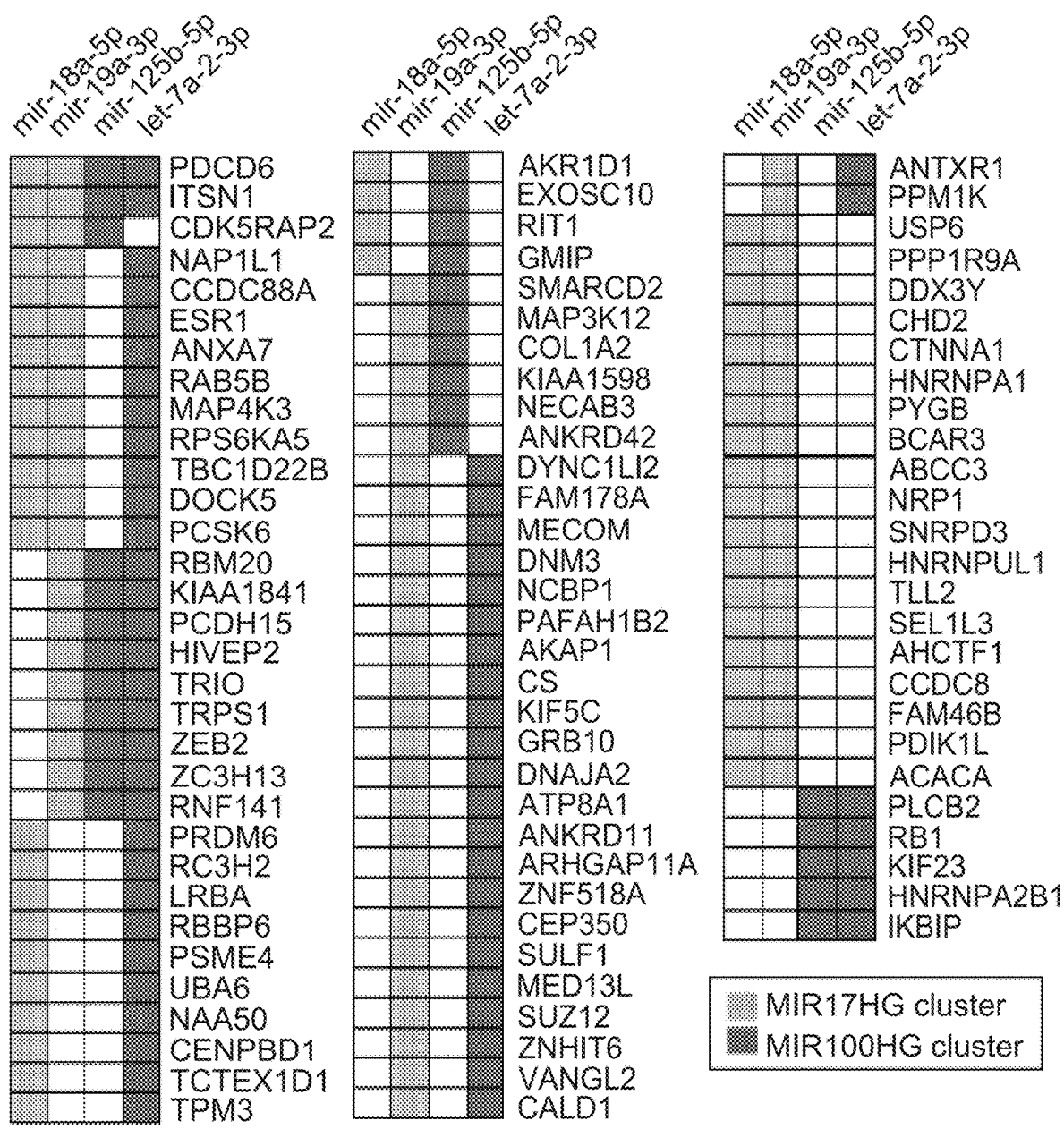
Figure 13B:
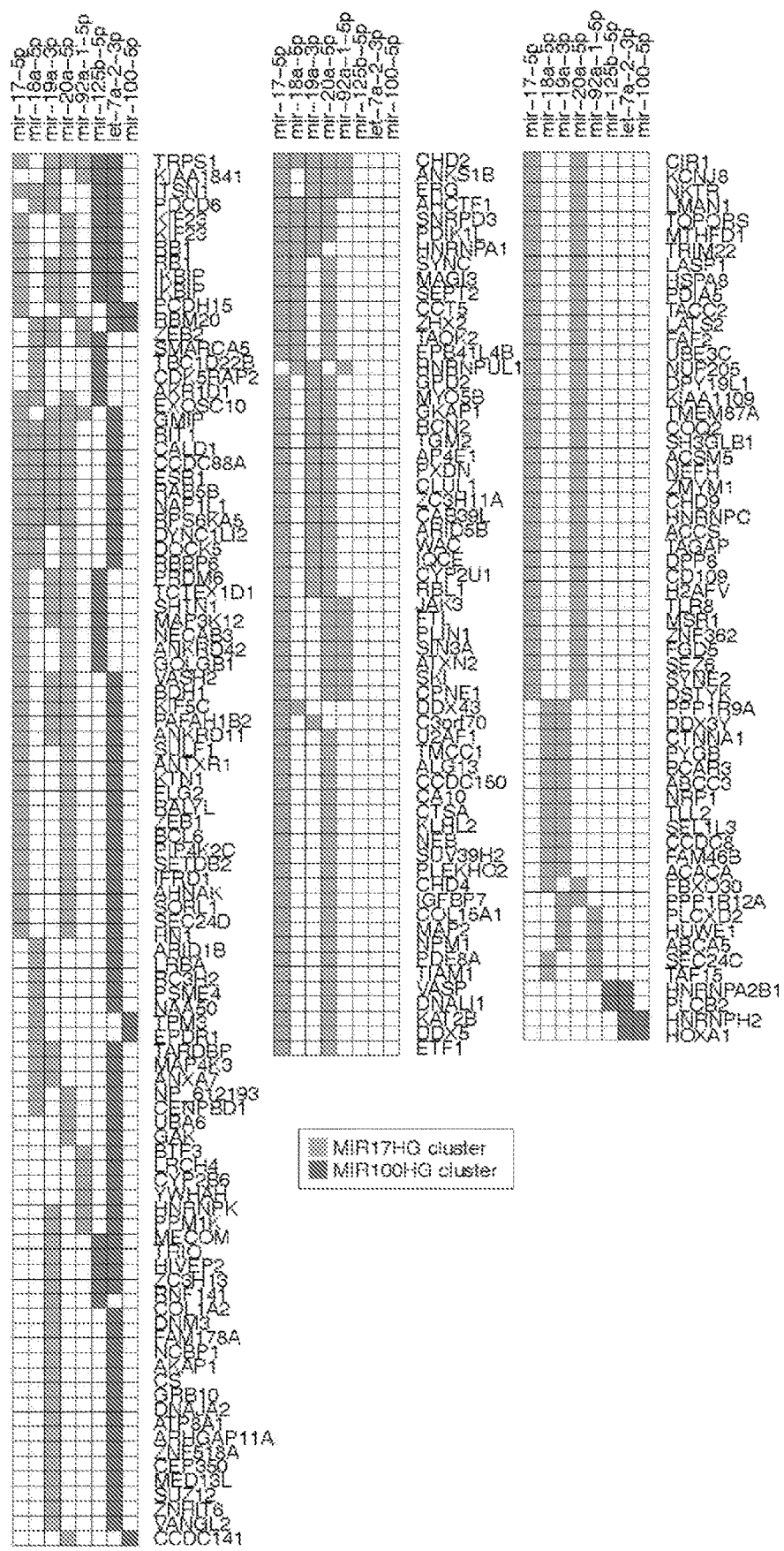

Both downregulated mRNA (FIG. 10B) and numerous SA-miRNA. targets associated with translation repression indicate co-regulation by two or more of the SA-mRNAs (FIGS. 10C, 11B, 12C and 13B). Specifically, FIG. 10C and FIG. 11B depict coordinated regulation of SEN downregulated protein coding mRNAs by multiple SA-associated miRNAs. Individual miRNAs are shown according to their miRNA gene cluster. FIG. 12C and FIG. 13B depict coordinated regulation of SEN downregulated proteins by multiple SA-associated miRNAs, Individual miRNAs are shown according to their miRNA gene cluster.

These results indicate that under physiological conditions many of the SA-miRNA target genes can be subjected to concurrent regulation by multiple co-expressing miRNAs from clusters with opposing biological roles: e.g. oncogenic versus tumor-suppressive.

Example 6: Regulation of SA-miRNA Gene Targets by microRNA

This example details the combinatorial regulation of particular SA-miRNA gene targets, (NAP1L1, SMARCD2 and USP6), by the microRNA from oncogenic MIR17HG and tumor-suppressive MIR100HG gene clusters.

To address the aspect of what function the targeting of mRNA by multiple miRNAs from the same cluster or from clusters with opposing biological activity serve, the idea that co-expression of multiple miRNAs induces stronger downregulation of their common targets was tested. Three SA-miRNA target genes that exemplify the following co-targeting arrangements were investigated: 1) a chromatin chaperone, NAP1L1 (Li, Gadue et al. 2012) targeted by multiple miRNAs from antagonistic MIG17HG and MIR100HG clusters (FIG. 10C); 2) a component of the chromatin remodeling complex, BAF complex, SMARCD2/BAF60B (Wang, Xue et al. 1996, Saccone, Consalvi et al. 2014) targeted by a single miRNA from antagonistic clusters (FIG. 12B); 3) a potent oncogene, USP6/TRE17 (Ye, Pringle et al. 2010, Pringle, Young et al. 2012) targeted by multiple miRNAs with two distinct "seed" sequences from the same cluster (FIG. 12B). FIG. 12B depicts SEN downregulated proteins targeted by SEN upregulated miRNAs. Differential protein expression is quantified by the Students' t test ($-\log_{10}$ P-values shown) as described in Example 1.

To demonstrate the regulatory effects of mir-let-7a-5p, 18a-5p and Mir-19a-3p, mir-19a-5p on NAP1L1, SMARCD2 and USP6 expression in vitro luciferase assays were performed, as below.

Luciferase Assay

The luciferase reporter constructs were built as previously described (Anbazhagan, Priyamvada et al. 2014). NAP1L1-1 (350 bp, 2713-3062) and NAP1L1-2 (675 bp, 3362-5037) from the 3' UTR of human NAR1L1 gene, USP6-1 (675 bp, 6220-6895) and USP6-2 (527 bp, 7420-7945) from the 3'UTR of human USP6 gene and SMARCD2 (525bp, 1913-2438) from the 3' UTR of human SMARCD2 gene were amplified using the primer sets (shown in Table). Purified PCR products were cloned into multiple cloning sites of the pmirGLO dual-luciferase miRNA target expression vector (Promega) downstream of the firefly luciferase gene. The primer sequences were flanked by SacI and SalI sites to generate pmirGLO-NAP1L1-1, pmirGLO-NAP1L1-2, pmirGLO-SMARCD2, pmirGLO-USP6-1 and pmirGLO-USP6-2.

TABLE 4

Luciferase vector pmirGLO construction primers

| 3'UTR of gene | Primers | |
|---|---|---|
| NAP1L1-1 (2713-3062) | Forward 5' CCC GAG CTC GCT TAA AGT ATG AGT ATGTCA CT 3' | (SEQ ID NO: 1) |
| | Reverse 5' CCC GTC GAC AAA ACA AAT CTT GGA CCT TGT GA 3' | (SEQ ID NO: 2) |
| NAP1L1-2 (3362-5037) | Forward 5' CCC GAG CTC TGA AGC AGT ATT AGC ATC ACT3' | (SEQ ID NO: 3) |
| | Reverse 5' CCC GTC GAC TAT TAT TTC ACC ATC ACC ATT TAC A 3' | (SEQ ID NO: 4) |
| SMARCD2 (1913-2438) | Forward 5' CCC GAG CTC CTG CTC AGG GAT CTT TCT TCC C 3' | (SEQ ID NO: 5) |
| | Reverse 5' CCC GTC GAC AAA AAA AGT GGC TCC CAC ATA GA 3' | (SEQ ID NO: 6) |
| USP6-1 (6220-6895) | Forward 5' CCC GAG CTC ATA TGT AGT GAG TAT AGA GTT TAC CCA A 3' | (SEQ ID NO: 7) |
| | Reverse 5' CCC GTC GAC TTT GCA TGT GTT CTC TCT TTT TTA AAG T3' | (SEQ ID NO: 8) |
| USP6-2 (7420-7945) | Forward 5' CCC GAG CTC AAA TTG AAA TCC TTT TCA GAA AAA A 3' | (SEQ ID NO: 9) |
| | Reverse 5' CCC GTC GAC AAA AAC AGC ACA TAG AGG C 3' | (SEQ ID NO: 10) |

For this, corresponding 3'UTRs of: (1) NAP1L1 (3'UTR 2713-3062 and a portion of 3'UTR 3362-5037) shown in FIGS. 10D and 10E, (2) USP6 (portions of 3'UTR 6220-6895 and 3'UTR 7420-79451 shown in FIGS. 12E and 12F, and (3) 3'UTR 1913-2438 of SMARC D2 (FIG. 12D) genes were cloned into the pGL3-promoter vector, immediately downstream of the luciferase gene. These reporter constructs were transfected into 293T cells lacking endogenous expression of mature mir-let-7p-2-3p, mir-18a-5p, mir-19a-3p or mir-125b-5p miRNAs, either alone or in combination with synthetic small, double-stranded RNA molecules designed to mimic endogenous mature miRNA molecules, mimic miRNA (Sigma, St. Louis, Mo.), as previously described (Anbazhagan, Privamvada et al. 2014, Meseguer, Martinez-Zamora et al. 2015). To validate, mimic miRNAs were transfected either alone or in combinations as described below and shown in FIGS. 10D, 10E and 12D, 12E, 12F.

Mimic miRNA Transfection Studies

The hADSCs were seeded on 4-well slides at a density of $1 \times 10^4$ cells/well one day before transfection with 5 pmol and 10 pmol each of different microRNA mimics to SA-miRNA using Fugene 6 (Promega). 48 h after transfection, SA-β-gal staining was performed according to manufacturer's instructions (BioVision), RNA extraction and the subsequent realtime qPCR were performed to detect target gene expression.

The ready-to-use microRNA mimics are small, double-stranded RNA molecules designed to mimic endogenous mature microRNA (miRNA) molecules. When transfected into cells, they can regulate gene expression in different manners, including translational repression, mRNA cleavage and deadenylation, imitating the native miRNA. The relative luciferase activity was measured as previously described (Anbazhagan, Priyamvada et al. 2014). $1 \times 10^4$ 293T cells were seeded per well into 96-well plates one day before transfection with 500 ng pmirGLO/pmirGLO-UTR constructs alone or in combination with 1 pmol different microRNA mimics to SA-miRNA (Sigma, MISSION® microRNA Mimic), using Fugene6 (Promega) according to manufacturer's instructions. Forty-eight hours post-transfection, cells were lysed in a passive lysis buffer (Promega). The luciferase activity was then determined using the Dual Luciferase Assay Kit (Promega). Renilla luciferase activity was used as a control. Subsequently, the firefly luciferase activity was normalized to renilla luciferase activity. The 3'-UTR activity was calculated as a ratio of firefly luciferase to renilla luciferase. The experiments were repeated in triplicate.

Figure 10D:
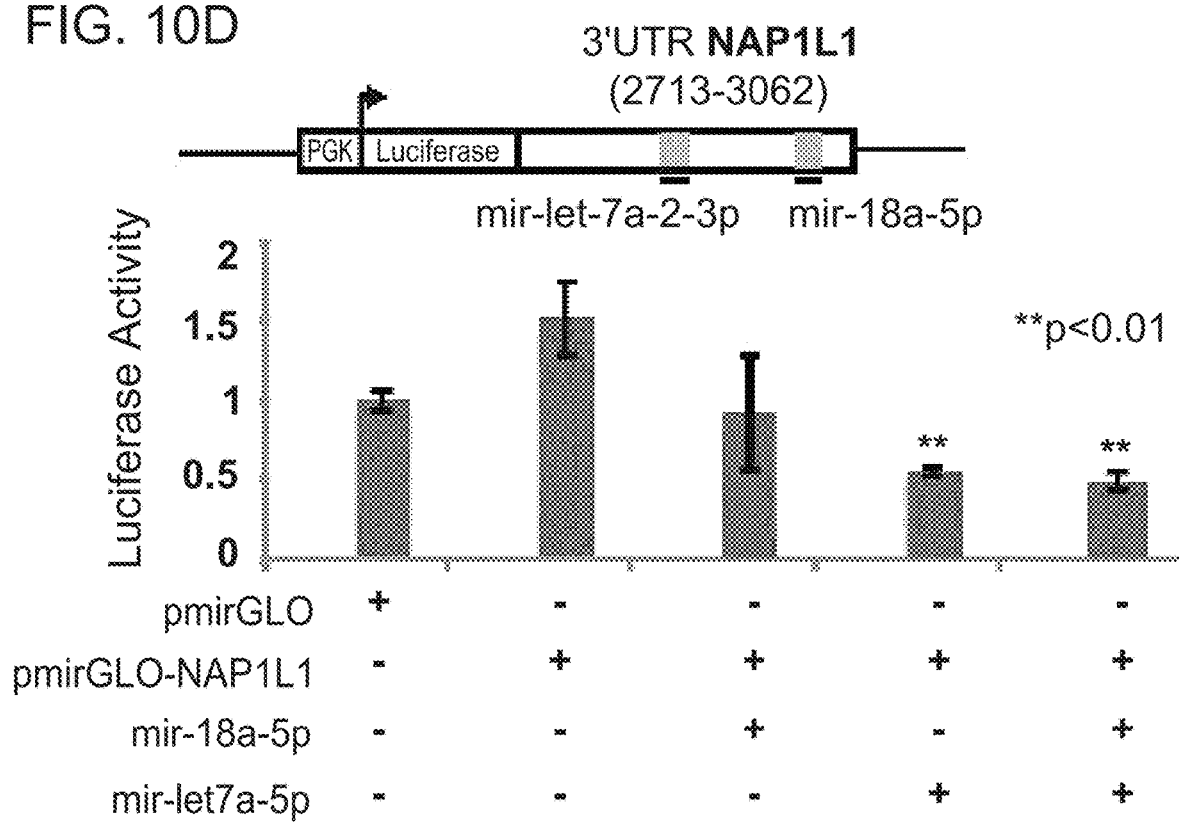
Figure 10E:
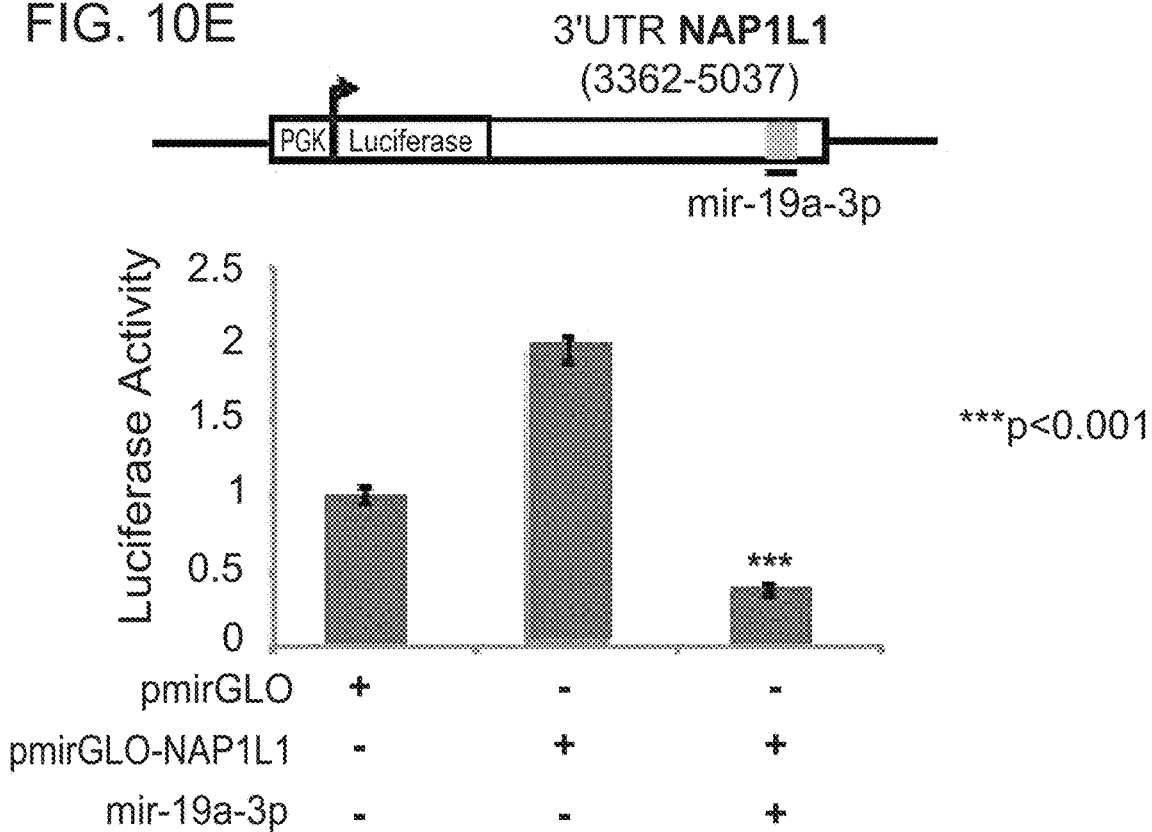
Figure 12D:
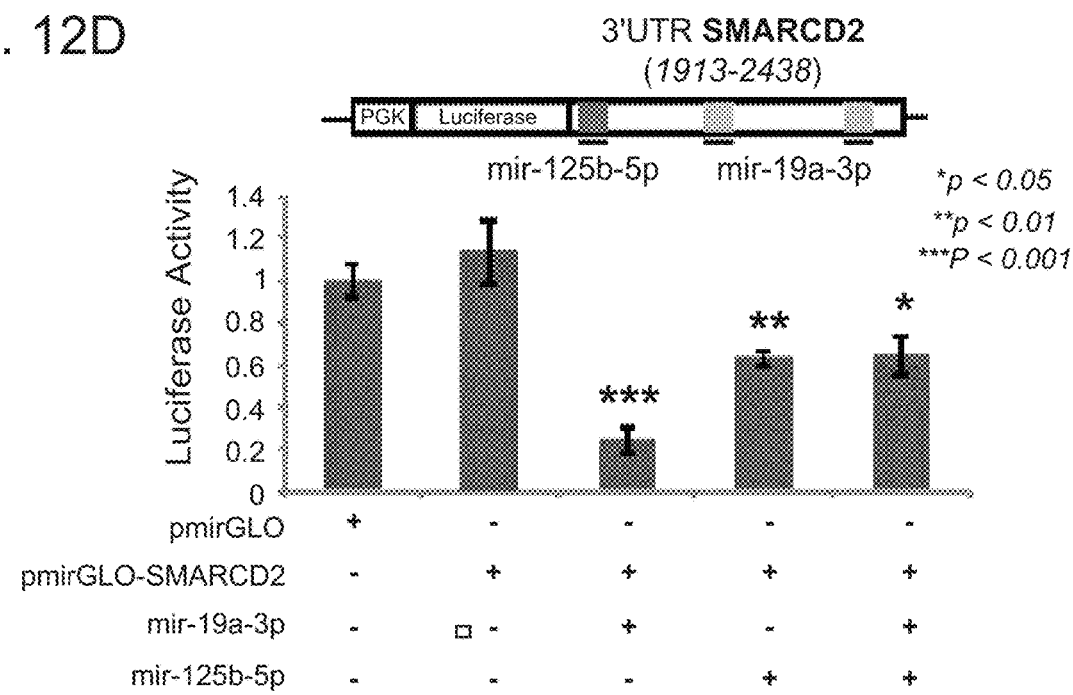

It was observed that luciferase activity in cells transfected with pGL3-NAP1L1-3'UTR was significantly reduced as compared with cells transfected with the control pGL3 vector only by mir-let-7a-2-3p (47%) and mir-19a-3p (81%) as shown in FIGS. 10D and 10E, respectively. No significant downregulation of luciferase activity of pGL3-NAP1L1-3'UTR was observed when the mir-18a-5p mimic was used (FIG. 10D); although, the mir-18a-5p mimic efficiently downregulates luciferase activity of pGL3-USP6-3'UTR (65%) in similar experiments shown in FIG. 12F. This suggests that NAP1L1 is efficiently targeted by mir-let-7a-2-3p and 19a-3p, but not mir-18a-5p, which originates from the same cluster as mir-19a-3p, (MIR17HG). Analysis of pGL3-SMARCD2-3'UTR revealed a similar trend and confirmed that SMARCD2 is a target of two SA-miRNAs:mir-19a-3p and mir-125b-5p (FIG. 12D).

Figure 12E:
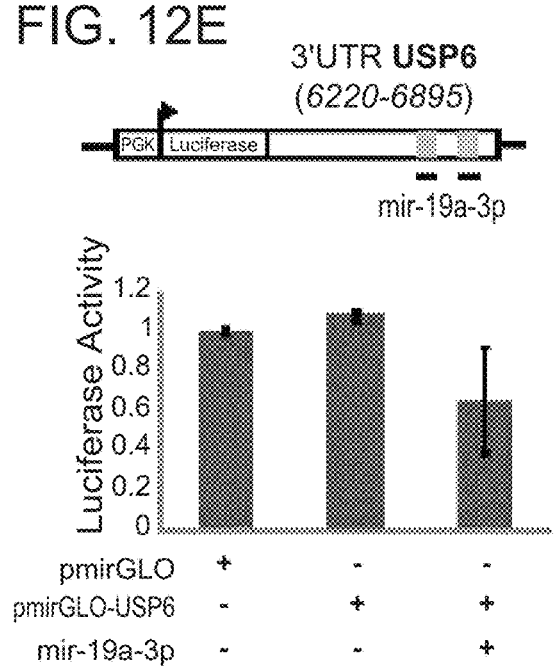

In a similar experiment, two composite 3'UTR parts of the USP6 gene (FIGS. 12E and 12F) were tested. The 3'UTR of the USP6 gene responded with statistical significance to only one miRNA from the MIR17HG cluster. Transient transfection of the mimic of mir-18a-5p resulted in a 65% downregulation of luciferase activity (FIG. 12F), while transfection of the mimic of mir-19a-3p showed no significant change (FIG. 12E). These findings support that preferential use of SA-miRNAs originating from the same cluster for the concurrent regulation of the same genes.

The ability of pairs of miRNAs to synergistically regulate mutual targets in order to facilitate more effective target repression was investigated, a phenomenon known as cooperating miRNAs (Hausser and Zavolan 2014). Although each single SA-miRNA efficiently downregulated the NAP1L1, SMARCD2 and USP6 UTRs in transient transfection experiments (FIGS. 10D, 10E, 12D, 12E, 12F), data has shown that simultaneous transfection of multiple microRNA mimics targeting the same UTR does not increase the efficiency of target downregulation in all of the tested reporter assay combinations. This argues against the idea that a stronger downregulation of common gene targets could be achieved by multiple simultaneously co-expressing miRNAs, thus leading to a larger response of the target to miRNA perturbation.

FIGS. 10D and 10E shows coordinated regulation of NAP1L1 UTRs by SA-miRNAs. Schematic diagrams of predicted target sites of SA-miRNAs in the two distal portions of NAP1L1 UTRs: A portion from 2713 to 3062 from the transcriptional start site TSS (FIG. 10D) and a portion from 3362 to 5037 from the TSS (FIG. 10E). Repression of luciferase reporters bearing the UTRs (pmirGLO-NAP1L1) and corresponding control luciferase vector pmirGLO by mimic SA-miRNAs (n=3, mean=±SD, two-tailed type2, Student t-test, compared to the control vector pmirGLO), P-value (p) related to experimental measurements are listed over the graphs, where *$p<0.001$, $p<0.01$.

Figure 12F:
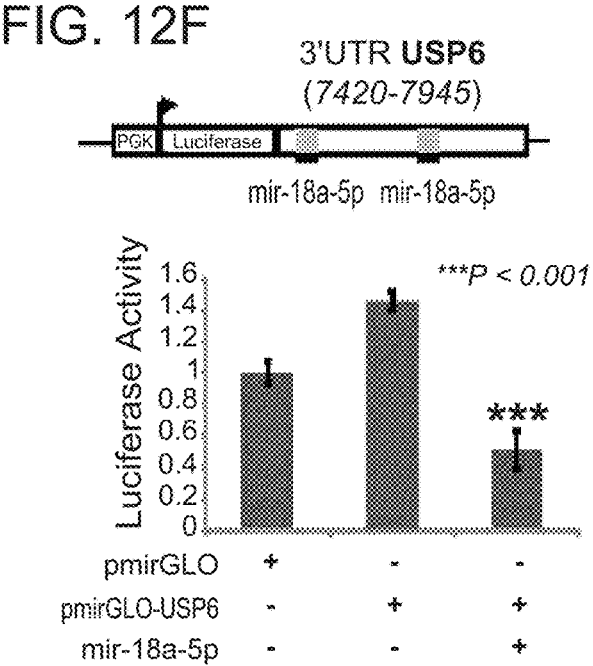

FIG. 12D depicts coordinated regulation of SMARCD2 UTR by SA-miRNAs. Schematic diagrams of predicted target sites of SA-miRNAs in the (1913-2438) portion of SMARCD2 FIGS. 12E and 12F depict coordinated regulation of USP6 UTRs by SA-miRNAs. Schematic diagrams of predicted target sites of SA-miRNAs in the two distal portions of USP6 UTRs: a portion from 6220 to 6895 from the transcriptional start site TSS FIG. 12E and a portion from 7420 to 7945 from the TSS FIG. 12F. Repression of luciferase reporters bearing the UTRs (pmirGLO-SMARCD2 and pmirGLO-USP6) and corresponding control luciferase vector pmirGLO by mimic SA-miRNAs (n=3, mean=±SD, two-tailed, type 2, Student t-test, compared to the control vector pmirGLO). P-value (p) related to experimental measurements are listed over the graphs, where *$p<0.001$, $p<0.01$, *$p<0.05$.

These data support that of miRNA cooperativity might imply a much more sophisticated mechanism of regulation of miRNA targets than was initially anticipated. For example, selective, physiologically-relevant expression of cooperating miRNAs could be adopted by cells to facilitate distinctive and fine-tuned gene expression patterns to meet the requirements of different biological scenarios and this phenomenon is unlikely to be appropriately tested in transient transfection experiments.

Example 7: Network-based Functional Enrichment Analysis of SA-miRNA Targets

This example details molecular pathways regulated by the identified SA-miRNAs.

Since clustered SA-miRNAs are co-expressed at different levels upon senescence in hADSCs (FIGS. 5C and 5D), it is expected that they jointly regulate specific molecular pathways not only by co-targeting individual genes, but also by targeting differential components of the same pathways. A network-based functional enrichment analysis method was developed in order to visually elucidate the potential roles of, and interactions among, integrated molecular networks of functionally related gene-targets of SA-miRNAs in hADSCs.

Network-Based Functional Enrichment Analysis

The set of genes that were characterized as both targets of SEN upregulated miRNAs (FIG. 5) and found to be down-regulated in SEN hADSCs were manually analyzed based on functional annotations in the STRING database (Szklarczyk, Franceschini et al. 2011). Proteins from four annotation categories of interest—cell cycle, chromatin, transcription/translation and histone methyltransferases—were selected for functional enrichment analysis using a network-based approach. The network enrichment approach developed and applied here yields function-specific sub-networks based on the functional interactions in the STRING database, with edge confidence levels >0.4. For each set of functionally annotated proteins, a Steiner tree was built; the Steiner tree is the minimal spanning tree that connects all of the functionally annotated seed proteins by introducing the fewest number of intermediate proteins (i.e. Steiner nodes). Functional enrichment for these sub-networks was evaluated via the implementation of a previously described simulation approach (Talkowski, Rosenfeld et al. 2012). For each function-specific sub-network, the observed score (NS) is computed NS=G/T where G is the number of functionally annotated seed proteins and T is the total number of proteins in the network. A null set of expected NS scores is then simulated by randomly selecting G seed proteins from the same underlying degree distribution and then constructing the Steiner tree of size T from these random seeds. The P-value for each sub-network is computed via a z-test comparing the observed NS score versus the expected NS score distribution.

Figure 14:
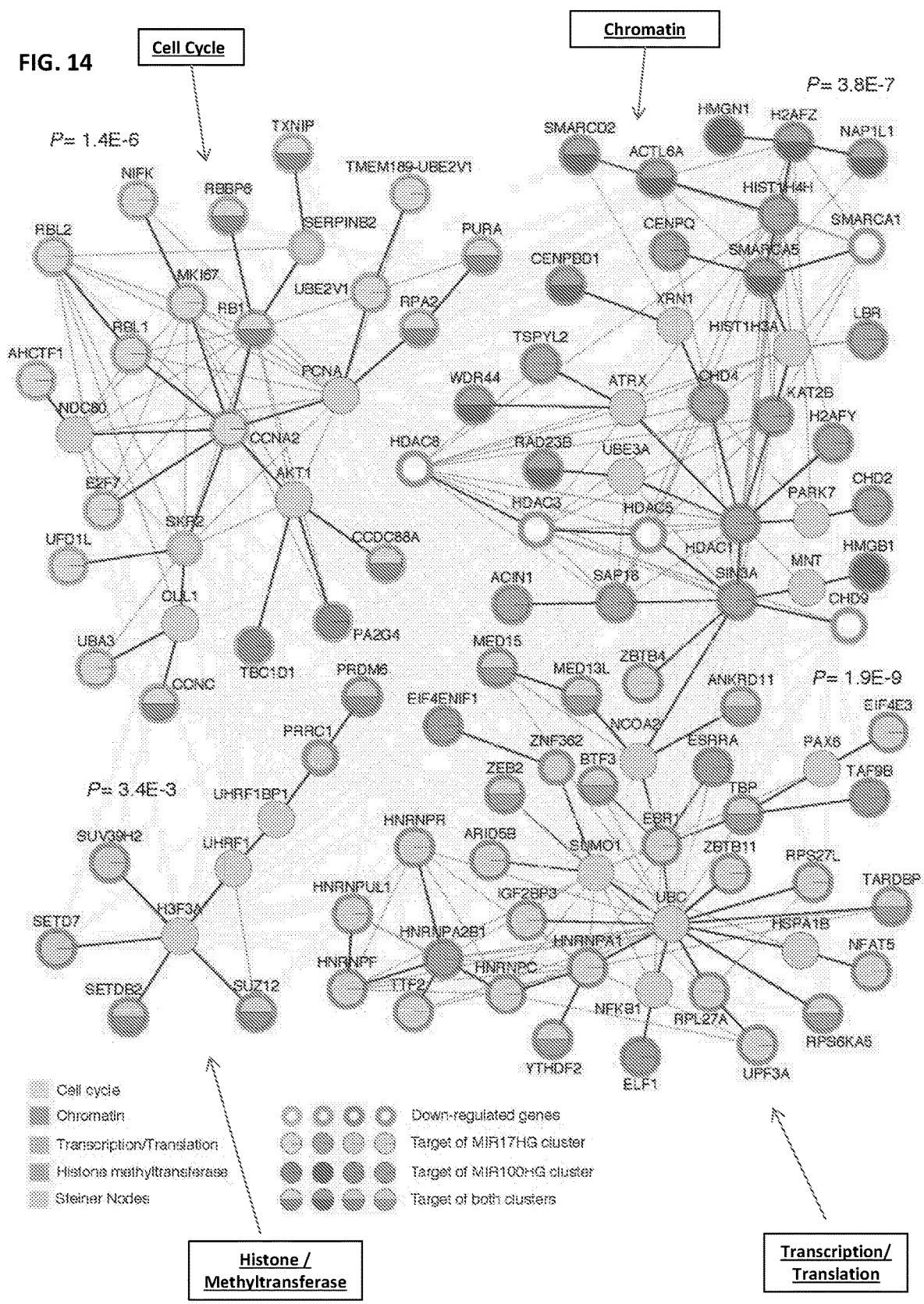
FIG. 14 depicts functional relationships and enrichment of SEN downregulated targets of SA-associated miRNAs.

SA-miRNA targets that were found to be downregulated at the mRNA (FIG. 10 and Table 2) or protein level (FIG. 12, and Table 3), were interrogated based on their functional annotations and used to seed the network analysis (von Mering, Jensen et al. 2005). Four categories of particular interest were identified as relevant to the establishment and maintenance of the senescent phenotype: cell cycle, chromatin, transcription/translation, and histone methyltransferases. To identify functional interactions among the corresponding SA-miRNA gene targets from these four categories, these genes were then linked in a network by edges that represent known relationships between the genes based on a variety of functional interactions, such as physical protein-protein interactions, gene co-expression and text mining co-relationships. Genes that do not have any direct known relationships of this kind are transitively linked via the minimum number of possible intermediate gene nodes, some of which are not targets of SA-miRNAs, but have been downregulated in SEN hADSCs (FIG. 14, open circles). The intermediate nodes, which were not initially identified as miRNA targets or downregulated upon senescence, are the so-called Steiner nodes shown in gray in FIG. 14 and described above.

The network functional enrichment analysis resulted in the elucidation of four clearly defined function-specific sub-networks, each of which corresponds to a distinct functional category, along with the inter-relationships between these functional groups (FIG. 14). The coalescence of genes with the same function into discrete sub-networks supports their close functional relationships and tight interactions, and the statistical significance of the functional enrichment within these groups is represented by P-values determined via simulation of random Steiner networks with the same number of genes from that particular functional category as described in the above "Network-based Functional Enrichment Analysis" paragraph. The P-values represent the probability of reconstructing sub-networks of the observed sizes, or smaller, by chance; in other words, they provide significance levels for the observed functional coherence of the sub-network.

Specifically, FIG. 14 depicts functional relationships and enrichment of SEN downregulated targets of SA-associated miRNAs. Four functional categories of genes were evaluated for their relationships and functional enrichment using a network-based approach as described above. The network nodes represent genes and are coded based on their functional category. Function is annotated. Gene nodes are labeled in regards to targeted miRNA (see node label key in the Figure). Edges represent annotated protein relationships from the STRING database. Black solid edges represent connections of the sub-network minimal spanning trees (i.e. Steiner trees), dark gray dashed edges show additional sub-network connections, and light gray dashed edges represent connections between function-specific sub-networks. P-values indicate the extent to which each function-specific sub-network is enriched for genes from that particular functional category. Steiner nodes are shown in grey. Downregulated genes, which are not targeted by SA-miRNAs are shown with thickened rim based on their functional category.

These data indicate that SA-miRNAs jointly regulate molecular pathways not only by co-targeting individual genes, but also by targeting different components of the pathways that interconnect and could be relevant to senescence of hADSCs.

The invention claimed is:

1. A method of selecting a sample comprising a population of stem cells, for use in a stem cell-based therapy, the method comprising:
   a. measuring the expression levels of at least two miRNAs in the sample, wherein the at least two miRNAs are mir-125b1 and mir-let7a-2;
   b. comparing the expression levels of the at least two miRNAs to a reference standard;
   c. using the comparison to determine the quality of the stem cells in the sample wherein an increase in the expression level of the at least two miRNAs compared to the reference standard is correlated with a decrease in the quality of the stem cells in the sample and the quantity of productive stem cells in the sample;
   d. determining the percentage of unproductive stem cells in the sample, wherein the percentage of unproductive stem cells in the sample is determined by:
      detecting the increase in the expression level of the at least two miRNAs; and
      detecting one or more stem cell features selected from:
         the stem cells are not or are minimally self-renewing;
         the stem cells are senescent or are nearing senescence;
         the stem cells have been passaged greater than 6 times;
         the stem cells exhibit low or no growth potential; and
         the stem cells exhibit tumorigenic potential; and
   e. (i) selecting and preparing the sample for use in a stem cell-based therapy if 50% or less than 50% of cells in the sample comprise unproductive stem cells by separating unproductive cells from the sample and purifying or enriching the sample for productive stem cells or (ii) separating unproductive cells from the sample if greater than 50% of cells in the sample comprise unproductive stem cells.

2. The method of claim 1, wherein the unproductive stem cells are not self-renewing.

3. The method of claim 1, wherein the sample comprises human stem cells.

4. The method of claim 1, wherein the sample comprises mesenchymal stem cells.

5. The method of claim 1, wherein the sample comprises adipose tissue.

6. The method of claim 1, wherein the sample comprises mesodermal tissue differentiated from induced pluripotent stem cells.

7. The method of claim 1, wherein the sample comprises bone marrow-derived stem cells.

8. The method of claim 1, wherein the separating step is carried out by any one or more of magnetic beads technology, differential attachment assays, visual morphological inspections, and differential migration assays.

9. The method of claim 1, wherein the separating of step (e)(i) is carried out by any one or more of magnetic beads technology, differential attachment assays, visual morphological inspections, and differential migration assays.

10. The method of claim 1, wherein the expression level of the miRNAs is increased by at least 2-fold.

11. The method of claim 1, wherein the enriching or purifying of step (e)(i) comprises incubating a β-galactosidase substrate with the stem cells and selecting for β-galactosidase activity.

* * * * *

SEQUENCE LISTING

```
<160> NUMBER OF SEQ ID NOS: 10

<210> SEQ ID NO 1
<211> LENGTH: 32
<212> TYPE: DNA
<213> ORGANISM: Artificial Sequence
<220> FEATURE:
<223> OTHER INFORMATION: NAP1L1-1 forward primer

<400> SEQUENCE: 1
cccgagctcg cttaaagtat gagtatgtca ct                                   32

<210> SEQ ID NO 2
<211> LENGTH: 32
<212> TYPE: DNA
<213> ORGANISM: Artificial Sequence
<220> FEATURE:
<223> OTHER INFORMATION: NAP1L1-1 reverse primer

<400> SEQUENCE: 2
```

```
cccgtcgaca aaacaaatct tggaccttgt ga                                32
```

<210> SEQ ID NO 3
<211> LENGTH: 30
<212> TYPE: DNA
<213> ORGANISM: Artificial Sequence
<220> FEATURE:
<223> OTHER INFORMATION: NAP1L1-2 forward primer

<400> SEQUENCE: 3

```
cccgagctct gaagcagtat tagcatcact                                   30
```

<210> SEQ ID NO 4
<211> LENGTH: 34
<212> TYPE: DNA
<213> ORGANISM: Artificial Sequence
<220> FEATURE:
<223> OTHER INFORMATION: NAP1L1-2 reverse primer

<400> SEQUENCE: 4

```
cccgtcgact attatttcac catcaccatt taca                              34
```

<210> SEQ ID NO 5
<211> LENGTH: 31
<212> TYPE: DNA
<213> ORGANISM: Artificial Sequence
<220> FEATURE:
<223> OTHER INFORMATION: SMARCD2 forward primer

<400> SEQUENCE: 5

```
cccgagctcc tgctcaggga tctttcttcc c                                 31
```

<210> SEQ ID NO 6
<211> LENGTH: 32
<212> TYPE: DNA
<213> ORGANISM: Artificial Sequence
<220> FEATURE:
<223> OTHER INFORMATION: SMARCD2 reverse primer

<400> SEQUENCE: 6

```
cccgtcgaca aaaaagtgg ctcccacata ga                                 32
```

<210> SEQ ID NO 7
<211> LENGTH: 37
<212> TYPE: DNA
<213> ORGANISM: Artificial Sequence
<220> FEATURE:
<223> OTHER INFORMATION: USP6-1 forward primer

<400> SEQUENCE: 7

```
cccgagctca tatgtagtga gtatagagtt tacccaa                           37
```

<210> SEQ ID NO 8
<211> LENGTH: 37
<212> TYPE: DNA
<213> ORGANISM: Artificial Sequence
<220> FEATURE:
<223> OTHER INFORMATION: USP6-1 reverse primer

<400> SEQUENCE: 8

```
cccgtcgact ttgcatgtgt tctctctttt ttaaagt                           37
```

<210> SEQ ID NO 9
<211> LENGTH: 34
<212> TYPE: DNA

```
<213> ORGANISM: Artificial Sequence
<220> FEATURE:
<223> OTHER INFORMATION: USP6-2 forward primer

<400> SEQUENCE: 9
cccgagctca aattgaaatc cttttcagaa aaaa                              34

<210> SEQ ID NO 10
<211> LENGTH: 28
<212> TYPE: DNA
<213> ORGANISM: Artificial Sequence
<220> FEATURE:
<223> OTHER INFORMATION: USP6-2 reverse primer

<400> SEQUENCE: 10
cccgtcgaca aaacagcac atagaggc                                      28
```